United States Patent
Prasad et al.

(10) Patent No.: US 10,865,236 B2
(45) Date of Patent: Dec. 15, 2020

(54) **BISPECIFIC ANTIGEN-BINDING MOLECULES THAT BIND A *STAPHYLOCOCCUS* TARGET ANTIGEN AND A COMPLEMENT COMPONENT AND USES THEREOF**

(71) Applicant: Regeneron Pharmaceuticals, Inc., Tarrytown, NY (US)

(72) Inventors: Brinda Prasad, Long Island City, NY (US); Andrew J. Murphy, Croton-on-Hudson, NY (US); Karolina Meagher, Yorktown Heights, NY (US); Peter Mason, Somerville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/143,901

(22) Filed: Sep. 27, 2018

(65) Prior Publication Data

US 2019/0100575 A1 Apr. 4, 2019

Related U.S. Application Data

(60) Provisional application No. 62/565,569, filed on Sep. 29, 2017, provisional application No. 62/654,576, filed on Apr. 9, 2018.

(51) Int. Cl.
| | |
|---|---|
| *C07K 16/12* | (2006.01) |
| *C07K 16/18* | (2006.01) |
| *A61P 31/04* | (2006.01) |
| *A61K 39/40* | (2006.01) |
| *C12N 15/62* | (2006.01) |
| *A61K 39/00* | (2006.01) |

(52) U.S. Cl.
CPC .......... *C07K 16/1271* (2013.01); *A61K 39/40* (2013.01); *A61P 31/04* (2018.01); *C07K 16/18* (2013.01); *C12N 15/62* (2013.01); *A61K 2039/505* (2013.01); *A61K 2039/572* (2013.01); *C07K 2317/31* (2013.01); *C07K 2317/734* (2013.01); *C07K 2317/92* (2013.01)

(58) Field of Classification Search
None
See application file for complete search history.

(56) References Cited

U.S. PATENT DOCUMENTS

2016/0068589 A1 3/2016 Lydon

OTHER PUBLICATIONS

Greenspan et al. 1999 (Defining epitopes: Its not as easy as it seems; Nature Biotechnology, 17:936-937) (Year: 1999).*
Rudikoff et al. 1982 (Single amino acid substitution altering antigen-binding specificity; PNAS, USA, 79(6):1979-1983) (Year: 1982).*
Sela-Culang et al. 2013 (The structural basis of antibody-antigen recognition; Frontiers in Immunology 4(302):1-13) (Year: 2013).*
Goel et al. 2004 (Plasticity within the Antigen Combining Site May Manifest as Molecular Mimicry in the Humoral Immune Response; The Journal of Immunology 173(12):7358-7367 (Year: 2004).*
Edwards et al. 2003 (The remarkable flexibility of the human antibody repertoire; isolation of over one thousand different antibodies to a single protein, BlyS. Journal of Molecular Biology 334:103-118) (Year: 2003).*
PCT International Search Report and Written Opinion in International Application PCT/US2018/053064, dated Mar. 14, 2019, 25 pages.
Farrell, C. et al., "Detection of IgG aggregates or immune complexes using sold-phase C1q and protein A-rich *Staphylococcus aureus* as an indicator system", Scandinavian Journal of Immunology 1975, vol. 4, No. 7, 1975, pp. 673-680.
Pancari, Gregory et al., "Charachterization of the mechanism of protection mediated by CS-D7, a monoclonal antibody to *Staphylococcus aureus* iron regulated surface determinant B (IsdB)", Frontiers in Cellular and Infection Microbiology, vol. 2, Jan. 1, 2012, p. 13 ages.

* cited by examiner

*Primary Examiner* — Mary Maille Lyons
(74) *Attorney, Agent, or Firm* — FisherBroyles, LLP; Cara L. Crowley-Weber; Lisa Dornbach Flanagan

(57) ABSTRACT

According to certain embodiments, the present disclosure provides bispecific antigen-binding molecules comprising a first antigen-binding domain that specifically binds a *Staphylococcus* species target antigen and a second antigen binding domain that binds a complement component. In certain embodiments, the bispecific antigen-binding molecules of the present disclosure are capable of binding to the *Staphylococcus* species target antigen with an $EC_{50}$ of about 10 nM or less, and/or are capable of promoting complement deposition on the *Staphylococcus* species with an $EC_{50}$ of about 10 nM. The antibodies of the disclosure are useful for treating diseases in which inhibition or reduction of the growth of a *Staphylococcus* species is desired and/or therapeutically beneficial, for example, for treating staphylococcal infections including a skin infection, cellulitis, pneumonia, meningitis, urinary tract infection, toxic shock syndrome, endocarditis, osteomyelitis, bacteremia, or sepsis, or for preventing or treating a *staphylococcus* infection that occurs as a result of a surgical procedure.

16 Claims, No Drawings
Specification includes a Sequence Listing.

BISPECIFIC ANTIGEN-BINDING MOLECULES THAT BIND A *STAPHYLOCOCCUS* TARGET ANTIGEN AND A COMPLEMENT COMPONENT AND USES THEREOF

CROSS-REFERENCE TO RELATED APPLICATIONS

This application claims the benefit under 35 U.S.C. § 119(e) of U.S. provisional application Nos. 62/565,569 filed Sep. 29, 2017 and 62/654,576 filed Apr. 9, 2018, both of which are herein specifically incorporated by reference in their entireties.

FIELD OF THE DISCLOSURE

The present disclosure relates to a bispecific antigen binding molecule that binds to a *Staphylococcus* species target antigen and a complement component, and uses thereof.

BACKGROUND

Human infections with *Staphylococcus*, especially methicillin resistant *Staphylococcus aureus*, are approaching epidemic status. In 2005, infections with *Staphylococcus aureus* had a mortality rate of 6.3 per 100,000 people in the US. As a result, there has been significant research into the development of a vaccine. Vaccines strategies have targeted capsular polysaccharides, iron scavenging protein IsdB, clumping factor a, and lipoteichoic acid. (Daum et al, Clin Inf. Dis. 54:560 (2012)). However, these vaccines have not been very effective in clinical trials suggesting that vaccine strategies may require a combination of multiple antigens and/or stimulation of the immune response.

*Staphylococcus* is adept at avoiding the host immune response. One aspect of the host's immune response to a staphylococcal infection is to produce antibodies that opsonize the cell surface and lead to complement mediated lysis and/or phagocytosis. *Staphylococcus* species capsular polysaccharides protect against phagocytosis. Cell surface protein A sequesters antibodies by binding to the Fc portion of antibodies inhibiting phagocytosis as well. Some species produce molecules that inhibit complement function and complement mediated lysis. These properties make it challenging to treat *Staphylococcus* infections, especially if the organism is antibiotic resistant. Thus, there is a need for more effective therapeutic agents that can inhibit staphylococcal infections.

BRIEF SUMMARY OF THE DISCLOSURE

According to a first aspect, the present disclosure provides bispecific antigen-binding molecules comprising a first antigen-binding domain (D1) that binds a *Staphylococcus* species target antigen; and a second antigen-binding domain (D2) that binds a complement component. Classical complement components comprise C1q, C1r, C1s, C2, C3, C4, C5, C6, C7, C8, C9, or any fragments thereof (including proteolytic fragments generated by the complement cascade). In embodiments, the bispecific antigen-binding molecule binds to the *Staphylococcus* species target antigen with an $EC_{50}$ of about 10 nM or less. In further embodiments, the bispecific antigen-binding molecule promotes deposition of a complement component on the *Staphylococcus* species with an $EC_{50}$ of about 10 nM or less. In embodiments, the complement component is C1q. In yet other embodiments the C1q is a human C1q. In embodiments, the *Staphylococcus* species is *Staphylococcus aureus* or *Staphylococcus epidermidis*. In embodiments, the *Staphylococcus* species target antigen comprises capsular polysaccharide type 5, capsular polysaccharide type 8, IsdB, IsdA, IsdH, lipoteichoic acid, wall teichoic acid, lipase, V8 lipase, fatty acid modifying enzyme, microbial surface components recognizing adhesive matrix molecules (eg. adhesins, fibrinogen binding molecules, fibronectin binding protein A, fibronectin binding protein B), clumping factor A (clfA), poly-N-acetyl glucosamine (PNAG), or combinations thereof. In embodiments, the *Staphylococcus* species target antigen is iron regulated surface determinant B (IsdB).

According to certain exemplary embodiments, the bispecific antigen-binding molecules bind *Staphylococcus* species target antigen iron regulated surface determinant B (IsdB) and human C1q; such bispecific antigen-binding molecules are also referred to herein as "anti-IsdB× anti-C1q bispecific molecules." The anti-IsdB antigen binding domain of the anti-IsdB× anti-C1q bispecific molecule is useful for targeting microbes that express IsdB (e.g., *Staphylococcus aureus*), and the anti-C1q antigen binding domain of the bispecific molecule is useful for promoting deposition of C1q on the *Staphylococcus* species. The simultaneous binding of antigen binding molecules to a target antigen, such as IsdB, on a microbe and to human C1q facilitates directed killing (cell lysis) of the targeted microbe. The anti-IsdB× anti-C1q bispecific antigen-binding molecules of the disclosure are therefore useful, inter alia, for treating diseases and disorders related to or caused by microbes (e.g., infection, sepsis, and the like).

The bispecific antigen-binding molecules according to this aspect of the present disclosure comprise a first antigen-binding domain (D1) that specifically binds IsdB, and a second antigen-binding domain (D2) that specifically binds human C1q. The present disclosure includes anti-IsdB× anti-C1q bispecific molecules (e.g., bispecific antibodies) wherein each antigen-binding domain comprises a heavy chain variable region (HCVR) paired with a light chain variable region (LCVR). In certain exemplary embodiments of the disclosure, the anti-C1q antigen-binding domain (D2) and the anti-IsdB (D1) antigen-binding domain each comprise different, distinct HCVRs paired with the same or a different LCVR. For example, as illustrated in Example 3 herein, bispecific antibodies were constructed comprising a first antigen-binding domain that comprises an HCVR/LCVR pair derived from an anti-IsdB antibody; and a second antigen-binding domain that comprises an HCVR/LCVR pair derived from an anti-C1q antibody In the exemplary molecules disclosed herein, the pairing of an HCVR from an anti-IsdB antibody with an LCVR having the sequences described herein in Table 3 creates an antigen-binding domain that specifically binds IsdB (but does not bind C1q). In the exemplary molecules disclosed herein, the pairing of an HCVR from an anti-C1q antibody with an LCVR having the sequences described herein in Table 1 creates an antigen-binding domain that specifically binds C1q (but does not bind IsdB).

An antigen-binding molecule, as used in the context of the present disclosure, includes polypeptides that bind a particular antigen (e.g., a target molecule [T] or a portion thereof) with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

An antigen-binding domain includes polypeptides that bind a *Staphylococcus* species target antigen, such as IsdB, (e.g., a target molecule [T] or a portion thereof) with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

An antigen-binding domain includes polypeptides that bind a complement component, such as C1q, with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The present disclosure provides anti-IsdB× anti-C1q bispecific molecules, wherein the first antigen-binding domain that specifically binds IsdB binds to an IsdB comprising an amino acid sequence of amino acids 3 to 574 of SEQ ID NO:169. Species of *Staphylococcus* can have different amino acid sequences of IsdB. Such amino acids sequences are readily obtainable.

In embodiments, the first antigen-binding domain D1 comprises heavy chain variable region (HCVR) CDRs contained within a HCVR comprising an amino acid sequence of SEQ ID. NO: 138 or an amino acid sequence of SEQ ID NO: 154; and light chain variable region (LCVR) CDRs contained within a LCVR region comprising an amino acid sequence of SEQ ID. NO:146 or an amino acid sequence of SEQ ID NO:162. The first antigen-binding domain D1 comprises any of the HCVR amino acid sequences as set forth in Table 3 or Table 6. The first antigen-binding domain D1 may also comprise any of the LCVR amino acid sequences as set forth in Table 3 or Table 6. According to certain embodiments, the first antigen-binding domain D1 comprises a HCVR/LCVR pair comprising amino acid sequences of SEQ ID NOs:138/146, or SEQ ID NOs: 154/162. The present disclosure also provides anti-IsdB× anti-C1q bispecific molecules, wherein the first antigen-binding domain D1 comprises any of the heavy chain CDR1-CDR2-CDR3 amino acid sequences as set forth in Table 3 or Table 6, and/or any of the light chain CDR1-CDR2-CDR3 amino acid sequences as set forth in Table 3 or Table 6.

According to certain embodiments, the present disclosure provides anti-IsdB× anti-C1q bispecific molecules, wherein the first antigen-binding domain D1 comprises a heavy chain variable region (HCVR) comprising an amino acid sequence of SEQ ID NO:138, SEQ ID NO:154, or a substantially similar sequence thereof having at least 90%, at least 95%, at least 98% or at least 99% sequence identity.

The present disclosure also provides anti-IsdB× anti-C1q bispecific molecules, wherein the first antigen-binding domain D1 comprises a light chain variable region (LCVR) comprising an amino acid sequence of SEQ ID NO:146, SEQ ID NO:162, or a substantially similar sequence thereof having at least 90%, at least 95%, at least 98% or at least 99% sequence identity.

The present disclosure also provides anti-IsdB× anti-C1q bispecific molecules, wherein the first antigen-binding domain D1 comprises a heavy chain CDR3 (HCDR3) comprising an amino acid sequence of SEQ ID NO:144, SEQ ID NO:160, or a substantially similar sequence thereto having at least 90%, at least 95%, at least 98% or at least 99% sequence identity; and a light chain CDR3 (LCDR3) comprising an amino acid sequence of SEQ ID NO:152, SEQ ID NO:168, or a substantially similar sequence thereof having at least 90%, at least 95%, at least 98% or at least 99% sequence identity. In certain embodiments, the first antigen-binding domain D1 comprises a HCDR3/LCDR3 pair comprising amino acid sequences of SEQ ID NOs:144/152, 144/168, 160/152, or 160/168.

The present disclosure also provides anti-IsdB× anti-C1q bispecific antigen-binding molecules, wherein the first antigen-binding domain D1 comprises a heavy chain CDR1 (HCDR1) comprising an amino acid sequence of SEQ ID NO:140, SEQ ID NO:156, or a substantially similar sequence thereof having at least 90%, at least 95%, at least 98% or at least 99% sequence identity; a heavy chain CDR2 (HCDR2) comprising an amino acid sequence of SEQ ID NO:142, SEQ ID NO:158, or a substantially similar sequence thereof having at least 90%, at least 95%, at least 98% or at least 99% sequence identity; and a heavy chain CDR3 (HCDR3) comprising an amino acid sequence of SEQ ID NO:144, SEQ ID NO:160, or a substantially similar sequence thereof having at least 90%, at least 95%, at least 98% or at least 99% sequence identity. In embodiments, the first antigen-binding domain D1 comprises a light chain CDR1 (LCDR1) comprising an amino acid sequence of SEQ ID NO:148, SEQ ID NO:164, or a substantially similar sequence thereof having at least 90%, at least 95%, at least 98% or at least 99% sequence identity; a light chain CDR2 (LCDR2) comprising an amino acid sequence of SEQ ID NO:150, SEQ ID NO:166, or a substantially similar sequence thereof having at least 90%, at least 95%, at least 98% or at least 99% sequence identity; and a light chain CDR3 (LCDR3) comprising an amino acid sequence of SEQ ID NO:152, SEQ ID NO:168, or a substantially similar sequence thereof having at least 90%, at least 95%, at least 98% or at least 99% sequence identity.

Certain non-limiting, exemplary anti-IsdB× anti-C1q bispecific antigen-binding molecules of the disclosure include a first antigen-binding domain D1 comprising a set of HCDR1-HCDR2-HCDR3-LCDR1-LCDR2-LCDR3 CDRs, respectively, the set of HCDR1-HCDR2-HCDR3-LCDR1-LCDR2-LCDR3 CDRs comprising amino acid sequences of SEQ ID NOs:140, 142, 144, 148, 150, 152; 140, 142, 144, 164, 166, 168; 156, 158, 160, 148, 150, 152; or 156, 158, 160, 164, 166, 168.

The present disclosure also provides anti-IsdB× anti-C1q bispecific antigen binding molecules, wherein the second antigen-binding domain D2 that specifically binds C1q binds a human C1q comprising an amino acid sequence of SEQ ID NO:170, SEQ ID NO:171, and SEQ ID NO:172. In embodiments, the bispecific antigen-binding molecule blocks the binding of the human C1q to human IgG1-k with an $IC_{50}$ of about 10 nM or less. In other embodiments, the bispecific antigen-binding molecule blocks the binding of the human C1q to human IgM with an $IC_{50}$ of about 50 nM or less. In embodiments, the bispecific antigen binding molecule provides for deposition of C1q with an $EC_{50}$ of about 10 nM or less.

In embodiments, the second antigen-binding domain D2 comprises HCVR CDRs contained within a HCVR comprising an amino acid sequence of SEQ ID. NOs: 2, 10, 18, 26, 34, 42, 50, 58, 66, 74, 82, 90, 98, 106, 114, 122, 130, or a substantially similar sequence thereof having at least 90%, at least 95%, at least 98% or at least 99% sequence identity.

The present disclosure also provides anti-IsdB× anti-C1q bispecific molecules, wherein the second antigen-binding domain D2 comprises LCVR CDRs contained within a LCVR comprising an amino acid sequence of SEQ ID. NO:146, SEQ ID NO:162, or a substantially similar sequence thereof having at least 90%, at least 95%, at least 98% or at least 99% sequence identity.

The present disclosure also provides anti-IsdB× anti-C1q bispecific molecules, wherein the second antigen-binding domain D2 comprises a HCVR and LCVR (HCVR/LCVR) pair comprising amino acid sequences of SEQ ID NOs: 2/146, 10/146, 90/146, 98/146, 106/146, 66/162, 74/162, 82/162, 18/162, 26/162, 34/162, 42/162, 50/162, 58/162, 114/162, 122/162, or 130/162.

The present disclosure also provides anti-IsdB× anti-C1q bispecific molecules, wherein the second antigen-binding domain D2 comprises a heavy chain CDR3 (HCDR3) comprising an amino acid sequence of SEQ ID NO: 8, 16, 24, 32, 40, 48, 56, 64, 72, 80, 88, 96, 104, 112, 120, 128, 136, or a substantially similar sequence thereto having at least 90%, at least 95%, at least 98% or at least 99% sequence identity; and a light chain CDR3 (LCDR3) comprising an amino acid sequence of SEQ ID NO: 152, SEQ ID NO:168, or a substantially similar sequence thereof having at least 90%, at least 95%, at least 98% or at least 99% sequence identity.

In certain embodiments, the second antigen-binding domain D2 comprises a HCDR3/LCDR3 pair comprising amino acid sequences of SEQ ID NOs:8/152, 8/168, 16/152, 16/168, 24/152, 24/168, 32/152, 32/168, 40/152, 40/168, 48/152, 48/168, 56/152, 56/168, 64/152, 64/168, 72/152, 72/168, 80/152, 80/168, 88/152, 88/168, 96/152, 96/168, 104/152, 104/168, 112/152, 112/168, 120/152, 120/168, 128/152, 128/168, 136/152, or 136/168.

The present disclosure also provides anti-IsdB× anti-C1q bispecific antigen-binding molecules, wherein the second antigen-binding domain D2 comprises a heavy chain CDR1 (HCDR1) comprising an amino acid sequence of SEQ ID NO: 4, 12, 20, 28, 36, 44, 52, 60, 68, 76, 84, 92, 100, 108, 116, 124, or 132, or a substantially similar sequence thereof having at least 90%, at least 95%, at least 98% or at least 99% sequence identity; a heavy chain CDR2 (HCDR2) comprising an amino acid sequence of SEQ ID NO: 6, 14, 22, 30, 38, 46, 54, 62, 70, 78, 86, 94, 102, 110, 118, 126, or 134, or a substantially similar sequence thereof having at least 90%, at least 95%, at least 98% or at least 99% sequence identity; and a heavy chain CDR3 (HCDR3) comprising an amino acid sequence of SEQ ID NOs:8, 16, 24, 32, 40, 48, 56, 64, 72, 80, 88, 96, 104, 112, 120, 128, or 136. In embodiments, the second antigen-binding domain D2 comprises a light chain CDR1 (LCDR1) comprising an amino acid sequence of SEQ ID NO:148, SEQ ID NO:164, or a substantially similar sequence thereof having at least 90%, at least 95%, at least 98% or at least 99% sequence identity; a light chain CDR2 (LCDR2) comprising an amino acid sequence of SEQ ID NO:150, SEQ ID NO:166, or a substantially similar sequence thereof having at least 90%, at least 95%, at least 98% or at least 99% sequence identity; and a light chain CDR3 (LCDR3) comprising an amino acid sequence of SEQ ID NO:152, SEQ ID NO:168, or a substantially similar sequence thereof having at least 90%, at least 95%, at least 98% or at least 99% sequence identity.

Certain non-limiting, exemplary anti-IsdB× anti-C1q bispecific antigen-binding molecules of the disclosure comprise a second antigen-binding domain D2 comprising a set of HCDR1-HCDR2-HCDR3-LCDR1-LCDR2-LCDR3 CDRs, respectively, the set of HCDR1-HCDR2-HCDR3-LCDR1-LCDR2-LCDR3 CDRs comprising amino acid sequences of SEQ ID NOs: 4, 6, 8, 148, 150, 152; 12, 14, 16, 148, 150, 152; 92, 94, 96, 148, 150, 152; 100, 102, 104, 148, 150, 152; 108, 110, 112, 148, 150, 152; 20, 22, 24, 148, 150, 152; 28, 30, 32, 148, 150, 152; 36, 38, 40, 148, 150, 152; 44, 46, 48, 148, 150, 152; 52, 54, 56, 148, 150, 152; 60, 62, 64, 148, 150, 152; 68, 70, 72, 148, 150, 152; 76, 78, 80, 148, 150, 152; 84, 86, 88, 148, 150, 152; 116, 118, 120, 148, 150, 152; 124, 126, 128, 148, 150, 152; 132, 134, 136, 148, 150, 152; 4, 6, 8, 164, 166, 168; 12, 14, 16, 164, 166, 168; 92, 94, 96, 164, 166, 168; 100, 102, 104, 164, 166, 168; 108, 110, 112, 164, 166, 168; 20, 22, 24, 164, 166, 168; 28, 30, 32, 164, 166, 168; 36, 38, 40, 164, 166, 168; 44, 46, 48, 164, 166, 168; 52, 54, 56, 164, 166, 168; 60, 62, 64, 164, 166, 168; 68, 70, 72, 164, 166, 168; 76, 78, 80, 164, 166, 168; 84, 86, 88, 164, 166, 168; 116, 118, 120, 164, 166, 168; 124, 126, 128, 164, 166, 168; or 132, 134, 136, 164, 166, 168.

In a related embodiment, the disclosure includes anti-IsdB× anti-C1q bispecific antigen-binding molecules, wherein the second antigen-binding domain D2 comprises the heavy and light chain CDRs contained within a pair of heavy and light chain variable region (HCVR/LCVR) sequences, the HCVR/LCVR pair comprising amino acid sequences of SEQ ID NOs: 2/146, 10/146, 90/146, 98/146, 106/146, 66/162, 74/162, 82/162, 18/162, 26/162, 34/162, 42/162, 50/162, 58/162, 114/162, 122/162, or 130/162.

In embodiments, the isolated bispecific antigen-binding molecule comprises a first antigen-binding domain D1 that comprises HCVR CDRs comprising an amino acid sequence of SEQ ID NOs: 140, 142, 144, and LCVR CDRs comprising an amino acid sequence of SEQ ID NOs: 148, 150, 152; and a second antigen-binding domain D2 that comprises HCVR CDRs comprising an amino acid sequence of SEQ ID NOs:4, 6, 8, and LCVR CDRs comprising an amino acid sequence of SEQ ID NOs:148, 150, 152. In other embodiments, the isolated bispecific antigen-binding molecule comprises a first antigen-binding domain D1 that comprises HCVR CDRs comprising an amino acid sequence of SEQ ID NOs:140, 142, 144, and LCVR CDRs comprising an amino acid sequence of SEQ ID NOs: 148, 150, 152; and a second antigen binding domain D2 that comprises HCVR CDRs comprising an amino acid sequence of SEQ ID NOs:108, 110, 112, and LCVR CDRs comprising an amino acid sequence of SEQ ID NOs: 148, 150, 152. In further embodiments, the isolated bispecific antigen-binding molecule comprises a first antigen-binding domain that comprises a HCVR/LCVR pair, the HCVR/LCVR pair comprising amino acid sequences of SEQ ID NOs:138/146, or SEQ ID NOs:154/162; and the second antigen-binding domain comprises a HCVR/LCVR pair, the HCVR/LCVR pair comprising amino acid sequences of SEQ ID NOs:2/146, 10/146, 90/146, 98/146, 106/146, 66/162, 74/162, 82/162, 18/162, 26/162, 34/162, 42/162, 50/162, 58/162, 114/162, 122/162, or 130/162.

In another aspect, the present disclosure provides nucleic acid molecules encoding any of the HCVR, LCVR or CDR sequences of the anti-IsdB× anti-C1q bispecific antigen-binding molecules disclosed herein, including nucleic acid molecules comprising the polynucleotide sequences as set forth in Tables 2 and 4 herein, as well as nucleic acid molecules comprising two or more of the polynucleotide sequences as set forth in Tables 2 and 4 in any functional combination or arrangement thereof. Recombinant expression vectors carrying the nucleic acids of the disclosure, and host cells into which such vectors have been introduced, are also encompassed by the disclosure, as are methods of producing the antibodies by culturing the host cells under conditions permitting production of the antibodies, and recovering the antibodies produced.

The present disclosure includes anti-IsdB× anti-C1q bispecific antigen-binding molecules wherein any of the aforementioned antigen-binding domains that specifically bind C1q are combined, connected or otherwise associated with any of the aforementioned antigen-binding domains that specifically bind IsdB to form a bispecific antigen-binding molecule that binds C1q and IsdB. The antigen-binding domains can be combined in a number of different ways including single chain Fv, dual affinity retargeting proteins, tandem diabodies, knob and hole pairings, charge pairings, cross Mab, double variable domain Ig, s-Fab, and Fv-Fc as described herein.

The present disclosure includes anti-IsdB× anti-C1q bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC)(eg. adding a terminal galactose enhances ADCC).

In another aspect, the disclosure provides a pharmaceutical composition comprising an anti-IsdB× anti-C1q bispecific antigen-binding molecule as disclosed herein and a pharmaceutically acceptable carrier. In a related aspect, the disclosure features a composition, which is a combination of an anti-IsdB× anti-C1q bispecific antigen-binding molecule and a second therapeutic agent. In one embodiment, the second therapeutic agent is any agent that is advantageously combined with an anti-IsdB× anti-C1q bispecific antigen-binding molecule. Exemplary agents that may be advantageously combined with an anti-IsdB× anti-C1q bispecific antigen-binding molecule include an antibiotic, an antibody that binds a *Staphylococcus* antigen, an antibody that binds a *Staphylococcus* toxin, an antibody that binds human or cynomolgus C1q, a vaccine specific for *Staphylococcus* species, and an antibody drug conjugate (e.g. a bispecific antibody combined with an antibiotic).

In yet another aspect, the disclosure provides therapeutic methods for inhibiting the growth of a *Staphylococcus* species in a subject comprising administering the isolated bispecific antigen-binding molecule as described herein or a pharmaceutical composition comprising the bispecific antigen binding molecule to the subject. In embodiments, the method is a method of treating an infection with a *Staphylococcus* species in a subject. In some embodiments, the method is for treating a subject that has a disease or disorder caused by a *Staphylococcus* species, wherein the disease or disorder is a skin infection, cellulitis, pneumonia, meningitis, urinary tract infection, toxic shock syndrome, endocarditis, pericarditis, osteomyelitis, bacteremia, or sepsis. In some embodiments, the method is for treating a subject who has undergone, or who is planning on undergoing a surgical procedure, wherein the subject is at risk of acquiring a *Staphylococcus* infection. In some embodiments, the surgical procedure involves implantation of a prosthetic, including a prosthetic limb, such as an arm or a leg, or a hip replacement. In some embodiments, the prosthetic is a cosmetic prosthetic, including an ocular prosthetic, silicone hands, fingers, toes, breasts, or a facial implant.

In embodiments, the method is a method of targeting/killing *Staphylococcus* cells expressing a target antigen, such as IsdB, using an anti-IsdB× anti-C1q bispecific antigen-binding molecule of the disclosure, wherein the therapeutic methods comprise administering a therapeutically effective amount of a pharmaceutical composition comprising an anti-IsdB/anti-C1q bispecific antigen-binding molecule of the disclosure to a subject in need thereof.

The present disclosure also includes the use of an anti-IsdB× anti-C1q bispecific antigen-binding molecule of the disclosure in the manufacture of a medicament for the treatment of a disease or disorder related to or caused by a *Staphylococcus*.

Other embodiments will become apparent from a review of the ensuing detailed description.

DETAILED DESCRIPTION

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, the preferred methods and materials are now described. All patents, applications and non-patent publications mentioned in this specification are incorporated herein by reference in their entireties.

Definitions

As used herein, "an antibody that binds a complement component" or an "anti-complement component antibody" includes antibodies and antigen-binding fragments thereof that specifically recognize a complement component. In one embodiment, the antigen binding molecules of the disclosure bind the complement component C1q. An exemplary C1q protein has the amino acid sequence of SEQ ID NO:170, SEQ ID NO:171, and SEQ ID NO:172.

As used herein, the expression "an antibody that binds a complement component", an "anti-complement component antibody", or an "anti-C1q antibody" includes both monovalent antibodies with a single specificity, as well as bispecific antibodies comprising a first arm that binds IsdB and a second arm that binds a C1q, wherein the anti-C1q arm comprises any of the HCVR/LCVR or CDR sequences as set forth in Table 1 or Table 6 herein. Examples of anti-C1q bispecific antibodies are described elsewhere herein.

The expression "C1q," as used herein, refers to a complement component C1q that is a member of the complement cascade. Human complement C1q is a hexamer that comprises three unique subunits: A(29 kDa); B(26 kDa); and C(22 kDa). An exemplary sequence of subunit A is found at amino acids 1-245 of accession number NP_057075 and shown in SEQ ID NO:170. An exemplary sequence of subunit B is found at amino acids 1-253 of accession number NP_000482 and shown in SEQ ID NO:171. An exemplary sequence of subunit C is found at amino acids 1-245 of accession number NP_758957 and shown in SEQ ID NO:172. In embodiments, C1q is a human C1q.

As used herein, "an antibody that binds C1q" or an "anti-C1q antibody" includes antibodies and antigen-binding fragments thereof that specifically recognize a single C1q subunit (e.g., component A, B, or C), as well as antibodies and antigen-binding fragments thereof that specifically recognize a multimer such as a trimer or a hexamer. C1q includes natural C1q proteins as well as recombinant C1q protein, or variants thereof.

As used herein, the expression "an antibody that binds C1q" or "anti-C1q antibody" includes both monovalent antibodies with a single specificity, as well as bispecific antibodies comprising a first arm that binds a Staphylococcus species target antigen, and a second arm that binds a C1q, wherein the anti-C1q arm comprises any of the HCVR/LCVR or CDR sequences as set forth in Table 1 or Table 6 herein. Examples of anti-C1q bispecific antibodies are described elsewhere herein.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In embodiments, an antigen binding molecule comprises one or more antigen binding domains. The term "antigen-binding molecule" includes antibodies and antigen-binding fragments of antibodies, including, e.g., bispecific antibodies.

The expression "*Staphylococcus* species" as used herein, refers to a species of the microbe *Staphylococcus*. In embodiments, the *Staphylococcus* species is a species that is associated with infections in humans including *Staphylococcus epidermidis, Staphylococcus aureus, Staphylococcus lugdunensis*, and/or *Staphylococcus saprophiticus.*

As used herein, "target antigen" refers to an antigen found in or on a *Staphylococcus* species. Target antigens include those antigens found on the cell surface of the *Staphylococcus* species. Exemplary target antigens include capsular polysaccharide type 5, capsular polysaccharide type 8, IsdB, IsdA, IsdH, lipoteichoic acid, wall teichoic acid, clumping factor A (clfA), poly-N-acetyl glucosamine (PNAG), lipase, V8 lipase, fatty acid modifying enzyme, microbial surface components recognizing adhesive matrix molecules (eg. adhesins, fibrinogen binding molecules, fibronectin binding protein A, fibronectin binding protein B), or combinations thereof.

As used herein, "an antibody that binds a *Staphylococcus* species target antigen" or an "anti-*Staphylococcus* species target antibody" includes antibodies and antigen-binding fragments thereof that specifically recognize a target antigen on the cell surface of, or in a *Staphylococcus* species. In one embodiment, the antigen binding molecules of the disclosure bind the target antigen referred to as "iron regulated surface protein B", or "IsdB". An exemplary IsdB protein has the amino acid sequence of amino acids 3 to 574 of SEQ ID NO:169.

As used herein, the expression "an antibody that binds a *Staphylococcus* species target antigen", an "anti-*Staphylococcus* species target antibody", or an "anti-IsdB antibody" includes both monovalent antibodies with a single specificity, as well as bispecific antibodies comprising a first arm that binds IsdB and a second arm that binds a C1q, wherein the anti-IsdB arm comprises any of the HCVR/LCVR or CDR sequences as set forth in Table 3 or Table 6 herein. Examples of anti-IsdB bispecific antibodies are described elsewhere herein. In one embodiment, a bispecific antibody comprising one arm that binds IsdB and one arm that binds C1q comprises the following full length amino acid sequences: SEQ ID NO: 173 comprises the full length amino acid sequence of the heavy chain (HC) of an antibody that binds C1q; SEQ D NO: 174 comprises the full length amino acid sequence of the heavy chain of an antibody that binds IsdB; and SEQ ID NO: 175 comprises the full length amino acid sequence of the light chain (LC) of a bispecific antibody that binds IsdB and C1q. In one embodiment, an antibody having these full length sequences is designated as H1H20631D.

The term "antibody", as used herein, means any antigen-binding molecule or molecular complex comprising at least one complementarity determining region (CDR) that specifically binds to or interacts with a particular antigen (e.g., C1q). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-C1q antibody (or antigen-binding portion thereof) may be identical to the human germline sequences, or may be naturally or artificially modified. In different embodiments of the disclosure, the FRs of the anti-IsdB antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen binding domain" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., a complement component or a *Staphylococcus* species target antigen).

The term "specifically binds" or the like, as used herein, means that the antigen-binding domain forms a complex with a particular antigen characterized by a dissociation constant ($K_D$) of 25 nM or less. Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding molecule, as used in the context of the present disclosure, includes polypeptides that bind a particular antigen (e.g., a target molecule [T] or a portion thereof) with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; (vii) an antigen binding domain, and (viii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may comprise or consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos.

5,500,362 and 5,821,337, and Clynes et al. (1998) Proc. Natl. Acad. Sci. (USA) 95:652-656).

In certain embodiments of the disclosure, the anti-C1q and/or anti-IsdB antibodies of the disclosure (monospecific or bispecific) are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term includes antibodies recombinantly produced in a non-human mammal, or in cells of a non-human mammal. The term is not intended to include antibodies isolated from or generated in a human subject.

The antibodies of the disclosure may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form.

The antibodies of the disclosure may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present disclosure also includes one-arm antibodies that bind C1q or IsdB. As used herein, a "one-arm antibody" means an antigen-binding molecule comprising a single antibody heavy chain and a single antibody light chain. The one-arm antibodies of the present disclosure may comprise any of the HCVR/LCVR or CDR amino acid sequences as set forth in Table 1 or Table 3 herein.

The anti-C1q, anti-IsdB, or bispecific antigen binding molecules disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antigen binding molecules, antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antigen binding molecules, antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antigen binding molecules, antibodies and antigen-binding fragments of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen binding molecules, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antigen binding molecules, antibodies and antigen-binding fragments obtained in this general manner are encompassed within the present disclosure.

The present disclosure also includes anti-C1q, anti-IsdB, or bispecific antigen binding molecules comprising variants of any of the HCVR, LCVR, and/or CDR amino acid sequences disclosed herein having one or more conservative substitutions. For example, the present disclosure includes anti-C1q, anti-IsdB, or bispecific antigen binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 or Table 3 herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions, which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-Complement Component Antibodies or Antigen Binding Fragments Thereof

According to one aspect of the present disclosure, anti-complement component antibodies are provided. Complement components comprise C1q, C1r, C1s, C2, C3, C4, C5, C6, C7, C8, C9, or any fragments thereof (including proteolytic fragments generated by the complement cascade). In embodiments, antibodies that bind C1q (e.g. monospecific anti-C1q antibodies) are provided. In embodiments, C1q is a human C1q. A human C1q comprises an amino acid sequence of SEQ ID NO:170, SEQ ID NO:171, and/or SEQ ID NO:172. The antibodies according to this aspect of the disclosure are useful, inter alia, for targeting C1q and complement activation to specific targets. The anti-C1q antibodies of the disclosure, or antigen-binding portions thereof, may be included in a bispecific antigen-binding molecule that directs C1q-mediated complement activation to specific target cell types, such as *Staphylococcus* species.

In embodiments, the anti-C1q antibodies are selected that inhibit C1q binding to immunoglobulin molecules, inhibit hemolysis, and/or complement dependent cytotoxicity. In embodiments, the bispecific antigen-binding molecule blocks the binding of the human C1q to human IgG1-k with an $IC_{50}$ of about 10 nM or less. In other embodiments, the bispecific antigen binding molecule blocks the binding of the human C1q to human IgM with an $IC_{50}$ of about 50 nM or less. In embodiments, the bispecific antigen binding molecule inhibits complement dependent cytotoxicity with an $IC_{50}$ of about 100 nM or less. In yet other embodiments, the bispecific antigen binding molecule provides for deposition of human C1q with an $EC_{50}$ of about 10 nM or less. In certain embodiments, an antigen binding molecule of the invention may not exhibit one or more of the following: blocking or inhibition of IgG binding, or hemolysis, or complement dependent cytotoxicity, as described herein, but may still be effective for preventing a *Staphylococcus* infection, or for treating an existing infection in a subject.

Exemplary anti-C1q antibodies of the present disclosure are listed in Tables 1 and 2 herein. Table 1 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-C1q antibodies. Table 2 sets forth the sequence identifiers of the nucleic acid molecules encoding the HCVRs, LCVRs, HCDR1, HCDR2 HCDR3, LCDR1, LCDR2 and LCDR3 of the exemplary anti-C1q antibodies.

The present disclosure provides antibodies, or antigen-binding fragments thereof that bind human C1q, comprising heavy chain variable region CDRs contained within a HCVR comprising an amino acid sequence selected from any of the HCVR amino acid sequences listed in Table 1, or a substantially similar sequence thereof having at least 90%, at least 95%, at least 98% or at least 99% sequence identity thereto.

The present disclosure also provides anti-C1q antibodies, or antigen-binding fragments thereof, comprising light chain variable region CDRs contained within a LCVR comprising an amino acid sequence selected from any of the LCVR amino acid sequences listed in Table 1, or a substantially similar sequence thereof having at least 90%, at least 95%, at least 98% or at least 99% sequence identity thereto.

The present disclosure also provides anti-C1q antibodies, or antigen-binding fragments thereof, comprising an HCVR and an LCVR pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR pair contained within any of the exemplary anti-C1q antibodies listed in Table 1. In certain embodiments, an anti-C1q antibody comprises a HCVR/LCVR pair, the HCVR/LCVR pair comprising amino acid sequence of SEQ ID NOs: 2/146 (e.g., H1xH17736P2); SEQ ID NOs: 10/146 (e.g., H1xH17738P2), SEQ ID NOs: 18/162 (e.g., H1xH17751P2), SEQ ID NOs: 34/162 (e.g., H1xH17758P2), SEQ ID NOs: 66/162 (e.g., H1xH17773P2), 90/146 (e.g., H1xH18392P2); 98/146 (e.g., H1xH18394P2); 106/146 (e.g., H1xH18395P2); 74/162 (e.g., H1xH17779P2); 82/162 (e.g., H1xH17781P2); 26/162 (e.g., H1xH17756P2); 42/162 (e.g., H1xH17760P2); 50/162 (e.g., H1xH17763P2); 58/162 (e.g., H1xH17769P2); 114/162 (e.g., H1xH18400P2); 122/162 (e.g., H1xH18411P2); or 130/162 (e.g., H1xH18412P2).

The present disclosure also provides antibodies, or antigen-binding fragments thereof, that bind to human C1q comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, that bind to human C1q comprising an HCDR3 and an LCDR3 pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 pair contained within any of the exemplary anti-C1q antibodies listed in Table 1. In certain embodiments, the HCDR3/LCDR3 pair comprises amino acid sequences of SEQ ID NOs: 16/152 (e.g., H1xH17738P2), SEQ ID NOs: 24/168 (e.g., H1xH17751P2), SEQ ID NOs: 40/168 (e.g., H1xH17758P2), SEQ ID NOs: 72/168 (e.g., H1xH17773P2), SEQ ID NOs: 8/152 (e.g., H1xH17736P2); 96/152 (e.g., H1xH18392P2); 104/152 (e.g., H1xH18394P2); 112/152 (e.g., H1xH18395P2); 80/168 (e.g., H1xH17779P2); 88/168 (e.g., H1xH17781P2); 32/168 (e.g., H1xH17756P2); 48/168 (e.g., H1xH17760P2); 56/168 (e.g., H1xH17763P2); 64/168 (e.g., H1xH17769P2); 120/168 (e.g., H1xH18400P2); 128/168 (e.g., H1xH18411P2); or 136/168 (e.g., H1xH18412P2).

The present disclosure also provides antibodies, or antigen-binding fragments thereof, that bind to human C1q comprising a set of six CDRs (i.e., HCDR1-HCDR2-

HCDR3-LCDR1-LCDR2-LCDR3) contained within any of the exemplary anti-C1q antibodies listed in Table 1. In certain embodiments, the HCDR1-HCDR2-HCDR3-LCDR1-LCDR2-LCDR3 set comprises amino acid sequences of SEQ ID NOs: 4, 6, 8, 148, 150, 152 (e.g., H1xH17736P2); 92, 94, 96, 148, 150, 152 (e.g., H1xH18392P2); 100, 102, 104, 148, 150, 152 (e.g., H1xH18394P2); 108, 110, 112, 148, 150, 152 (e.g., H1xH18395P2); 76, 78, 80, 164, 166, 168 (e.g., H1xH17779P2); 84, 86, 88, 164, 166, 168 (e.g., H1xH17781P2); 28, 30, 32, 164, 166, 168 (e.g., H1xH17756P2); 44, 46, 48, 164, 166, 168 (e.g., H1xH17760P2); 52, 54, 56, 164, 166, 168 (e.g., H1xH17763P2); 60, 62, 64, 164, 166, 168 (e.g., H1xH17769P2); 116, 118, 120, 164, 166, 168 (e.g., H1xH18400P2); 124, 126, 128, 164, 166, 168 (e.g., H1xH18411P2);); SEQ ID NOs: 12, 14, 16, 18, 150, 152 (e.g., H1xH17738P2), SEQ ID NOs: 20, 22, 24, 164, 166, 168 (e.g., H1xH17751P2), SEQ ID NOs: 36, 38, 40, 164, 166, 168 (e.g., H1xH17758P2), SEQ ID NOs: 68, 70, 72, 164, 166, 168 (e.g., H1xH17773P2), or 132, 134, 136, 164, 166, 168 (e.g., H1xH18412P2).

In a related embodiment, the present disclosure provides antibodies, or antigen-binding fragments thereof that bind to human C1q, comprising a set of six CDRs (i.e., HCDR1-HCDR2-HCDR3-LCDR1-LCDR2-LCDR3) contained within an HCVR/LCVR pair as defined by any of the exemplary anti-C1q antibodies listed in Table 1. For example, the present disclosure includes antibodies, or antigen-binding fragments thereof, comprising the HCDR1-HCDR2-HCDR3-LCDR1-LCDR2-LCDR3 set contained within an HCVR/LCVR pair comprising amino acid sequences of SEQ ID NOs: 2/146 (e.g., H1xH17736P2);); SEQ ID NOs: 10/146 (e.g., H1xH17738P2), SEQ ID NOs: 18/162 (e.g., H1xH17751P2), SEQ ID NOs: 34/162 (e.g., H1xH17758P2), SEQ ID NOs: 66/162 (e.g., H1xH17773P2), 90/146 (e.g., H1H20633D); 98/146 (e.g., H1xH18392P2); 106/146 (e.g., H1xH18395P2); 74/162 (e.g., H1xH17779P2); 82/162 (e.g., H1xH17781P2); 26/162 (e.g., H1xH17756P2); 42/162 (e.g., H1xH17760P2); 50/162 (e.g., H1xH17763P2); 58/162 (e.g., H1xH17769P2); 114/162 (e.g., H1xH18400P2); 122/162 (e.g., H1xH18411P2); or 130/162 (e.g., H1xH18412P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present disclosure also provides nucleic acid molecules encoding anti-C1q antibodies or portions thereof. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs (i.e., HCDR1-HCDR2-HCDR3), wherein the HCDR1-HCDR2-HCDR3 set is as defined by any of the exemplary anti-C1q antibodies listed in Table 1.

The present disclosure also provides nucleic acid molecules encoding an LCVR, wherein the LCVR comprises a set of three CDRs (i.e., LCDR1-LCDR2-LCDR3), wherein the LCDR1-LCDR2-LCDR3 set is as defined by any of the exemplary anti-C1q antibodies listed in Table 1.

The present disclosure also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-C1q antibody listed in Table 1.

The present disclosure also provides recombinant expression vectors capable of expressing a polypeptide comprising a heavy or light chain variable region of an anti-C1q antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes anti-C1q antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Anti-*Staphylococcus* Species Target Antigen Antibodies or Antigen Binding Fragments Thereof In another aspect, the present disclosure provides antibodies and antigen-binding fragments thereof that bind a *Staphylococcus* species target antigen (e.g. a monospecific antibody to a *Staphylococcus* species target antigen). In embodiments, the *Staphylococcus* species is a species that causes an infection in humans. In embodiments, the *Staphylococcus* species comprises *Staphylococcus epidermidis, Staphylococcus aureus, Staphylococcus lugdunensis*, and/or *Staphylococcus saprophiticus*. In embodiments, the *Staphylococcus* species target antigen comprises capsular polysaccharide type 5, capsular polysaccharide type 8, IsdB, IsdA, IsdH, lipoteichoic acid, wall teichoic acid, clumping factor A (clfA), poly-N-acetyl glucosamine (PNAG), lipase, V8 lipase, fatty acid modifying enzyme, microbial surface components recognizing adhesive matrix molecules (eg. adhesins, fibrinogen binding molecules, fibronectin binding protein A, fibronectin binding protein B), protein A or combinations thereof.

In one embodiment, the antibody or antigen binding fragment thereof specifically binds IsdB. In one embodiment, the antibody or antigen binding fragment thereof that specifically binds IsdB binds to an IsdB comprising an amino acid sequence of amino acids 3 to 574 of SEQ ID NO:169. The anti-IsdB antibodies of the disclosure, or antigen-binding portions thereof, may be included in a bispecific antigen-binding molecule that binds specific target cell types such as infectious agents. In embodiments, the bispecific antigen-binding molecule binds to the *Staphylococcus* species with an $IC_{50}$ of about 10 nM or less.

Exemplary anti-IsdB antibodies of the present disclosure are listed in Tables 3 and 4. Table 3 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-IsdB antibodies. Table 4 sets forth the sequence identifiers of the nucleic acid molecules encoding the HCVRs, LCVRs, HCDR1, HCDR2 HCDR3, LCDR1, LCDR2 and LCDR3 of the exemplary anti-IsdB antibodies The present disclosure provides antibodies, or antigen-binding fragments thereof that bind IsdB comprising heavy chain variable region (HCVR) CDRs contained within a HCVR comprising an amino acid sequence of SEQ ID. NO: 138, an amino acid sequence of SEQ ID NO: 154, or a substantially similar sequence thereof having at least 90%, at least 95%, at least 98% or at least 99% sequence identity thereto; and light chain variable region (LCVR) CDRs contained within a LCVR region comprising an amino acid sequence of SEQ ID. NO:146, an amino acid sequence of SEQ ID NO:162, or a substantially similar sequence thereof having at least 90%, at least 95%, at least 98% or at least 99% sequence identity thereto.

The present disclosure also provides antibodies, or antigen-binding fragments thereof, comprising an HCVR and an LCVR pair (HCVR/LCVR) comprising any of the HCVR amino acid sequences listed in Table 3 paired with any of the LCVR amino acid sequences listed in Table 3. According to certain embodiments, the present disclosure provides antibodies, or antigen-binding fragments thereof, comprising an HCVR/LCVR pair contained within any of the exemplary anti-IsdB antibodies listed in Table 3. In certain embodiments, the HCVR/LCVR pair comprises amino acid sequences of SEQ ID NOs:138/146, or SEQ ID NOs: 154/162.

The present disclosure also provides antibodies, or antigen-binding fragments thereof, that bind to IsdB comprising a heavy chain CDR1 (HCDR1) comprising an amino acid sequence selected from any of the HCDR1 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to human IsdB comprising a heavy chain CDR2 (HCDR2) comprising an amino acid sequence selected from any of the HCDR2 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to IsdB comprising a heavy chain CDR3 (HCDR3) comprising an amino acid sequence selected from any of the HCDR3 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to IsdB comprising a light chain CDR1 (LCDR1) comprising an amino acid sequence selected from any of the LCDR1 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to IsdB comprising a light chain CDR2 (LCDR2) comprising an amino acid sequence selected from any of the LCDR2 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to IsdB comprising a light chain CDR3 (LCDR3) comprising an amino acid sequence selected from any of the LCDR3 amino acid sequences listed in Table 3, or a substantially similar sequence thereof having at least 90%, at least 95%, at least 98% or at least 99% sequence identity.

The present disclosure also provides antibodies, or antigen-binding fragments thereof, that bind to IsdB comprising an HCDR3 and an LCDR3 pair (HCDR3/LCDR3) comprising any of the HCDR3 amino acid sequences listed in Table 3 paired with any of the LCDR3 amino acid sequences listed in Table 3. According to certain embodiments, the present disclosure provides antibodies, or antigen-binding fragments thereof, comprising an HCDR3/LCDR3 pair contained within any of the exemplary IsdB antibodies listed in Table 3. In certain embodiments, the first antigen-binding domain that specifically binds IsdB comprises a HCDR3/LCDR3 pair comprising amino acid sequences of SEQ ID NOs:144/152, 144/168, 160/152, or 160/168.

The present disclosure also provides antibodies, or antigen-binding fragments thereof, that bind to IsdB comprising a heavy chain CDR1 (HCDR1) comprising an amino acid sequence of SEQ ID NO:140, SEQ ID NO:156, or a substantially similar sequence thereof having at least 90%, at least 95%, at least 98% or at least 99% sequence identity; a heavy chain CDR2 (HCDR2) comprising an amino acid sequence of SEQ ID NO:142, SEQ ID NO:158, or a substantially similar sequence thereof having at least 90%, at least 95%, at least 98% or at least 99% sequence identity; and a heavy chain CDR3 (HCDR3) comprising an amino acid sequence of SEQ ID NO:144, SEQ ID NO:160, or a substantially similar sequence thereof having at least 90%, at least 95%, at least 98% or at least 99% sequence identity. In embodiments, the first antigen-binding domain that specifically binds IsdB comprises a light chain CDR1 (LCDR1) comprising an amino acid sequence of SEQ ID NO:148, SEQ ID NO:164, or a substantially similar sequence thereof having at least 90%, at least 95%, at least 98% or at least 99% sequence identity; a light chain CDR2 (LCDR2) comprising an amino acid sequence of SEQ ID NO:150, SEQ ID NO:166, or a substantially similar sequence thereof having at least 90%, at least 95%, at least 98% or at least 99% sequence identity; and a light chain CDR3 (LCDR3) comprising an amino acid sequence of SEQ ID NO:152, SEQ ID NO:168, or a substantially similar sequence thereof having at least 90%, at least 95%, at least 98% or at least 99% sequence identity.

Certain non-limiting, exemplary antibodies, or antigen-binding fragments thereof, that bind to IsdB comprise a set of six CDRs HCDR1-HCDR2-HCDR3-LCDR1-LCDR2-LCDR3, respectively, the set comprising amino acid sequences of SEQ ID NOs: 140, 142, 144, 148, 150, 152; 140, 142, 144, 164, 166, 168; 156, 158, 160, 148, 150, 152; or 156, 158, 160, 164, 166, 168.

In another aspect, the present disclosure provides nucleic acid molecules encoding any of the HCVR, LCVR or CDR sequences of the antibodies, or antigen-binding fragments thereof, that bind to IsdB including nucleic acid molecules comprising the polynucleotide sequences as set forth in Table 4 herein, as well as nucleic acid molecules comprising two or more of the polynucleotide sequences as set forth in Tables 2 and 4 in any functional combination or arrangement thereof. Recombinant expression vectors carrying the nucleic acids of the disclosure, and host cells into which such vectors have been introduced, are also encompassed by the disclosure, as are methods of producing the antibodies by culturing the host cells under conditions permitting production of the antibodies, and recovering the antibodies produced.

The present disclosure also provides nucleic acid molecules encoding anti-IsdB antibodies or portions thereof. For example, the present disclosure provides nucleic acid molecules encoding any of the HCVR amino acid sequences listed in Table 3; in certain embodiments the nucleic acid molecule comprises a polynucleotide sequence selected from any of the HCVR nucleic acid sequences listed in Table 4, or a substantially similar sequence thereof having at least 90%, at least 95%, at least 98% or at least 99% sequence identity thereto.

The present disclosure also provides nucleic acid molecules encoding any of the LCVR amino acid sequences listed in Table 3; in certain embodiments the nucleic acid molecule comprises a polynucleotide sequence selected from any of the LCVR nucleic acid sequences listed in Table 4, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 3; in certain embodiments the nucleic acid molecule comprises a polynucleotide sequence selected from any of the HCDR1 nucleic acid sequences listed in Table 4, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 3; in certain embodiments the nucleic acid molecule comprises a polynucleotide sequence selected from any of the HCDR2 nucleic acid sequences listed in Table 4, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 3; in certain embodiments the nucleic acid molecule comprises a polynucleotide sequence selected from any of the HCDR3 nucleic acid sequences listed in Table 4, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 3; in certain embodiments the nucleic acid molecule comprises a polynucleotide sequence selected from any of the LCDR1 nucleic acid sequences listed in Table 4, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 3; in certain embodiments the nucleic acid molecule comprises a polynucleotide sequence selected from any of the LCDR2 nucleic acid sequences listed in Table 4, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 3; in certain embodiments the nucleic acid molecule comprises a polynucleotide sequence selected from any of the LCDR3 nucleic acid sequences listed in Table 4, or a substantially similar sequence thereof having at least 90%, at least 95%, at least 98% or at least 99% sequence identity thereto.

The present disclosure also provides nucleic acid molecules encoding an HCVR, wherein the HCVR comprises a set of three CDRs (i.e., HCDR1-HCDR2-HCDR3), wherein the HCDR1-HCDR2-HCDR3 set is as defined by any of the exemplary anti-IsdB antibodies listed in Table 3.

The present disclosure also provides nucleic acid molecules encoding an LCVR, wherein the LCVR comprises a set of three CDRs (i.e., LCDR1-LCDR2-LCDR3), wherein the LCDR1-LCDR2-LCDR3 set is as defined by any of the exemplary anti-IsdB antibodies listed in Table 3.

The present disclosure also provides nucleic acid molecules encoding both an HCVR and an LCVR, wherein the HCVR comprises an amino acid sequence of any of the HCVR amino acid sequences listed in Table 3, and wherein the LCVR comprises an amino acid sequence of any of the LCVR amino acid sequences listed in Table 3. In certain embodiments, the nucleic acid molecule comprises a polynucleotide sequence selected from any of the HCVR nucleic acid sequences listed in Table 4, or a substantially similar sequence thereof having at least 90%, at least 95%, at least 98% or at least 99% sequence identity thereto, and a polynucleotide sequence selected from any of the LCVR nucleic acid sequences listed in Table 4, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-IsdB antibody listed in Table 3.

The present disclosure also provides recombinant expression vectors capable of expressing a polypeptide comprising a heavy or light chain variable region of an anti-IsdB antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 3. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes anti-IsdB antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Bispecific Antigen-Binding Molecules

The bispecific antigen-binding molecules of the present disclosure comprise two separate antigen-binding domains (D1 and D2). One antigen-binding domain (D1) specifically binds to a *Staphylococcus* species target antigen, e.g. IsdB, and the second antigen-binding domain (D2) binds to a complement component, e.g. C1q.

In embodiments, the first antigen binding domain binds a *Staphylococcus* species target antigen (e.g. a monospecific antibody to a *Staphylococcus* species target antigen). In embodiments, the *Staphylococcus* species is a species that causes an infection in humans. In embodiments, the *Staphylococcus* species comprises *Staphylococcus epidermidis, Staphylococcus aureus, Staphylococcus lugdunensis,* and/or *Staphylococcus saprophiticus*. In embodiments, the *Staphylococcus* species target antigen comprises capsular polysaccharide type 5, capsular polysaccharide type 8, IsdB, IsdA, IsdH, lipoteichoic acid, wall teichoic acid, clumping factor A (clfA), poly-N-acetyl glucosamine (PNAG), lipase, V8 lipase, fatty acid modifying enzyme, microbial surface components recognizing adhesive matrix molecules (eg. adhesins, fibrinogen binding molecules, fibronectin binding protein A, fibronectin binding protein B), protein A, or combinations thereof. In certain embodiments, the *Staphylococcus* species target antigen is IsdB.

In embodiments, the second antigen-binding domain (D2) binds to any one of the complement components. Complement components include C1q, C1r, C1s, C2, C3, C4, C5, C6, C7, C8, C9, or any fragments thereof (including proteolytic fragments generated by the complement cascade). In certain embodiments, the complement component is C1q. Complement is activated through a series of proteolytic steps which are activated by three major pathways: the Classical Pathway (CP), which is typically activated by immune-complexes, the Alternative Pathway (AP) that can be induced by unprotected cell surfaces, and the Mannose Binding Lectin (MBL) pathway. The Classical Pathway is initiated by C1q/$r_2$/$s_2$ binding to the Fc region of IgM and IgG or directly to a pathogen surface, leading to autoactivation of serine protease C1r which activates serine protease C1s, which in turns cleaves/activates C2 and C4, which then leads to cleavage of C3 and C5, C5b combines with C6, C7, C8, and C9 to form the membrane attack complex (MAC) resulting in cell lysis.

An antigen-binding domain includes polypeptides that bind a *Staphylococcus* species target antigen, such as IsdB, (e.g., a target molecule [T] or a portion thereof) with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay. In embodiments, an antigen-binding domain includes polypeptides that bind IsdB with a $K_D$ of less than about less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

An antigen-binding domain includes polypeptides that bind a complement component, such as C1q, with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay. In embodiments, An antigen-binding domain includes polypeptides that bind a C1q with a $K_D$ of less than about less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C. and/or at 37° C.

While the present disclosure includes bispecific antigen binding molecules wherein one arm of an immunoglobulin binds a *Staphylococcus* species target antigen (e.g. a first antigen-binding domain, D1) and the other arm of the immunoglobulin is specific for a complement component, such as C1q (e.g. the second antigen-binding domain, D2), the target antigen can be any antigen expressed on or in a *Staphylococcus* species, against which a targeted immune response is desired. In embodiments, the complement component can comprise C1q, C1r, C1s, C2, C3, C4, C5, C6, C7, C8, C9, or any fragments thereof (including proteolytic fragments generated by the complement cascade). In certain embodiments, the complement component is C1q. The D1 and/or D2 components of the bispecific antigen-binding molecules of the present disclosure may comprise or consist of antigen-binding fragments of full antibody molecules.

In the context of bispecific antigen binding molecules of the present disclosure wherein one arm of the antibody binds C1q and the other arm binds a *Staphylococcus* species target antigen, the target antigen can be a cell surface antigen. Non-limiting examples of specific target antigens include capsular polysaccharide type 5, capsular polysaccharide type 8, IsdB, IsdA, IsdH, lipoteichoic acid, wall teichoic acid, clumping factor A (clfA), poly-N-acetyl glucosamine (PNAG), lipase, V8 lipase, fatty acid modifying enzyme, microbial surface components recognizing adhesive matrix molecules (eg. adhesins, fibrinogen binding molecules, fibronectin binding protein A, fibronectin binding protein B), protein A, or combinations thereof.

In the context of the bispecific antigen binding molecules of the present disclosure, wherein one arm of the antibody binds C1q and the other arm binds a *Staphylococcus* species target antigen, the bispecific antigen binding molecules bind to the *Staphylococcus* species target antigen with an $EC_{50}$ of about 10 nM or less. In embodiments, the *Staphylococcus* species comprises *Staphylococcus epidermidis, Staphylococcus aureus, Staphylococcus lugdunensis*, or *Staphylococcus saprophiticus*. In the context of bispecific antigen binding molecule of the present disclosure wherein one arm of the antibody binds C1q and the other arm binds a *Staphylococcus* species target antigen, the bispecific antigen binding molecule promotes human C1q deposition on the *Staphylococcus* species with an $EC_{50}$ of about 10 nM or less.

According to certain exemplary embodiments, the present disclosure includes bispecific antigen-binding molecules that specifically bind C1q and IsdB. Such molecules may be referred to herein as, e.g., "anti-IsdB/anti-C1q", or "anti-IsdB×C1q", or "anti-IsdB× anti-C1q" or "IsdB×C1q" bispecific molecules, or other similar terminology.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present disclosure, the first antigen-binding domain specifically binds a first antigen (e.g., *Staphylococcus* species target antigen), and the second antigen-binding domain specifically binds a second, distinct antigen (e.g., C1q).

In certain exemplary embodiments of the present disclosure, the bispecific antigen-binding molecule is a bispecific antibody. Each antigen-binding domain of a bispecific antibody comprises a heavy chain variable domain (HCVR) and a light chain variable domain (LCVR).

In certain exemplary embodiments of the present disclosure, the bispecific antigen-binding molecule comprises a first antigen-binding domain (D1) and a second antigen-binding domain (D2). The first antigen-binding domain and the second antigen-binding domain may be directly or indirectly connected to one another to form a bispecific antigen-binding molecule of the present disclosure. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present disclosure will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif. In embodiments, a multimerizing domain can include an amino acid alteration in the $C_H3$ region that cause a knob to be formed on one multimerization domain and an amino acid alteration in the $C_H3$ region that cause a corresponding hole on another multimerization domain that provides for pairing of the multimerization domains. In embodiments, amino acid alterations can provide for charge pairing of the two multimerization domains.

Any bispecific antigen binding molecule format or technology may be used to make the bispecific antigen-binding molecules of the present disclosure. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules of the present disclosure, the multimerizing domains, e.g., Fc domains, may comprise one or more amino acid changes (e.g., insertions, deletions or substitutions) as compared to the wild-type, naturally occurring version of the Fc domain. For example, the disclosure includes bispecific antigen-binding molecules comprising one or more modifications in the Fc domain that results in a modified Fc domain having a modified binding interaction (e.g., enhanced or diminished) between Fc and FcRn. In another embodiment, the disclosure includes bispecific antigen binding molecules comprising one or more modifications in the Fc domain that results in a modified Fc domain having a modified binding interaction (e.g., diminished) with protein A.

In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0).

Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-C1q antibodies, anti-IsdB antibodies, and/or anti-IsdB× anti-C1q bispecific antigen-binding molecules, comprising an Fc domain comprising one or more pairs or groups of mutations selected from the group: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

The present disclosure also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antigen binding molecule to Protein A as compared to a bispecific antigen binding molecule lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4

$C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present disclosure are described in U.S. Pat. No. 9,359,437 filed Jan. 31, 2014, which is herein incorporated in its entirety. Chimeric Fc domains having these general structural arrangements, and variants thereof, can have altered Fc receptor binding, which in turn affects Fc effector function.

Exemplary antigen-binding domains (D1 and D2) that can be included in the anti-IsdB× anti-C1q bispecific antigen-binding molecules of the present disclosure include antigen-binding domains derived from any of the anti-IsdB (D1) and anti-C1q (D2) antibodies disclosed herein. For example, the present disclosure includes anti-IsdB× anti-C1q bispecific antigen-binding molecules comprising a D1 antigen-binding domain comprising an HCVR comprising an amino acid sequence selected from any of the HCVR amino acid sequences listed in Table 3 and a D2 antigen-binding domain comprising an HCVR comprising an amino acid sequence selected from any of the HCVR amino acid sequences listed in Table 1, or substantially similar sequences thereof having at least 90%, at least 95%, at least 98% or at least 99% sequence identity thereto.

The present disclosure also provides anti-IsdB× anti-C1q bispecific antigen-binding molecules comprising a D1 antigen-binding domain comprising an LCVR comprising an amino acid sequence selected from any of the LCVR amino acid sequences listed in Table 3 and a D2 antigen-binding domain comprising an LCVR comprising an amino acid sequence selected from any of the LCVR amino acid sequences listed in Table 1, or substantially similar sequences thereof having at least 90%, at least 95%, at least 98% or at least 99% sequence identity thereto.

The present disclosure also provides anti-IsdB× anti-C1q bispecific antigen-binding molecules comprising a D1 and D2 antigen-binding domain comprising an HCVR and an LCVR pair (HCVR/LCVR) comprising any of the HCVR amino acid sequences listed in Table 3, or Table 1, paired with any of the LCVR amino acid sequences listed in Table 3, or Table 1.

According to certain embodiments, the present disclosure provides anti-IsdB× anti-C1q bispecific antigen-binding molecules comprising D1 and D2 antigen-binding domains comprising an HCVR/LCVR pair, wherein D1 of the bispecific antigen binding molecule comprises a HCVR amino acid sequence selected from any of the HCVR sequences in Table 3 and wherein D2 of the bispecific antigen binding molecule comprises a HCVR amino acid sequence selected from any of the HCVR sequences in Table 1 and wherein the LCVR amino acid sequence of the bispecific antigen binding molecule comprises any of the LCVR amino acid sequences shown in Table 1 or 3.

For purposes of clarity, the bispecific antibodies of the disclosure are summarized in Table 6, which shows the particular amino acid sequence identifiers for the HCVR and HCDRs assigned to the first antigen-binding domain (D1, anti-IsdB), the amino acid sequence identifiers for the HCVR and HCDRs assigned to the second antigen-binding domain (D2, anti-C1q) and the amino acid sequence identifiers assigned to the LCVR and LCDRs. Each anti-IsdB× anti-C1q bispecific antibody was assigned a new antibody identification number (PID) shown in the first column on the left.

The present disclosure also provides anti-IsdB× anti-C1q bispecific antigen-binding molecules comprising a D1 antigen-binding domain comprising a heavy chain CDR1 (HCDR1) comprising an amino acid sequence selected from any of the HCDR1 amino acid sequences listed in Table 3 or substantially similar sequences thereof having at least 90%, at least 95%, at least 98% or at least 99% sequence identity, and a D2 antigen-binding domain comprising a heavy chain CDR1 (HCDR1) comprising an amino acid sequence selected from any of the HCDR1 amino acid sequences listed in Table 1 or substantially similar sequences thereof having at least 90%, at least 95%, at least 98% or at least 99% sequence identity.

The present disclosure also provides anti-IsdB× anti-C1q bispecific antigen-binding molecules comprising a D1 antigen-binding domain comprising a heavy chain CDR2 (HCDR2) comprising an amino acid sequence selected from any of the HCDR2 amino acid sequences listed in Table 3 or substantially similar sequences thereof having at least 90%, at least 95%, at least 98% or at least 99% sequence identity, and a D2 antigen-binding domain comprising a heavy chain CDR2 (HCDR2) comprising an amino acid sequence selected from any of the HCDR2 amino acid sequences listed in Table 1 or substantially similar sequences thereof having at least 90%, at least 95%, at least 98% or at least 99% sequence identity.

The present disclosure also provides anti-IsdB× anti-C1q bispecific antigen-binding molecules comprising a D1 antigen-binding domain comprising a heavy chain CDR3 (HCDR3) comprising an amino acid sequence selected from any of the HCDR3 amino acid sequences listed in Table 3 or substantially similar sequences thereof having at least 90%, at least 95%, at least 98% or at least 99% sequence identity, and a D2 antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present disclosure also provides anti-IsdB× anti-C1q bispecific antigen-binding molecules comprising a D1 antigen-binding domain comprising a light chain CDR1 (LCDR1) comprising an amino acid sequence selected from any of the LCDR1 amino acid sequences listed in Table 3 or substantially similar sequences thereof having at least 90%, at least 95%, at least 98% or at least 99% sequence identity and a D2 antigen-binding domain comprising a light chain CDR1 (LCDR1) comprising an amino acid sequence selected from any of the LCDR1 amino acid sequences listed in Table 1 or substantially similar sequences thereof having at least 90%, at least 95%, at least 98% or at least 99% sequence identity.

The present disclosure also provides anti-IsdB× anti-C1q bispecific antigen-binding molecules comprising a D1 antigen-binding domain comprising a light chain CDR2 (LCDR2) comprising an amino acid sequence selected from any of the LCDR2 amino acid sequences listed in Table 3 or substantially similar sequences thereof having at least 90%, at least 95%, at least 98% or at least 99% sequence identity and a D2 antigen-binding domain comprising a light chain CDR2 (LCDR2) comprising an amino acid sequence selected from any of the LCDR2 amino acid sequences listed in Table 1, or substantially similar sequences thereof having at least 90%, at least 95%, at least 98% or at least 99% sequence identity.

The present disclosure also provides anti-IsdB× anti-C1q bispecific antigen-binding molecules comprising a D1 antigen-binding domain comprising a light chain CDR3 (LCDR3) comprising an amino acid sequence selected from any of the LCDR3 amino acid sequences listed in Table 3 or substantially similar sequences thereof having at least 90%, at least 95%, at least 98% or at least 99% sequence identity and a D2 antigen-binding domain comprising a light chain CDR3 (LCDR3) comprising an amino acid sequence selected from any of the LCDR3 amino acid sequences listed in Table 1, or substantially similar sequences thereof having at least 90%, at least 95%, at least 98% or at least 99% sequence identity.

The present disclosure also provides anti-IsdB× anti-C1q bispecific antigen-binding molecules comprising D1 and/or D2 antigen-binding domains comprising an HCDR3 and an LCDR3 pair (HCDR3/LCDR3) comprising any of the HCDR3 amino acid sequences listed in Table 1 or 3 paired with any of the LCDR3 amino acid sequences listed in Table 1 or 3.

The present disclosure also provides anti-IsdB× anti-C1q bispecific antigen-binding molecules comprising a D1 and/or D2 antigen-binding domain comprising a set of six CDRs (i.e., HCDR1-HCDR2-HCDR3-LCDR1-LCDR2-LCDR3) contained within any of the exemplary anti-IsdB or anti-C1q antibodies listed in Table 1 or Table 3.

In a related embodiment, the present disclosure provides anti-IsdB× anti-C1q bispecific antigen-binding molecules comprising a D1 and/or D2 antigen-binding domain comprising a set of six CDRs (i.e., HCDR1-HCDR2-HCDR3-LCDR1-LCDR2-LCDR3) contained within an HCVR/LCVR pair as defined by any of the exemplary anti-IsdB or anti-C1q antibodies listed in Table 1 or Table 3.

The anti-IsdB× anti-C1q bispecific antigen-binding molecules of the present disclosure may comprise a D1 antigen-binding domain derived from any of the anti-IsdB antibodies of Table 3, and a D2 antigen-binding domain derived from any of the anti-C1q antibodies of Table 1. Non-limiting examples of anti-IsdB× anti-C1q bispecific antibodies of the present disclosure are depicted in Table 6.

As a non-limiting illustrative example, the present disclosure includes anti-IsdB× anti-C1q bispecific antigen binding molecules comprising a D1 antigen-binding domain and a D2 antigen-binding domain, wherein the D1 antigen binding domain comprises an HCVR/LCVR pair comprising amino acid sequences of SEQ ID NOs: 138/146, or a set of heavy and light chain CDRs (HCDR1-HCDR2-HCDR3-LCDR1-LCDR2-LCDR3), the set comprising amino acid sequences of SEQ ID NOs: 140-142-144-148-150-152, and wherein the D2 antigen-binding domain comprises an HCVR/LCVR pair comprising amino acid sequences of SEQ ID NOs: 2/146, or a set of heavy and light chain CDRs (HCDR1-HCDR2-HCDR3-LCDR1-LCDR2-LCDR3), the set comprising amino acid sequences of SEQ ID NOs: 4-6-8-148-150-152. An exemplary anti-IsdB× anti-C1q bispecific antibody having these sequence characteristics is the bispecific antibody designated H1H20631D, which comprises a D1 derived from H1H20295P2 and a D2 derived from H1×H17736P2 (see Table 6 herein).

Sequence Variants

The antibodies and bispecific antigen-binding molecules of the present disclosure may comprise one or more amino acid substitutions, insertions and/or deletions in the framework and/or CDR regions of the heavy and light chain variable domains as compared to the corresponding germline sequences from which the individual antigen-binding domains were derived as described herein. The present disclosure also includes antigen-binding molecules wherein one or both antigen-binding domains comprise variants of any of the HCVR, LCVR, and/or CDR amino acid sequences disclosed herein having one or more conservative substitutions. For example, the present disclosure includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. Conservative amino acid substitutions are described elsewhere herein.

The present disclosure also includes antigen-binding molecules comprising an antigen-binding domain with an HCVR, LCVR, and/or CDR amino acid sequence that is substantially identical to any of the HCVR, LCVR, and/or CDR amino acid sequences disclosed herein.

pH-Dependent Binding

The present disclosure includes anti-C1q antibodies, anti-IsdB antibodies, and/or anti-IsdB× anti-C1q bispecific antigen-binding molecules, with pH-dependent binding characteristics. For example, the bispecific antigen binding molecule of the present disclosure may exhibit reduced binding to C1q or IsdB at acidic pH as compared to neutral pH. Alternatively, the bispecific antigen binding molecules of the disclosure may exhibit enhanced binding to C1q or IsdB at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Biological Characteristics of the Antibodies and Bispecific Antigen-Binding Molecules The present disclosure includes antibodies, antigen-binding fragments thereof, and bispecific antigen binding molecules that bind a complement component, e.g. C1q. In embodiments, the bispecific antigen binding molecules inhibit C1q binding to immunoglobulin molecules, inhibit hemolysis, and/or complement dependent cytotoxicity. In embodiments, the bispecific antigen binding molecule blocks the binding of the human C1q to human IgG1-k with an $IC_{50}$ of about 10 nM or less. In other embodiments, the bispecific antigen binding molecule blocks the binding of the human C1q to human IgM with an $IC_{50}$ of about 50 nM or less. In embodiments, the bispecific antigen binding molecule inhibits complement dependent cytotoxicity with an $IC_{50}$ of about 100 nM or less. In further embodiments, the bispecific antigen binding molecule provides for deposition of C1q with an $EC_{50}$ of about 10 nM or less.

The present disclosure includes antibodies, antigen-binding fragments thereof, and bispecific antigen binding molecules that bind to a *Staphylococcus* species target antigen. In embodiments, the *Staphylococcus* species comprise *Staphylococcus epidermidis*, *Staphylococcus aureus*, *Staphylococcus lugdunensis*, and/or *Staphylococcus saprophiticus*. In embodiments, the *Staphylococcus* species is an antibiotic resistant species such as methicillin resistant *Staphylococcus aureus*. In embodiments, the *Staphylococcus* species target antigen comprises capsular polysaccharide type 5, capsular polysaccharide type 8, IsdB, IsdA, IsdH, lipoteichoic acid, wall teichoic acid, clumping factor A (clfA), poly-N-acetyl glucosamine (PNAG), lipase, V8 lipase, fatty acid modifying enzyme, microbial surface components recognizing adhesive matrix molecules (eg. adhesins, fibrinogen binding molecules, fibronectin binding protein A, fibronectin binding protein B), protein A, or combinations thereof.

In embodiments, an isolated bispecific antigen binding molecule that comprises a first antigen-binding domain (D1) that binds a *Staphylococcus* species target antigen; and a second antigen-binding domain (D2) that binds a human C1q, binds to the *Staphylococcus* species target antigen with an $EC_{50}$ of about 10 nM or less. In embodiments, an isolated bispecific antigen binding molecule that comprises a first antigen-binding domain D1; and a second antigen-binding domain D2 promotes human C1q deposition on the *Staphylococcus* species with an $EC_{50}$ of about 10 nM or less.

The present disclosure includes antibodies and antigen-binding fragments thereof that bind human C1q with high affinity, e.g. about 1 nM or less. The present disclosure also includes antibodies and antigen-binding fragments thereof that bind human C1q with medium or low affinity, e.g. about 2 nM or more, depending on the therapeutic context and particular targeting properties that are desired. The present disclosure includes antibodies and antigen-binding fragments thereof that bind IsdB with high affinity, e.g. about 5 nM or less. The present disclosure also includes antibodies and antigen-binding fragments thereof that bind IsdB with medium or low affinity, e.g. about 10 nM or more, depending on the therapeutic context and particular targeting properties that are desired.

The present disclosure includes anti-IsdB× anti-C1q bispecific antigen-binding molecules, which are capable of inhibiting the growth of or an infection with a *Staphylococcus* species in a subject (see, e.g., Example 8, Example 9). For example, according to certain embodiments, anti-IsdB× anti-C1q bispecific antigen-binding molecules are provided, wherein a single administration of the bispecific antigen-binding molecule to a subject (e.g., at a dose of about 0.1 mg/kg, about 0.08 mg/kg, about 0.06 mg/kg about 0.04 mg/kg, about 0.04 mg/kg, about 0.02 mg/kg, about 0.01 mg/kg, or less) causes a reduction in the colony forming units (CFUs) of a *Staphylococcus* species in the subject (e.g., in a blood sample taken from the subject). In certain embodiments, a single administration of the anti-IsdB× anti-C1q bispecific antigen-binding molecule at a dose of about 0.1 mg/kg causes an increase in survival of an animal infected with *Staphylococcus aureus* by about day 21, about day 18, about day 14, about day 10, about day 7, about day 5, about day 2, or about day 1 after administration of the bispecific antigen-binding molecule to the subject.

Epitope Mapping and Related Technologies

The epitope on C1q or IsdB to which the bispecific antigen-binding molecules of the present disclosure bind may comprise or consist of a single contiguous sequence of 3 or more (e.g., 3, 4, 5, 6, 7, 8, 9, 10, 11, 12, 13, 14, 15, 16, 17, 18, 19, 20 or more) amino acids of a C1q protein or IsdB protein. Alternatively, the epitope may comprise or consist of a plurality of non-contiguous amino acids (or amino acid sequences) of C1q or IsdB. The antibodies of the disclosure may interact with amino acids contained within a single C1q chain (e.g., component a, b, or c), may interact with amino acids on two or more different C1q chains, may interact with a trimer, or may interact with a hexamer. Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present disclosure also includes bispecific antigen-binding molecules comprising a first antigen-binding domain (D1) that specifically binds a *Staphylococcus* species target antigen, and a second antigen binding domain (D2) that specifically binds a complement component, wherein the first antigen-binding domain binds to the same epitope on any of the specific exemplary *Staphylococcus* species target antigen-binding domains described herein, and/or wherein the second antigen-binding domain binds to the same epitope on the complement component as any of the specific exemplary C1q-specific antigen-binding domains described herein. Exemplary embodiments include an isolated bispecific antigen binding molecule that binds to the same epitope on human C1q as a reference antibody comprising an HCVR/LCVR pair comprising an amino acid sequence of SEQ ID NOs: 2/146 or SEQ ID NOs:106/146. Exemplary embodiments include an isolated bispecific antigen binding molecule that binds to the same epitope on IsdB as a reference antibody comprising an HCVR/LCVR pair comprising an amino acid sequence of SEQ ID NOs: 138/146.

Likewise, the present disclosure also includes bispecific antigen-binding molecules comprising a first antigen-binding domain (D1) that specifically binds IsdB, and a second antigen binding domain (D2) that specifically binds human C1q, wherein the first antigen-binding domain competes for binding to IsdB with any of the specific exemplary IsdB-specific antigen-binding domains described herein, such as a reference antibody comprising an HCVR/LCVR pair comprising amino acid sequences of SEQ ID NOs:138/146, and/or wherein the second antigen-binding domain competes for binding to human C1q with any of the specific exemplary C1q-specific antigen-binding domains described herein, such as a reference antibody comprising an HCVR/LCVR pair comprising amino acid sequences of SEQ ID NOs:2/146 or SEQ ID NOs:106/146.

One can easily determine whether a particular antigen-binding molecule (e.g., antibody) or antigen-binding domain thereof binds to the same epitope as, or competes for binding with, a reference antigen-binding molecule of the present disclosure by using routine methods known in the art. For example, to determine if a test antibody binds to the same epitope on C1q (or IsdB) as a reference bispecific antigen-binding molecule of the present disclosure, the reference bispecific molecule is first allowed to bind to a C1q protein (or IsdB protein). Next, the ability of a test antibody to bind to the C1q (or IsdB) molecule is assessed. If the test antibody is able to bind to C1q (or IsdB) following saturation binding with the reference bispecific antigen-binding molecule, it can be concluded that the test antibody binds to a different epitope of C1q (or IsdB) than the reference bispecific antigen-binding molecule. On the other hand, if the test antibody is not able to bind to the C1q (or IsdB) molecule following saturation binding with the reference bispecific antigen-binding molecule, then the test antibody may bind to the same epitope of C1q (or IsdB) as the epitope bound by the reference bispecific antigen-binding molecule of the disclosure. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a C1q protein (or IsdB protein) under saturating conditions followed by assessment of binding of the test antibody to the C1q (or IsdB) molecule. In a second orientation, the test antibody is allowed to bind to a C1q (or IsdB) molecule under saturating conditions followed by assessment of binding of the reference antigen-binding molecule to the C1q (or IsdB) molecule. If, in both orientations, only the first (saturating) antigen-binding molecule is capable of binding to the C1q (or IsdB) molecule, then it is concluded that the test antibody and the reference antigen-binding molecule compete for binding to C1q (or IsdB). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., C1q and IsdB), can be appropriately arranged relative to one another to produce a bispecific antigen-binding molecule of the present disclosure using routine methods. (A discussion of exemplary bispecific antibody formats that can be used to construct the bispecific antigen-binding molecules of the present disclosure is provided elsewhere herein). In certain embodiments, one or more of the individual components (e.g., heavy and light chains) of the multispecific antigen-binding molecules of the disclosure are derived from chimeric, humanized or fully human antibodies.

Methods for making such antibodies are well known in the art. For example, one or more of the heavy and/or light chains of the bispecific antigen-binding molecules of the present disclosure can be prepared using VELOCIMMUNE® technology. Using VELOCIMMUNE® technology (or any other human antibody generating technology), high affinity chimeric antibodies to a particular antigen (e.g., C1q or IsdB) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present disclosure.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present disclosure encompasses antigen-binding molecules having amino acid sequences that vary from those of the exemplary molecules disclosed herein but that retain the ability to bind C1q and/or IsdB. Such variant molecules may comprise one or more additions, deletions, or substitutions of amino acids when compared to parent sequence, but exhibit biological activity that is essentially equivalent to that of the described bispecific antigen-binding molecules.

The present disclosure includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Immunoconjugates

The present disclosure encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

The present disclosure provides pharmaceutical compositions comprising the antigen-binding molecules of the present disclosure. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present disclosure is used for therapeutic purposes in an adult patient, it may be advantageous to intravenously administer the bispecific antigen-binding molecule of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present disclosure includes methods of inhibiting the growth of a *Staphylococcus* species in a subject comprising administering a therapeutic composition comprising a bispecific antigen-binding molecule that specifically binds a complement component (e.g., C1q) and a *Staphylococcus* species target antigen (e.g., IsdB) to a subject in need thereof. The therapeutic composition can comprise any of the antibodies or fragments thereof or bispecific antigen-binding molecules as disclosed herein and a pharmaceutically acceptable carrier or diluent. As used herein, the expression "a subject in need thereof" means a human or non-human animal that exhibits one or more symptoms or indicia of infection, or who otherwise would benefit from an inhibition or reduction in *Staphylococcus* species.

The antibodies and bispecific antigen-binding molecules of the disclosure (and therapeutic compositions comprising the same) are useful, inter alia, for treating any disease or disorder in which inhibition, reduction of the growth of a *Staphylococcus* species would be beneficial. In particular, the anti-IsdB× anti-C1q bispecific antigen-binding molecules of the present disclosure may be used for the treatment, prevention and/or amelioration of any disease or disorder associated with or mediated by *Staphylococcus* species. The mechanism of action by which the therapeutic methods of the disclosure are achieved include killing of the cells expressing IsdB in the presence of effector cells, for example, by CDC, apoptosis, ADCC, phagocytosis, or by a combination of two or more of these mechanisms. Cells expressing IsdB or other target antigens which can be inhibited or killed using the bispecific antigen-binding molecules of the disclosure include, for example, *Staphylococcus epidermidis, Staphylococcus aureus, Staphylococcus lugdunensis*, and/or *Staphylococcus saprophiticus*. In embodiments, the *Staphylococcus* species is an antibiotic resistant species such as methicillin resistant *Staphylococcus aureus*.

The antigen-binding molecules of the present disclosure may be used to treat diseases or disorders associated with infection with *Staphylococcus* species, especially antibiotic resistant species, including a skin infection, cellulitis, pneumonia, meningitis, urinary tract infection, toxic shock syndrome, endocarditis, pericarditis, osteomyelitis, bacteremia, or sepsis. The antigen-binding molecules of the present disclosure may also be used to prevent infections with a *Staphylococcus* species that may arise during or following a surgical procedure, such as surgery that involves implantation of a prosthetic. In certain embodiments, the prosthetic may be a prosthetic limb, such as an arm or a leg. In certain embodiments, the prosthetic may be a hip replacement. In certain embodiments, the prosthetic may be a cosmetic prosthetic, such as, but not limited to an ocular prosthetic, silicone hands, fingers, breasts, feet, toes, or a facial implant.

Combination Therapies and Formulations

The present disclosure provides methods, which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present disclosure comprise an antibiotic, an antibody that binds a *Staphylococcus* antigen, an antibody that binds a *Staphylococcus* toxin, an antibody that binds human or cynomolgus C1q, a vaccine specific for *Staphylococcus* species, an antibody drug conjugate (e.g. a bispecific antibody conjugated to an antibiotic), or combinations thereof.

The additional therapeutically active component(s) may be administered just prior to, concurrent with, or shortly after the administration of an antigen-binding molecule of the present disclosure; (for purposes of the present disclosure, such administration regimens are considered the administration of an antigen-binding molecule "in combination with" an additional therapeutically active component).

The present disclosure includes pharmaceutical compositions in which an antigen-binding molecule of the present disclosure is co-formulated with one or more of the additional therapeutically active component(s) as described elsewhere herein.

Administration Regimens

According to certain embodiments of the present disclosure, multiple doses of an antigen-binding molecule (e.g., a bispecific antigen-binding molecule that specifically binds IsdB and C1q) may be administered to a subject over a defined time course. The methods according to this aspect of the disclosure comprise sequentially administering to a subject multiple doses of an antigen-binding molecule of the disclosure. As used herein, "sequentially administering" means that each dose of an antigen-binding molecule is administered to the subject at a different point in time, e.g., on different days separated by a predetermined interval (e.g., hours, days, weeks or months). The present disclosure includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is Administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or More) Days after the Immediately Preceding Dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the disclosure may comprise administering to a patient any number of secondary and/or tertiary doses of an antigen-binding molecule (e.g., a bispecific antigen-binding molecule that specifically binds IsdB and C1q). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments, involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Preparation of Anti-C1q Antibodies

Anti-C1q antibodies were obtained by immunizing a VELOCIMMUNE® mouse (i.e., an engineered mouse comprising DNA encoding human Immunoglobulin heavy and kappa light chain variable regions; See U.S. Pat. No. 6,596,541) with a human complement component 1q (C1q). Human complement C1q is a hexamer that comprises three unique subunits: A(29 kDa); B(26 kDa); and C(22 kDa). An exemplary sequence of subunit A is found at amino acids 1-245 of accession number NP_057075 (SEQ ID NO:170). An exemplary sequence of subunit B is found at amino acids 1-253 of accession number NP_000482 (SEQ ID NO:171). An exemplary sequence of subunit C is found at amino acids 1-245 of accession number NP_758957 (SEQ ID NO:172). Human C1q is also commercially available from a source such as Quidel. In embodiments, the commercially available human C1q from Quidel was used as the immunogen. The antibody immune response was monitored by a C1q-specific immunoassay.

Several fully human anti-C1q antibodies were isolated directly from antigen-positive B cells from the VELOCIMMUNE® mouse without fusion to myeloma cells, as described in U.S. Pat. No. 7,582,298. Antibodies are typically referred to herein according to the following nomenclature: Fc prefix (e.g. "H1H," "H1xH" etc.), followed by a numerical identifier (e.g. "2712," "2692," etc., as shown in Table 1), followed by a "P," or "D" suffix. The designation "H1xH" refers to an antibody whose Fc has been modified/mutated to exclude binding to protein A. Exemplary modifications of Fc domains that provide for antibodies that do not bind to protein A are described elsewhere herein. The H1H, and H1xH prefixes on the antibody designations used herein indicate the particular Fc region isotype of the antibody. For example, an "H1H" antibody has a human IgG1 Fc, and an "H1xH" antibody has a mutated Fc (See U.S. Pat. No. 8,586,713). All variable regions are fully human as denoted by the first 'H' in the antibody designation. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain.

Once the antibodies were isolated, the nucleic acid and amino acid sequences were obtained. The amino acid sequence identifiers of the anti-C1q antibodies heavy chain variable region (HCVR), heavy chain complementarity determining region 1 (HCDR1), heavy chain complementarity determining region 2 (HCDR2), heavy chain complementarity determining region 3 (HCDR3), light chain variable region (LCVR), light chain complementarity determining region 1 (LCDR1), light chain complementarity determining region 2 (HCDR2), light chain complementarity determining region 3 (HCDR3) are shown in Table 1 below. The nucleic acid sequence identifiers are shown in Table 2.

TABLE 1

Amino Acid Sequence Identifiers for anti-hC1q antibodies

| Antibody Designation | HCVR | HCDR1 | HCDR2 | HCDR3 | LCVR | LCDR1 | LCDR2 | LCDR3 |
|---|---|---|---|---|---|---|---|---|
| H1xH17736P2 | 2 | 4 | 6 | 8 | 146 | 148 | 150 | 152 |
| H1xH17738P2 | 10 | 12 | 14 | 16 | 146 | 148 | 150 | 152 |
| H1xH17751P2 | 18 | 20 | 22 | 24 | 162 | 164 | 166 | 168 |
| H1xH17756P2 | 26 | 28 | 30 | 32 | 162 | 164 | 166 | 168 |
| H1xH17758P2 | 34 | 36 | 38 | 40 | 162 | 164 | 166 | 168 |
| H1xH17760P2 | 42 | 44 | 46 | 48 | 162 | 164 | 166 | 168 |
| H1xH17763P2 | 50 | 52 | 54 | 56 | 162 | 164 | 166 | 168 |
| H1xH17769P2 | 58 | 60 | 62 | 64 | 162 | 164 | 166 | 168 |
| H1xH17773P2 | 66 | 68 | 70 | 72 | 162 | 164 | 166 | 168 |
| H1xH17779P2 | 74 | 76 | 78 | 80 | 162 | 164 | 166 | 168 |
| H1xH17781P2 | 82 | 84 | 86 | 88 | 162 | 164 | 166 | 168 |
| H1xH18392P2 | 90 | 92 | 94 | 96 | 146 | 148 | 150 | 152 |
| H1xH18394P2 | 98 | 100 | 102 | 104 | 146 | 148 | 150 | 152 |
| H1xH18395P2 | 106 | 108 | 110 | 112 | 146 | 148 | 150 | 152 |
| H1xH18400P2 | 114 | 116 | 118 | 120 | 162 | 164 | 166 | 168 |
| H1xH18411P2 | 122 | 124 | 126 | 128 | 162 | 164 | 166 | 168 |
| H1xH18412P2 | 130 | 132 | 134 | 136 | 162 | 164 | 166 | 168 |

TABLE 2

Nucleic Acid Sequence Identifiers for anti-hC1q antibodies

| Antibody Designation | HCVR | HCDR1 | HCDR2 | HCDR3 | LCVR | LCDR1 | LCDR2 | LCDR3 |
|---|---|---|---|---|---|---|---|---|
| H1xH17736P2 | 1 | 3 | 5 | 7 | 145 | 147 | 149 | 151 |
| H1xH17738P2 | 9 | 11 | 13 | 15 | 145 | 147 | 149 | 151 |
| H1xH17751P2 | 17 | 19 | 21 | 23 | 161 | 163 | 165 | 167 |
| H1xH17756P2 | 25 | 27 | 29 | 31 | 161 | 163 | 165 | 167 |
| H1xH17758P2 | 33 | 35 | 37 | 39 | 161 | 163 | 165 | 167 |
| H1xH17760P2 | 41 | 43 | 45 | 47 | 161 | 163 | 165 | 167 |
| H1xH17763P2 | 49 | 51 | 53 | 55 | 161 | 163 | 165 | 167 |
| H1xH17769P2 | 57 | 59 | 61 | 63 | 161 | 163 | 165 | 167 |
| H1xH17773P2 | 65 | 67 | 69 | 71 | 161 | 163 | 165 | 167 |
| H1xH17779P2 | 73 | 75 | 77 | 79 | 161 | 163 | 165 | 167 |
| H1xH17781P2 | 81 | 83 | 85 | 87 | 161 | 163 | 165 | 167 |
| H1xH18392P2 | 89 | 91 | 93 | 95 | 145 | 147 | 149 | 151 |
| H1xH18394P2 | 97 | 99 | 101 | 103 | 145 | 147 | 149 | 151 |

TABLE 2-continued

| Nucleic Acid Sequence Identifiers for anti-hC1q antibodies | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H1xH18395P2 | 105 | 107 | 109 | 111 | 145 | 147 | 149 | 151 |
| H1xH18400P2 | 113 | 115 | 117 | 119 | 161 | 163 | 165 | 167 |
| H1xH18411P2 | 121 | 123 | 125 | 127 | 161 | 163 | 165 | 167 |
| H1xH18412P2 | 129 | 131 | 133 | 135 | 161 | 163 | 165 | 167 |

Example 2. Preparation of Anti-IsdB Antibodies

Anti-IsdB antibodies were obtained by immunizing a VELOCIMMUNE® mouse (i.e., an engineered mouse comprising DNA encoding human Immunoglobulin heavy and kappa light chain variable regions, See U.S. Pat. No. 6,596,541) with an antigen derived from a heme uptake protein IsdB from *Staphylococcus aureus* (IsdB). An embodiment of the antigen comprises amino acids 41 to 613 of Accession no. WP_063557416. An example of the amino acid sequence of an IsdB antigen is amino acids 3 to 574 of SEQ ID NO:169 The antibody immune response was monitored by a IsdB-specific immunoassay.

Several fully human anti-IsdB antibodies were isolated directly from antigen-positive B cells VELOCIMMUNE® mouse without fusion to myeloma cells, as described in U.S. Pat. No. 7,582,298. Once the antibodies were isolated, the nucleic acid and amino acid sequences were obtained. The amino acid sequence identifiers of the anti-C1q antibodies heavy chain variable region (HCVR), heavy chain complementarity determining region 1 (HCDR1), heavy chain complementarity determining region 2 (HCDR2), heavy chain complementarity determining region 3 (HCDR3), light chain variable region (LCVR), light chain complementarity determining region 1 (LCDR1), light chain complementarity determining region 2 (HCDR2), light chain complementarity determining region 3 (HCDR3) are shown in Table 3 below. The nucleic acid sequence identifiers are shown in Table 4.

TABLE 3

| Amino Acid Sequence Identifiers for anti-IsdB antibodies | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H1xH20295P2 | 138 | 140 | 142 | 144 | 146 | 148 | 150 | 152 |
| H1xH20318P2 | 154 | 156 | 158 | 160 | 162 | 164 | 166 | 168 |

TABLE 4

| Nucleic Acid Sequence identifiers for anti-IsdB antibodies | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H1xH20295P2 | 137 | 139 | 141 | 143 | 145 | 147 | 149 | 151 |
| H1xH20318P2 | 153 | 155 | 157 | 159 | 161 | 163 | 165 | 167 |

Example 3. Preparation of Bispecific Anti-C1q and Anti-IsdB Bispecific Antibody Bispecific antibodies comprising an anti-C1q-specific binding domain and an anti-IsdB specific binding domain were constructed using standard methodologies wherein a heavy chain from an anti-C1q antibody and a light chain were combined with a heavy chain from an anti-IsdB antibody and a light chain. The anti-C1q antibodies used to construct the bispecific antibodies of this example were obtained by immunizing a VelocImmune® mouse as described in Example 1. The anti-IsdB antibodies used to construct the bispecific antibodies of this example were obtained as described in Example 2.

The bispecific antibodies created in accordance with the present Example comprise two separate antigen-binding domains (i.e., binding arms), D1 and D2. In embodiments, the first antigen-binding domain (D1) comprises a heavy chain variable region (HCVR) derived from an anti-IsdB antibody ("IsdB-VH"), paired with a light chain variable region (LCVR) and creates an antigen-binding domain that specifically recognizes *Staphylococcus aureus* IsdB protein. In embodiments, the second antigen-binding domain (D2) comprises a heavy chain variable region (HCVR) derived from an anti-C1q ("C1q-VH"), paired with a light chain variable region (LCVR) and creates an antigen-binding domain that specifically recognizes human C1q. One of skill in the art understands that bispecific antibodies can be constructed in many other formats including single chain Fv, dual affinity retargeting proteins, tandem diabodies, knob and hole pairings, charge pairings, cross Mab, double variable domain Ig, s-Fab, and Fv-Fc. A listing of the identifiers of each of the arms and of the bispecific antibodies is provided in Table 5. The amino acid sequence identifiers of the heavy chain variable domains and CDRs of each arm of the bispecific antibodies are shown in Table 6.

TABLE 5

| Bispecific Ab Identification No. | Anti-C1q Identification No. | Anti-IsdB Identification No. |
|---|---|---|
| H1H20631D | H1xH17736P2VH | H1H20295P2VH |
| H1H20632D | H1xH17738P2VH | H1H20295P2VH |
| H1H20633D | H1xH18392P2VH | H1H20295P2VH |
| H1H20634D | H1xH18394P2VH | H1H20295P2VH |
| H1H20635D | H1xH18395P2VH | H1H20295P2VH |
| H1H20636D | H1xH17773P2VH | H1H20318P2VH |
| H1H20637D | H1xH17779P2VH | H1H20318P2VH |
| H1H20638D | H1xH17781P2VH | H1H20318P2VH |
| H1H20639D | H1xH17751P2VH | H1H20318P2VH |
| H1H20640D | H1xH17756P2VH | H1H20318P2VH |
| H1H20641D | H1xH17758P2VH | H1H20318P2VH |
| H1H20642D | H1xH17760P2VH | H1H20318P2VH |
| H1H20643D | H1xH17763P2VH | H1H20318P2VH |
| H1H20644D | H1xH17769P2VH | H1H20318P2VH |
| H1H20645D | H1xH18400P2VH | H1H20318P2VH |
| H1H20646D | H1xH18411P2VH | H1H20318P2VH |
| H1H20647D | H1xH18412P2VH | H1H20318P2VH |

TABLE 6

Amino acid Sequence IDs

| anti-IsdB x anti-C1q Bispecific Antibody | First Antigen-Binding Domain (D1, anti-IsdB) | | | | Second Antigen-Binding Domain (D2, anti-C1q) | | | | Light Chain Variable Region (D3, Vκ) | | | |
|---|---|---|---|---|---|---|---|---|---|---|---|---|
| | D1-HCVR | D1-HCDR1 | D1-HCDR2 | D1-HCDR3 | D2-HCVR | D2-HCDR1 | D2-HCDR2 | D2-HCDR3 | D3-LCVR | D3-LCDR1 | D3-LCDR2 | D3-LCDR3 |
| H1H20631D | H1H20295P2VH | | | | H1xH17736P2VH | | | | H1H20295P2VK | | | |
| | 138 | 140 | 142 | 144 | 2 | 4 | 6 | 8 | 146 | 148 | 150 | 152 |
| H1H20632D | H1H20295P2VH | | | | H1xH17738P2VH | | | | H1H20295P2VK | | | |
| | 138 | 140 | 142 | 144 | 10 | 12 | 14 | 16 | 146 | 148 | 150 | 152 |
| H1H20633D | H1H20295P2VH | | | | H1xH18392P2VH | | | | H1H20295P2VK | | | |
| | 138 | 140 | 142 | 144 | 90 | 92 | 94 | 96 | 146 | 148 | 150 | 152 |
| H1H20634D | H1H20295P2VH | | | | H1xH18394P2VH | | | | H1H20295P2VK | | | |
| | 138 | 140 | 142 | 144 | 98 | 100 | 102 | 104 | 146 | 148 | 150 | 152 |
| H1H20635D | H1H20295P2VH | | | | H1xH18395P2VH | | | | H1H20295P2VK | | | |
| | 138 | 140 | 142 | 144 | 106 | 108 | 110 | 112 | 146 | 148 | 150 | 152 |
| H1H20636D | H1H20318P2VH | | | | H1xH17773P2VH | | | | H1H20318P2VK | | | |
| | 154 | 156 | 158 | 160 | 66 | 68 | 70 | 72 | 162 | 164 | 166 | 168 |
| H1H20637D | H1H20318P2VH | | | | H1xH17779P2VH | | | | H1H20318P2VK | | | |
| | 154 | 156 | 158 | 160 | 74 | 76 | 78 | 80 | 162 | 164 | 166 | 168 |
| H1H20638D | H1H20318P2VH | | | | H1xH17781P2VH | | | | H1H20318P2VK | | | |
| | 154 | 156 | 158 | 160 | 82 | 84 | 86 | 88 | 162 | 164 | 166 | 168 |
| H1H20639D | H1H20318P2VH | | | | H1xH17751P2VH | | | | H1H20318P2VK | | | |
| | 154 | 156 | 158 | 160 | 18 | 20 | 22 | 24 | 162 | 164 | 166 | 168 |
| H1H20640D | H1H20318P2VH | | | | H1xH17756P2VH | | | | H1H20318P2VK | | | |
| | 154 | 156 | 158 | 160 | 26 | 28 | 30 | 32 | 162 | 164 | 166 | 168 |
| H1H20641D | H1H20318P2VH | | | | H1xH17758P2VH | | | | H1H20318P2VK | | | |
| | 154 | 156 | 158 | 160 | 34 | 36 | 38 | 40 | 162 | 164 | 166 | 168 |
| H1H20642D | H1H20318P2VH | | | | H1xH17760P2VH | | | | H1H20318P2VK | | | |
| | 154 | 156 | 158 | 160 | 42 | 44 | 46 | 48 | 162 | 164 | 166 | 168 |
| H1H20643D | H1H20318P2VH | | | | H1xH17763P2VH | | | | H1H20318P2VK | | | |
| | 154 | 156 | 158 | 160 | 50 | 52 | 54 | 56 | 162 | 164 | 166 | 168 |
| H1H20644D | H1H20318P2VH | | | | H1xH17769P2VH | | | | H1H20318P2VK | | | |
| | 154 | 156 | 158 | 160 | 58 | 60 | 62 | 64 | 162 | 164 | 166 | 168 |
| H1H20645D | H1H20318P2VH | | | | H1xH18400P2VH | | | | H1H20318P2VK | | | |
| | 154 | 156 | 158 | 160 | 114 | 116 | 118 | 120 | 162 | 164 | 166 | 168 |
| H1H20646D | H1H20318P2VH | | | | H1xH18411P2VH | | | | H1H20318P2VK | | | |
| | 154 | 156 | 158 | 160 | 122 | 124 | 126 | 128 | 162 | 164 | 166 | 168 |
| H1H20647D | H1H20318P2VH | | | | H1xH18412P2VH | | | | H1H20318P2VK | | | |
| | 154 | 156 | 158 | 160 | 130 | 132 | 134 | 136 | 162 | 164 | 166 | 168 |

Example 4: Kinetics of Human C1q and IsdB-6xHis Binding to Anti-IsdBx Anti-C1q Bispecific Antibodies at 25° C. and 37° C.

Equilibrium dissociation constants ($K_D$ values) for human C1q (Quidel) and IsdB-6xHis (REGN2655; See also SEQ ID NO: 169) binding to respective C1q and IsdB arms of purified anti-IsdBx anti-C1q bispecific antibodies were determined using a real-time surface plasmon resonance biosensor (Biacore 4000). The CM5 Biacore sensor surface was derivatized by amine coupling with a monoclonal mouse anti-human Fc antibody (GE Healthcare, # BR-1008-39) to capture purified anti-IsdBx anti-C1q bispecific antibodies. All Biacore binding studies were performed in a buffer composed of 0.01M HEPES pH 7.4, 0.15M NaCl, 3 mM EDTA, 0.05% v/v Surfactant P20 (running buffer). The native human complement component C1q protein purified from human serum was purchased from Quidel and here on referred to as hC1q was tested at concentrations ranging from 0.6 nM to 20 nM. Recombinant bacterial IsdB expressed with a hexahistidine tag (IsdB-6xHis; REGN2655; SEQ ID NO:169; WP_063557416.1) from here on referred to as IsdB-6xHis was tested at concentrations ranging from 0.37 nM-90 nM and injected over the anti-IsdBx anti-C1q bispecific antibody-captured surface at a flow rate of 304/minute. Antibody-reagent association was monitored for 3 minutes while dissociation was monitored for 5 minutes. All binding kinetic experiments were performed at 25° C. or 37° C. Kinetic association (ka) and dissociation (kd) rate constants were determined by fitting the real-time sensorgrams to a 1:1 binding model using Scrubber 2.0c curve fitting software. Binding dissociation equilibrium constants (KD) and dissociative half-lives (t½) were calculated from the kinetic rate constants as:

$$K_D(M) = \frac{kd}{ka}, \text{ and } t\frac{1}{2}(\min) = \frac{\ln(2)}{60*kd}$$

NB refers to no binding observed under the conditions of the experiment.

Results and Conclusions

As shown in Table 7, at 25° C., all of the 17 anti-IsdB× anti-C1q antibodies of the disclosure bound to hC1q with $K_D$ values ranging from 11.4 pM-2.12 nM. As shown in Table 8, at 25° C., all of the 17 anti-IsdB× anti-C1q antibodies of the disclosure bound to IsdB-6xHis with $K_D$ values ranging from 1.70 nM-12.3 nM. As shown in Table 9, at 37° C., all of the 17 anti-IsdB× anti-C1q antibodies of the disclosure bound to hC1q with $K_D$ values ranging from 50.1 pM-5.01 nM. As shown in Table 10, at 37° C., all of the 17 anti-IsdB× anti-C1q antibodies of the disclosure bound to IsdB-6xHis with $K_D$ values ranging from 3.33 nM to 21.5 nM. Binding of hC1q and IsdB-6xHis to isotype (negative) control antibody (REGN1932) was not observed under the experimental conditions described above.

TABLE 7

Biacore kinetics of hC1q binding to C1q arm of anti-IsdB × anti-C1q bispecific antibodies at 25° C.

| Antibody ID | $k_a$ (Ms$^{-1}$) | $k_d$ (s$^{-1}$) | $K_D$ (Molar) | $t_{1/2}$ (min) |
|---|---|---|---|---|
| H1H20631D | 7.24E+06 | 1.65E-03 | 2.28E-10 | 7.01 |
| H1H20632D | 1.08E+07 | 3.18E-03 | 2.94E-10 | 3.64 |
| H1H20633D | 1.28E+07 | 3.48E-03 | 2.71E-10 | 3.32 |
| H1H20634D | 1.00E+07 | 2.27E-04 | 2.26E-11 | 50.9 |
| H1H20635D | 1.46E+07 | 4.52E-03 | 3.09E-10 | 2.56 |
| H1H20636D | 4.81E+06 | 1.02E-02 | 2.12E-09 | 1.14 |
| H1H20637D | 8.01E+06 | 1.24E-02 | 1.54E-09 | 0.93 |
| H1H20638D | 4.01E+06 | 5.11E-03 | 1.28E-09 | 2.26 |
| H1H20639D | 9.35E+06 | 6.12E-03 | 6.55E-10 | 1.89 |
| H1H20640D | 1.88E+07 | 6.87E-04 | 3.65E-11 | 16.8 |
| H1H20641D | 4.38E+06 | 6.80E-04 | 1.54E-10 | 17.1 |
| H1H20642D | 1.72E+07 | 1.96E-04 | 1.14E-11 | 58.9 |
| H1H20643D | 9.94E+06 | 1.30E-02 | 1.31E-09 | 0.89 |
| H1H20644D | 2.69E+07 | 6.24E-03 | 2.32E-10 | 1.85 |
| H1H20645D | 2.86E+07 | 4.52E-03 | 1.58E-10 | 2.56 |
| H1H20646D | 1.76E+07 | 4.87E-03 | 2.78E-10 | 2.37 |
| H1H20647D | 9.25E+06 | 3.40E-03 | 3.68E-10 | 3.39 |
| REGN1932 | NB | NB | NB | NB |

TABLE 8

Biacore kinetics of IsdB-6 × His binding to IsdB arm of anti-IsdB × anti-C1q bispecific antibodies at 25° C.

| Antibody ID | $k_a$ (Ms$^{-1}$) | $k_d$ (s$^{-1}$) | $K_D$ (Molar) | $t_{1/2}$ (min) |
|---|---|---|---|---|
| H1H20631D | 1.15E+05 | 2.70E-04 | 2.36E-09 | 42.8 |
| H1H20632D | 1.15E+05 | 2.55E-04 | 2.21E-09 | 45.2 |
| H1H20633D | 1.21E+05 | 2.47E-04 | 2.04E-09 | 46.9 |
| H1H20634D | 1.12E+05 | 2.96E-04 | 2.65E-09 | 39.0 |
| H1H20635D | 1.20E+05 | 2.04E-04 | 1.70E-09 | 56.6 |
| H1H20636D | 7.58E+04 | 3.78E-04 | 4.98E-09 | 30.6 |
| H1H20637D | 5.01E+04 | 4.68E-04 | 9.34E-09 | 24.7 |
| H1H20638D | 4.62E+04 | 4.98E-04 | 1.08E-08 | 23.2 |
| H1H20639D | 4.98E+04 | 5.62E-04 | 1.13E-08 | 20.5 |
| H1H20640D | 5.91E+04 | 5.53E-04 | 9.36E-09 | 20.9 |
| H1H20641D | 7.28E+04 | 4.38E-04 | 6.02E-09 | 26.4 |
| H1H20642D | 6.07E+04 | 5.01E-04 | 8.26E-09 | 23.0 |
| H1H20643D | 5.89E+04 | 5.55E-04 | 9.42E-09 | 20.8 |
| H1H20644D | 5.03E+04 | 5.54E-04 | 1.10E-08 | 20.8 |
| H1H20645D | 5.54E+04 | 5.51E-04 | 9.95E-09 | 21.0 |
| H1H20646D | 4.45E+04 | 4.33E-04 | 9.74E-09 | 26.7 |
| H1H20647D | 4.60E+04 | 5.65E-04 | 1.23E-08 | 20.4 |
| REGN1932 | NB | NB | NB | NB |

TABLE 9

Biacore kinetics of hC1q binding to C1q arm of anti-IsdB × anti-C1q bispecific antibodies at 37° C.

| Antibody ID | $k_a$ (Ms$^{-1}$) | $k_d$ (s$^{-1}$) | $K_D$ (Molar) | $t_{1/2}$ (min) |
|---|---|---|---|---|
| H1H20631D | 1.16E+07 | 2.22E-03 | 1.93E-10 | 5.19 |
| H1H20632D | 4.99E+07 | 8.71E-03 | 1.75E-10 | 1.33 |
| H1H20633D | 2.61E+07 | 1.27E-02 | 4.87E-10 | 0.91 |
| H1H20634D | 7.86E+06 | 4.03E-04 | 5.13E-11 | 28.7 |
| H1H20635D | 2.41E+07 | 1.74E-02 | 7.23E-10 | 0.66 |
| H1H20636D | 6.57E+06 | 1.79E-02 | 2.73E-09 | 0.64 |
| H1H20637D | 1.75E+07 | 4.07E-02 | 2.33E-09 | 0.28 |
| H1H20638D | 5.53E+06 | 1.10E-02 | 1.98E-09 | 1.05 |
| H1H20639D | 1.29E+07 | 8.59E-03 | 6.64E-10 | 1.34 |
| H1H20640D | 1.09E+07 | 1.51E-03 | 1.39E-10 | 7.67 |
| H1H20641D | 1.50E+06 | 2.70E-04 | 1.80E-10 | 42.9 |
| H1H20642D | 8.23E+06 | 4.12E-04 | 5.01E-11 | 28.0 |
| H1H20643D | 8.13E+06 | 4.07E-02 | 5.01E-09 | 0.28 |
| H1H20644D | 2.98E+07 | 2.76E-02 | 9.24E-10 | 0.42 |
| H1H20645D | 3.60E+07 | 3.17E-02 | 8.80E-10 | 0.36 |
| H1H20646D | 9.91E+06 | 1.29E-02 | 1.30E-09 | 0.90 |
| H1H20647D | 1.31E+07 | 5.76E-03 | 4.39E-10 | 2.00 |
| REGN1932 | NB | NB | NB | NB |

TABLE 10

Biacore kinetics of IsdB-6 × His binding to IsdB arm of anti-IsdB × anti-C1q bispecific antibodies at 37° C.

| Antibody ID | $k_a$ (Ms$^{-1}$) | $k_d$ (s$^{-1}$) | $K_D$ (Molar) | $t_{1/2}$ (min) |
|---|---|---|---|---|
| H1H20631D | 1.63E+05 | 5.57E-04 | 3.43E-09 | 20.7 |
| H1H20632D | 1.54E+05 | 5.27E-04 | 3.41E-09 | 21.9 |
| H1H20633D | 1.59E+05 | 5.40E-04 | 3.41E-09 | 21.4 |
| H1H20634D | 1.50E+05 | 5.73E-04 | 3.81E-09 | 20.2 |
| H1H20635D | 1.56E+05 | 5.20E-04 | 3.33E-09 | 22.2 |
| H1H20636D | 8.28E+04 | 1.44E-03 | 1.74E-08 | 8.04 |
| H1H20637D | 8.51E+04 | 1.49E-03 | 1.74E-08 | 7.78 |
| H1H20638D | 8.09E+04 | 1.44E-03 | 1.78E-08 | 8.03 |
| H1H20639D | 8.02E+04 | 1.48E-03 | 1.85E-08 | 7.81 |
| H1H20640D | 8.28E+04 | 1.42E-03 | 1.72E-08 | 8.13 |
| H1H20641D | 9.59E+04 | 1.41E-03 | 1.47E-08 | 8.19 |
| H1H20642D | 8.46E+04 | 1.41E-03 | 1.67E-08 | 8.19 |
| H1H20643D | 7.99E+04 | 1.48E-03 | 1.85E-08 | 7.81 |
| H1H20644D | 8.25E+04 | 1.50E-03 | 1.82E-08 | 7.70 |
| H1H20645D | 8.12E+04 | 1.55E-03 | 1.91E-08 | 7.43 |
| H1H20646D | 8.07E+04 | 1.50E-03 | 1.85E-08 | 7.72 |
| H1H20647D | 7.15E+04 | 1.54E-03 | 2.15E-08 | 7.51 |
| REGN1932 | NB | NB | NB | NB |

Example 5 Blocking ELISA

Complement component C1q is a circulating hexamer that recognizes and binds to immunoglobulin complexed to antigen, thus initiating the complement cascade. Anti-C1q antibodies have been isolated and subsequently engineered as bispecific antibodies with dual binding to human C1q and IsdB, an iron-regulated surface determinant protein B of *Staphylococcus aureus* evolved for scavenging iron from hemoglobin. The ability of anti-IsdB× anti-C1q bispecific antibodies to block the binding of native human complement component C1q to its natural ligands, human IgG1, human IgG2, human IgG3 and human IgM, was measured using competition sandwich ELISA assays.

Methods

The native human complement component C1q protein purified from human serum was purchased from Quidel and biotin-labeled (biot-hC1q). Human IgG1 kappa (hIgG1-k, Sigma Aldrich), human IgG2 kappa (hIgG2-k, EMD Millipore), human IgG3 kappa (hIgG3-k, EMD Millipore) and human IgM whole molecule (Jackson ImmunoResearch)

were purified from human plasma or urine. As a negative isotype control for the anti-IsdB× anti-C1q bispecific antibodies, an anti-Fel d 1 human IgG1 antibody (REGN 1932) was included for background binding to the coated immunoglobulins. The antibodies tested are shown in Table 6.

Experiments were carried out using the following procedure. Human immunoglobulins were coated separately at a concentration of 2 μg/mL for hIgG1-k, hIgG2-k, hIgG3-k or 5 μg/mL for hIgM in PBS on a 96-well microtiter plate overnight at 4° C. Nonspecific binding sites were subsequently blocked using a 0.5% (w/v) solution of BSA in PBS. On another microtiter plate, a constant amount of biot-hC1q protein (30 pM for hIgG1-k, hIgG3-k blocking or 6 nM for hIgG2-k, hIgM blocking) was mixed with anti-IsdB× anti-C1q bispecific antibodies or an isotype control antibody at range of concentrations (508 fM-30 nM for hIgG1-k, hIgG3-k blocking or 10 pM-600 nM for hIgG2-k, hIgM blocking). Constant concentrations of biot-hC1q for antibody inhibition assay were selected from the approximate midway point within the linear portion of biot-hC1q individual binding curves to plate-coated hIgG1-k, hIgG2-k, hIgG3-k, or hIgM."

A sample with no constant hC1q was included to determine background signal and solutions with no antibody, but containing 30 pM or 6 nM biot-hC1q protein were also tested to measure constant only binding signal. The antibody-protein complexes with 30 pM constant concentration of biot-hC1q protein were transferred to microtiter plates coated with hIgG1-k or hIgG3, and antibody-protein complexes with 6 nM constant concentration of biot-hC1q were transferred to hIgG2-k or hIgM coated plates. After one hour incubation at room temperature, the wells were washed, and plate-bound biot-hC1q was detected with streptavidin conjugated with horseradish peroxidase (Thermo Scientific). The plate was then developed using TMB substrate solution (BD Biosciences) according to manufacturer's recommendation and absorbance at 450 nm was measured on a Victor X4 plate reader (PerkinElmer).

Data analysis was performed using a sigmoidal dose-response model within Prism™ software (GraphPad). The calculated $IC_{50}$ value, defined as the concentration of antibody required to reduce 50% of C1q binding to immunoglobulins, was used as an indicator of blocking potency. Percent blockade at maximum concentration of the antibody tested in each assay was calculated. In the calculation, binding signal of the sample of 30 pM or 6 nM of biot-hC1q without the presence of the antibody was referenced as 100% binding or 0% blocking; and the background signal of the sample of buffer without biot-hC1q or the antibody was referenced as 0% binding or 100% blocking.

Results and Conclusions

The blocking results are summarized in Table 11 with antibodies organized in three groups based on their ability to block C1q binding to individual or multiple coating surfaces. The % blockade is reported for all antibodies and calculated at the highest concentration tested in each assay as indicated in the column titles. Negative maximum blocking % indicates an increase of biot-hC1q binding detected in the presence of antibody. $IC_{50}$ values are shown only for antibodies blocking >50% of C1q binding to hIgG1-k, hIgG2-k, IgG3-k or IgM and minus signs designate antibodies blocking <50% at the highest tested concentration. $IC_{50}$ values are reported as inconclusive (INC) for antibodies with inhibition curves unable to fit Prism™ software 4-parameter logistic equation. Nine of the seventeen anti-IsdB× anti-C1q bispecific antibodies of the disclosure tested were identified as blocking >50% biot-hC1q protein binding to hIgG1-k, hIgG2-k, hIgG3-k and hIgM ligands. These anti-IsdB× anti-C1q bispecific antibodies blocked 30 pM biot-hC1q binding to hIgG1-k and hIgG3-k and 6 nM biot-C1q binding to hIgG2-k and hIgM with IC50 values ranging from 110 pM to 83 nM and % blockade ranging from 53% to 99%.

TABLE 11

| | Bispecific Ab blocking of 30 pM biot-hC1q | | | | Bispecific Ab blocking of 6 nM biot-hC1q | | | |
|---|---|---|---|---|---|---|---|---|
| | Plate-coated hIgG1-k | | Plate-coated hIgG3-k | | Plate-coated hIgG2-k | | Plate-coated hIgM | |
| Bispecific Ab | $IC_{50}$ (M) | % Blockad with 30 nM bispecific Ab | $IC_{50}$ (M) | % Blockade with 30 nM bispecific Ab | $IC_{50}$ (M) | % Blockade with 600 nM bispecific Ab | $IC_{50}$ (M) | % Blockade with 600 nM bispecific Ab |
| Blocked > 50% in all assay formats | | | | | | | | |
| H1H20632D | INC | 90 | 8.3E−08 | 86 | 2.3E−08 | 88 | 1.8E−08 | 97 |
| H1H20633D | 1.6E−09 | 93 | 4.8E−09 | 84 | 8.2E−09 | 79 | 6.4E−09 | 96 |
| H1H20634D | 2.8E−10 | 96 | 9.6E−10 | 99 | 4.2E−09 | 92 | 3.8E−09 | 97 |
| H1H20635D | INC | 87 | INC | 53 | 1.6E−08 | 84 | 1.2E−08 | 93 |
| H1H20640D | 2.2E−10 | 86 | 1.1E−09 | 92 | 7.7E−09 | 79 | 5.1E−09 | 79 |
| H1H20642D | 1.1E−10 | 71 | 3.7E−10 | 96 | 5.0E−09 | 80 | 3.9E−09 | 72 |
| H1H20645D | 8.4E−10 | 94 | 5.3E−09 | 87 | 1.8E−08 | 87 | 1.3E−08 | 95 |
| H1H20646D | 1.3E−09 | 91 | 5.4E−09 | 84 | 2.0E−08 | 83 | 1.4E−08 | 94 |
| H1H20647D | 9.0E−09 | 85 | INC | 60 | 3.2E−08 | 80 | 2.5E−08 | 91 |
| Blocked > 50% in some assay formats | | | | | | | | |
| Blocked > 50% on plate-coated hIgG1-k, hIgG2-k, hIgG3-k | | | | | | | | |
| H1H20631D | 8.8E−09 | 78 | INC | 51 | 2.1E−08 | 78 | — | 38 |
| Blocked > 50% on plate-coated hIgG1-k, hIgG2-k, hIgGM | | | | | | | | |
| H1H20639D | INC | 64 | — | 33 | 7.0E−08 | 82 | 4.2E−08 | 86 |
| H1H20643D | 7.1E−08 | 78 | — | 42 | INC | 70 | 3.3E−08 | 95 |
| H1H20644D | 2.4E−08 | 66 | — | 36 | 6.3E−08 | 81 | 4.3E−08 | 75 |

TABLE 11-continued

| | Bispecific Ab blocking of 30 pM biot-hC1q | | | | Bispecific Ab blocking of 6 nM biot-hC1q | | | |
|---|---|---|---|---|---|---|---|---|
| | Plate-coated hIgG1-k | | Plate-coated hIgG3-k | | Plate-coated hIgG2-k | | Plate-coated hIgM | |
| Bispecific Ab | $IC_{50}$ (M) | % Blockad with 30 nM bispecific Ab | $IC_{50}$ (M) | % Blockade with 30 nM bispecific Ab | $IC_{50}$ (M) | % Blockade with 600 nM bispecific Ab | $IC_{50}$ (M) | % Blockade with 600 nM bispecific Ab |
| Blocked > 50% on plate-coated IgG2-k and hIgM | | | | | | | | |
| H1H20637D | — | −3 | — | −2 | 1.0E−07 | 70 | 7.1E−08 | 88 |
| Blocked < 50% in all assay formats | | | | | | | | |
| H1H20636D | — | −29 | — | −11 | — | 20 | — | 11 |
| H1H20638D | — | −30 | — | −25 | — | 33 | — | 28 |
| H1H20641D | — | −17 | — | −13 | — | 19 | — | 14 |
| Isotype control antibody | | | | | | | | |
| Human IgG1 isotype control antibody | — | 6 | — | 10 | — | 30 | — | 10 |

At the highest concentration of antibody tested, five of the seventeen anti-IsdBx anti-C1q bispecific antibodies blocked >50% biot-hC1q binding to only some of the hC1q ligands tested. One of these antibodies (H1H20631D) blocked 30 pM biot-hC1Q binding to hIgG1-k and hIgG3-k and 6 nM biot-hC1q binding to hIgG2-k with $IC_{50}$ values ranging from 8.8 nM to 21 nM and % blockade from 51% to 78%. This anti-IsdBx anti-C1q bispecific antibody at concentration of 200 nM blocked 6 nM biot-hC1q binding to hIgM with % blockade of 67%, but at highest tested concentration of 600 nM it blocked biot-hC1q binding to hIgM with % blockade of 38%. Three antibodies (H1H20639D, H1H20643D, and H1H20644D) blocked >50% only for 30 pM biot-C1q binding to hIgG1-k and 6 nM biot-hC1q binding to hIgG2-k and hIgM with $IC_{50}$ value ranging from 24 nM to 71 nM and % blockade from 64% to 95%. Another antibody (H1H20637D) blocked >50% only for 6 nM biot-hC1q binding to hIgG2-k and hIgM with $IC_{50}$ values ranging from 71 nM to 100 nM and % blockade between 70% and 88%.

Three of the seventeen anti-IsdBx anti-C1q bispecific antibodies (H1H20636D, H1H20638D, H1H20641D) and the irrelevant isotype control antibody blocked <50% of biot-hC1q binding to hIgG1-k, hIgG2-k, hIgG3-k and hIgM.

The blocking of binding of human C1q to antibodies by the bispecific antibody indicates that most of the bispecific antibodies at least partially block binding of C1q to sites on immunoglobulin molecules.

Example 6 Classical Pathway Hemolysis Assay

The complement system is a group of proteins that when activated lead to target cell lysis and facilitates phagocytosis through opsonization. Complement component C1q is a 410 kDa protein which forms a hexamer containing 1 stalk and 6 stems/heads. Each stem/head contains three polypeptides (A, B, C). C1q A, B, C proteins are 245, 253, and 245 aa in length, respectively. Each chain has an N-terminus region containing a cysteine residue followed by a collagen-like regions (CLR) and a C-terminus (globular head region). C1q forms a complex with two molecules of C1r and two molecules of C1s, referred to as C1 complex.

Complement is activated through a series of proteolytic steps which are activated by three major pathways: the Classical Pathway (CP), which is typically activated by immune-complexes, the Alternative Pathway (AP) that can be induced by unprotected cell surfaces, and the Mannose Binding Lectin (MBL) pathway. The Classical Pathway is initiated by $C1q/r_2/s_2$ binding to the Fc region of IgM and IgG or directly to a pathogen surface, leading to autoactivation of serine protease C1r which activates serine protease C1s, which in turns cleaves/activates C2 and C4, which then leads to cleavage of C3 and C5, ultimately resulting in the generation of membrane attack complex (MAC) and cell lysis.

The Classical Pathway (CP) assay is a screening assay for the activation of the classical complement pathway, which is sensitive to the decrease, absence, and/or inactivity of any component of the pathway. The CP assay tests the functional capability of serum complement components of the classical pathway to lyse sheep red blood cells (SRBC) pre-coated with rabbit anti-sheep red blood cell antibody (hemolysin). When antibody-coated SRBC are incubated with test serum, the Classical Pathway of complement is activated and hemolysis results. If a complement component (eg. C1q) is absent, the percent hemolysis activity will be zero; if one or more components of the classical pathway are decreased, the CP activity will be decreased (Giclas PC 1994). This assay is used for characterization and screening of anti-IsdBx anti-C1q antibodies.

Methods

Desired number of sheep SRBCs were washed in GVB++ buffer (Gelatin Veronal Buffer with Ca and Mg from CompTech) and resuspended at $1 \times 10^9$ cells/mL. To sensitize the SRBCs, a total of $1 \times 10^9$/mL of SRBC cells were mixed with equal volume of the 1:50 diluted rabbit anti-sheep hemolysin (1.5 mg/mL) at 37° C. for 20 minutes (final cell concentration of SRBC; $5 \times 10^8$ cells/mL and hemolysin at 0.75 mg/mL). Sensitized SRBCs were diluted to $2 \times 10^8$ cells/mL in GVB++ buffer prior to using in hemolysis assay. C1q depleted human serum was diluted from 100% to 4% with GVB++ buffer. Human C1q was diluted to 312 pM in GVB++ buffer. Test antibodies were prepared in the range 83.33 nM to 0.041 nM in GVB++ buffer.

A total of 75 uL of each of the test antibodies was combined with 5 uL of human C1q, for 80 uL total volume, where the final antibody concentration range became 78.13 nM to 0.038 nM and C1q was at fixed concentration of 19.5 pM. Test antibodies were bispecific antibodies: H1H20631D, H1H20632D, H1H20633D, H1H20634D, H1H20635D, H1H20636D, H1H20637D, H1H20638D, H1H20639D, H1H20640D, H1H20641D, and H1H20642D. From this 80 uL mixture, 50 uL were then transferred to a fresh 96-well plate and mixed with 50 uL of 4% C1q depleted human serum. In the 100 uL total volume, the final antibody concentration ranged from 39.1 nM to 0.019 nM, C1q was at fixed concentration of 9.75 pM and C1q depleted serum was at 2% concentration. Immediately, 100 uL of sensitized SRBCs (at 2×10$^8$ cells/mL) were added, for a total volume of 200 uL, and incubated for 1 hr at 37° C. After the incubation time, cells were spun down by centrifugation at 1250×g at 4° C. A total of 100 uL of the supernatant was transferred to a fresh 96-well flat bottom plate and read at 412 nm on a Molecular Devices Spectramax M5 microplate reader and SoftMax Pro software.

Additionally, a human C1q dose response in C1q depleted human serum was determined as follows. A 2× stock of C1q depleted human serum was made by diluting serum from 100% to 4% in GVB++ buffer. A 2× stock of human C1q protein was diluted from 6.1×10$^{-8}$ M to 7.2×10$^{-15}$ M in GVB++ buffer. Total of 50 uL of the 2× stock of C1q depleted serum was added to 50 uL of the 2× stock of C1q made over a range of dilutions, for a total of 100 uL, where the final C1q depleted human serum concentration was 2% and the final C1q concentration ranged from 3.05×10$^{-8}$ M to 3.6×10$^{-15}$ M. Immediately, 100 uL of sensitized SRBCs (at 2×10$^8$ cells/mL) were added, for a total volume of 200 uL, and incubated for 1 hr at 37° C. After the incubation time, cells were spun down by centrifugation at 1250×g at 4° C. and supernatant was read at 412 nm as described above.

The hemolytic activity was calculated at final serum concentration of 2% as follows: First the OD412 of GVB++ diluent alone (no SRBCs) was subtracted from all data, then the OD412 of background cell lysis (i.e. cells incubated in GVB++ buffer only, without any serum) was subtracted from all data. Then $OD_{412}$ of all experimental samples was divided by the $OD_{412}$ at Maximum cell lysis (cells treated with 100 uL water) and then multiplied by 100.

To summarize, the percentage of hemolysis was calculated with the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

The results, expressed as % hemolysis were analyzed using nonlinear regression (4-parameter logistics) with Prism 6 software (GraphPad) to obtain $IC_{50}$ values. 0-100% inhibition of hemolysis by bispecific antibodies or isotype control is based on the difference in % hemolysis between the lowest and highest antibody concentration, divided by the difference in % hemolysis between the lowest antibody concentration and the bottom of the C1q dose response, multiplied by 100. Data represented are single points (duplicates not run).

Eleven anti-IsdB× anti-C1q bispecific antibodies of this disclosure were tested in a Classical Pathway (CP) hemolysis assay. Seven bispecific antibodies; H1H20631D, H1H20632D, H1H20633D, H1H20634D, H1H20635D, H1H20640D, H1H20642D are strong blockers of CP hemolysis activity. One bispecific antibody H1H20637D is a moderate blocker (at highest tested concentration of 40 nM); and three bispecific antibodies H1H20636D, H1H20638D and H1H20641D are non-blockers of CP hemolysis activity. (See Table 12 below.)

To conclude, 7 out of 11 antibodies of this disclosure block classical complement pathway activation.

TABLE 12

| | Anti-IsdB PID Number | Anti-C1q PID Number | $IC_{50}$ (M) | % inhibition | Conclusion |
|---|---|---|---|---|---|
| Anti-IsdB × anti-C1q Bispecific antibody, AbPID ||||||
| H1H20631D | H1H20295P2VH | H1xH17736P2VH | 2.67E−09 | 100 | strong blocker |
| H1H20632D | H1H20295P2VH | H1xH17738P2VH | 1.78E−09 | 100 | strong blocker |
| H1H20633D | H1H20295P2VH | H1xH18392P2VH | 1.42E−09 | 100 | strong blocker |
| H1H20634D | H1H20295P2VH | H1xH18394P2VH | 5.02E−10 | 100 | strong blocker |
| H1H20635D | H1H20295P2VH | H1xH18395P2VH | 8.88E−09 | 97 | strong blocker |
| H1H20636D | H1H20318P2VH | H1xH17773P2VH | non-blocker | 0 | non-blocker |
| H1H20637D | H1H20318P2VH | H1xH17779P2VH | Inconclusive | 50 | moderate blocker |
| H1H20638D | H1H20318P2VH | H1xH17781P2VH | non-blocker | 24 | non-blocker |
| H1H20640D | H1H20318P2VH | H1xH17756P2VH | 4.27E−10 | 99 | strong blocker |
| H1H20641D | H1H20318P2VH | H1xH17758P2VH | non-blocker | 0 | non-blocker |
| H1H20642D | H1H20318P2VH | H1xH17760P2VH | 1.06E−10 | 99 | strong blocker |
| REGN# ||||||
| REGN1932 | n/a | n/a | non-blocker | 0 | non-blocker |

Example 7 Complement Dependent Cytotoxicity Assay

A classical complement dependent cytotoxicity (CDC) assay was developed to evaluate the capacity of the bispecific antibodies of the disclosure to block CDC mediated by human Complement component C1q (hC1q). Daudi cells, a human B cell line expressing CD20, an anti-CD20 antibody, and normal human serum as a source of complement components were used. Therapeutic anti-CD20 antibodies against the B-cell specific cell-surface antigen CD20, have been shown to lead to CDC of B-cells (Glennie et al., Mechanisms of killing by anti-CD20 monoclonal antibodies, Molecular Immunology, Volume 44, Issue 16, September 2007, Pages 3823-3837) and CDC assay using cell lines expressing CD20 has been described previously (Flieger et al., Mechanism of cytotoxicity induced by chimeric mouse human monoclonal antibody IDEC-C2B8 in CD20-expressing lymphoma cell lines, Cellular Immunology, Volume 204, Issue 1, Aug. 25 2000, Pages 55-63).

Methods

For the bioassay, Daudi cells were seeded onto a 96-well assay plates at 10,000 cells/well in RPMI containing 10% Heat inactivated FBS, penicillin/streptomycin, L-glutamine, sodium pyruvate and Non-Essential Amino Acids (RPMI Complete media). To measure CDC, the anti-CD20 antibody was diluted 1:3 from 100 nM to 2 pM (including a control sample containing no antibody) and incubated with cells for 10 minutes at 25° C. followed by addition of 1.67% complement preserved human serum. To test inhibition of CDC, anti-IsdB× anti-hC1q bispecific antibodies, anti-IsdB conventional antibodies, an anti-C1q antibody, or an isotype control antibody, were diluted 1:3 from either 750 nM to 13 pM or 611 nM to 10 pM (including a control sample containing no antibody) and incubated with 1.67% serum for 30 minutes. Ten minutes prior to addition of antibodies with serum to cells, the anti-CD20 antibody was added to cells at 2 nM. At the conclusion of the incubation with the anti-CD20 antibody, the antibody plus serum mixture was added to cells. Cytotoxicity was measured after 3.5 hours of incubation at 37° C. and 5% $CO_2$, followed by a 15-minute incubation at 25° C. and subsequent addition of CytoTox-Glo™ reagent (Promega, # G9292). CytoTox-Glo™ is a luminescence-based reagent that measures cell killing such that increased luminescence is observed with increased cytotoxicity (measured in relative light units, RLUs). Untreated cells in control wells were lysed by treatment with 166.7 ug/mL digitonin immediately after addition of CytoTox-Glo™ reagent to determine maximal killing of cells. Plates were read for luminescence by a Victor X instrument (Perkin Elmer) 15 minutes following the addition of CytoTox-Glo™.

The percentage of cytotoxicity was calculated with the RLU values by using the following equation:

$$\% \text{ Cytoxicity} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the luminescence from the cells treated with media and serum alone without any anti-CD20 antibody and the "maximum cell lysis" is the luminescence from the cells treated with 166.7 ug/mL digitonin. The results, expressed as % cytotoxicity were analyzed using nonlinear regression (4-parameter logistics) with Prism 5 software (GraphPad) to obtain $EC_{50}$ and $IC_{50}$ values. % inhibition of antibodies was calculated using the following equation:

$$\% \text{ Inhibition} = 100 \times \frac{\text{Cytoxicity}_{Baseline} - \text{Cytoxicity}_{Inhibition}}{\text{Cytoxicity}_{Baseline} - \text{Cytoxicity}_{Background}}$$

In this equation "Cytotoxicity$_{Baseline}$" is the % Cytotoxicity from the cells treated with 2 nM of anti-CD20 antibody alone, "Cytotoxicity$_{Inhibition}$" is the minimum % Cytotoxicity value from a dose response of a particular inhibiting antibody with 2 nM anti-CD20 antibody, and "Cytotoxicity$_{Background}$" is the % Cytotoxicity from cells without any antibodies. In the above equation, all conditions contain 1.67% serum.

Seventeen anti-IsdB× anti-C1q bispecific antibodies of the disclosure were tested for their ability to inhibit C1q in the CDC assay using Daudi cells with 1.67% human sera and 2 nM anti-CD20 antibody. As shown in Table 13, eleven of the 17 bispecific antibodies showed at least 94% inhibition of C1q mediated CDC with $IC_{50}$ values ranging from 10 nM to greater than 100 nM. Five of the remaining bispecific antibodies were blockers with $IC_{50}$ values greater than 100 nM, and maximum inhibition (at 750 nM antibody) ranging from 33% to 88%. One of the bispecific antibodies (H1H20636D) along with conventional anti-IsdB antibodies, which contained the anti-IsdB binding region of the bispecific antibodies, did not show inhibition of hC1q mediated CDC. Human IgG1 isotype control antibody, Control mAb1, also did not demonstrate any significant inhibition of CDC. A commercial anti-C1q monoclonal antibody (Quidel, A201) showed >99% inhibition of CDC with an $IC_{50}$ value of 3.0 nM. Anti-CD20 antibody showed CDC of Daudi cells with 1.67% human serum with an $EC_{50}$ value of 892 pM and a maximum % Cytotoxicity at 100 nM of 62%.

TABLE 13 anti-IsdB × anti-C1q bispecific antibody inhibition of CDC of Daudi cells with 1.67% human serum and 2 nM anti-CD20 antibody:

| Anti-IsdB × anti-C1q Bispecific Antibody | IC50 [M] (Max % Inhibition)* |
|---|---|
| H1H20631D | >1.0E−07 (94%) |
| H1H20632D | 2.3E−07 |
| H1H20633D | 1.7E−08 |
| H1H20634D | 1.9E−08 |
| H1H20635D | 2.8E−08 |
| H1H20636D | No inhibition |
| H1H20637D | >1.0E−07 (67%) |
| H1H20638D | 1.0E−07 |
| H1H20639D | >1.0E−07 (70%) |
| H1H20640D | 1.1E−08 |
| H1H20641D | >1.0E−06 (33%) |
| H1H20642D | 1.0E−08 |
| H1H20643D | 3.7E−08 |
| H1H20644D | >1.0E−07 (88%) |
| H1H20645D | 3.4E−08 |
| H1H20646D | 5.4E−08 |
| H1H20647D | >1.0E−07 (82%) |
| H1H20295P2(anti IsdB) | No inhibition |
| H1H20318P2(anti IsdB) | No inhibition |
| a-C1q (Quidel, A201) | 3.0E−09 |
| Control mAb1 | No inhibition |

*Unless otherwise noted, all inhibition is ≥99%

Example 8 A: Binding of Anti-IsdB× Anti-C1q Bispecific Antibodies to *S. aureus* Wood 46

Binding of the anti-IsdB× anti-C1q bispecific antibodies to IsdB expressed on the surface of *S. aureus* was determined in an ELISA based format. In order to distinguish binding to IsdB from non-specific binding of antibody to protein A expressed by *S. aureus* (Lindmark et. al, J Immunol Methods, 1983 Aug. 12; 62(1):1-13), a protein A deficient strain of the bacteria, *S. aureus* Wood 46, was used in the assay.

Methods

Anti-IsdB× anti-C1q bispecific antibodies of this invention (H1H20631D, H1H20632D, H1H20633D, H1H20634D, H1H20635D, H1H20636D, H1H20637D, H1H20638D, H1H20639D, H1H20640D, H1H20641D, H1H20642D, H1H20643D, H1H20644D, H1H20645D, H1H20646D, H1H20647D) were tested for binding to *S. aureus* Wood 46 by ELISA. Briefly, *S. aureus* Wood 46 was grown in RPMI overnight, washed in PBS and adjusted to an $OD_{600}$ of 0.25. MaxiSorp 96 well microtiter plates were coated overnight with 100 µl of *S. aureus* culture per well. Plates were washed and blocked with 3% BSA. Titrations ranging from 0.14 nM-0.1 µM with 1:3 dilutions of anti-IsdB× anti-C1q bispecific antibodies, Control I, Control II, Control III and negative isotype control antibody were added to *S. aureus*-containing wells and incubated for 1 hour at 25° C. Anti-human HRP conjugated secondary antibody was added to washed plates. Luminescence reagents (SuperSignal Pico) were then added to the wells and signal was detected in a plate reader (Victor X3 plate reader, Perkin Elmer) immediately. Luminescence values were analyzed by a four-parameter logistic equation over a 7-point response curve (GraphPad Prism) to determine the binding $EC_{50}$ of the antibodies.

The control antibodies used in this study (Example 8A and 8B) include the following: Control I is an anti-IsdB hIgG1 antibody described in US2010/0166772 and designated CS-D7 (See also SEQ ID NO:1 and SEQ ID NO:2 in US2010/0166772). Control II is a bivalent antibody specific for IsdB prepared as described herein (Example 2, Table 3): antibody H1H20295P2 and HCVR/LCVR pair having amino acid sequence of SEQ ID NO:138/146. Control III is a bivalent antibody specific for IsdB prepared as described herein (Example 2, Table 3): H1H20318P2 and HCVR/LCVR pair having amino acid sequence of SEQ ID NO:154/162. Control II and Control III antibodies do not have an antigen-binding domain that binds to C1q. REGN1932 is a negative isotype control antibody specific for an antigen other than IsdB or C1q.

Results:

When assayed for their ability to bind *S. aureus* Wood 46 by ELISA, antibodies described in this invention displayed binding affinities ranging from $1.04 \times 10^{-9}$ M to $1.8 \times 10^{-8}$ M, while the Controls I-III displayed binding affinities ranging from $9.13 \times 10^{-11}$ M to $3.6 \times 10^{-9}$ M. Negative isotype control antibody did not bind to *S. aureus* Wood 46 (Table 14).

Example 8B: Anti-IsdB× Anti-C1q Bispecific Antibodies Dependent C1q Complement Deposition on *S. aureus* Cowan I C1q deposition potentiated by the anti-IsdB× anti-C1q bispecific antibodies on the surface of *S. aureus* Cowan I strain was determined in an ELISA based format by directly measuring the C1q deposited from human serum on the pathogen surface mediated by the bispecific antibodies.

Methods

Anti-IsdB× anti-C1q bispecific antibodies of this invention (H1H20631D, H1H20632D, H1H20633D, H1H20634D, H1H20635D, H1H20636D, H1H20637D, H1H20638D, H1H20639D, H1H20640D, H1H20641D, H1H20642D, H1H20643D, H1H20644D, H1H20645D, H1H20646D, H1H20647D) were tested for complement deposition on *S. aureus* Cowan I in an ELISA based assay format. Briefly, *S. aureus* Cowan I was grown in RPMI overnight, washed in PBS and adjusted to an $OD_{600}$ of 0.25. MaxiSorp 96 well microtiter plates were coated overnight with 100 µl of *S. aureus* culture per well. Plates were fixed with 2% paraformaldehyde and blocked with 3% BSA prior to addition of titrations ranging from 0.14 nM-0.1 µM with 1:3 dilutions of anti-IsdB× anti-C1q bispecific antibodies, Control I, Control II, Control III and isotype control antibodies for 1 hour at 25° C. After washing, 5% protein A/G adsorbed C1q depleted serum supplemented with 60 µg/mL purified human C1q was added for 1.5 hrs at 37° C. Goat anti-C1q antibody was added to detect C1q deposition, followed by donkey anti-goat HRP secondary antibody. Plates were washed in a plate washer in between each step. Luminescence reagents (SuperSignal Pico) were then added to the wells and signal was detected in a plate reader (Victor X3 plate reader, Perkin Elmer). Luminescence values were analyzed by a four-parameter logistic equation over a 7-point response curve (GraphPad Prism) to calculate the binding $EC_{50}$ of the antibodies.

Results

When assayed for their ability to promote C1q deposition on *S. aureus* Cowan I, all antibodies of the invention displayed $EC_{50}$ values ranging from $3.76 \times 10^{-12}$ M to $8.54 \times 10^{-9}$ M while no C1q deposition was measured with Control and negative isotype control (Table 14).

TABLE 14

Anti-IsdB × anti-C1q bispecific antibodies binding to *S. aureus* Wood 46 and C1q complement deposition on *S. aureus* Cowan I

| Antibody ID | Description | Binding to *S. aureus* Wood 46 EC50 (M) | C1q deposition on *S. aureus* Cowan I EC50 (M) |
|---|---|---|---|
| H1H20631D | anti-IsdB × anti-C1q bispecific | 1.263E−09 | 2.971E−10 |
| H1H20632D | anti-IsdB × anti-C1q bispecific | 1.08E−09 | 5.294E−10 |
| H1H20633D | anti-IsdB × anti-C1q bispecific | 1.307E−09 | 2.035E−10 |
| H1H20634D | anti-IsdB × anti-C1q bispecific | 1.038E−09 | Above assay range |

TABLE 14-continued

Anti-IsdB × anti-C1q bispecific antibodies binding to *S. aureus*
Wood 46 and C1q complement deposition on *S. aureus* Cowan I

| Antibody ID | Description | Binding to *S. aureus* Wood 46 EC50 (M) | C1q deposition on *S. aureus* Cowan I EC50 (M) |
|---|---|---|---|
| H1H20635D | anti-IsdB × anti-C1q bispecific | 1.958E−09 | 4.251E−10 |
| H1H20636D | anti-IsdB × anti-C1q bispecific | 9.521E−09 | 8.539E−09 |
| H1H20637D | anti-IsdB × anti-C1q bispecific | 1.129E−08 | 5.005E−09 |
| H1H20638D | anti-IsdB × anti-C1q bispecific | 1.039E−08 | 2.546E−09 |
| H1H20639D | anti-IsdB × anti-C1q bispecific | 1.332E−08 | 2.064E−09 |
| H1H20640D | anti-IsdB × anti-C1q bispecific | 1.802E−08 | 3.762E−12 |
| H1H20641D | anti-IsdB × anti-C1q bispecific | 1.035E−08 | 1.291E−09 |
| H1H20642D | anti-IsdB × anti-C1q bispecific | 8.572E−09 | 5.858E−12 |
| H1H20643D | anti-IsdB × anti-C1q bispecific | 1.006E−08 | 1.779E−09 |
| H1H20644D | anti-IsdB × anti-C1q bispecific | 1.258E−08 | 1.116E−09 |
| H1H20645D | anti-IsdB × anti-C1q bispecific | 1.186E−08 | 2.978E−10 |
| H1H20646D | anti-IsdB × anti-C1q bispecific | 1.294E−08 | 4.158E−10 |
| H1H20647D | anti-IsdB × anti-C1q bispecific | 7.3E−09 | 5.874E−10 |
| Control I (REGN3457) | anti-IsdB (COMP) hIgG1 | 9.127E−11 | No Deposition |
| Isotype Control (REGN1932) | IgG1 isotype control | No Binding | No Deposition |
| Control II (H1H20295P2) | anti-IsdB hIgG1 bivalent | 6.464E−10 | No Deposition |
| Control III (H1H20318P2) | anti-IsdB hIgG1 bivalent | 3.601E−09 | No Deposition |

Example 9A Functional Assay: Whole Blood
Bacterial Survival: *S. aureus* Survival in Whole
Human Blood and the Effects of Anti-IsdB×
Anti-C1q

*S. aureus* survival in whole human blood can be assessed in an ex vivo assay to explore the role of complement and immune effector cells to modulate bacterial growth (J Exp Med. 2009 Oct. 26; 206(11):2417-27). The activity of anti-IsdB× anti-C1q bispecific antibodies in modulating *S. aureus* survival is measured in this assay where the bispecific antibodies or control antibodies are added into whole blood and survival is assessed after 24 hours.

Methods

Anti-IsdB× anti-C1q bispecific antibodies of this invention (H1H20631D, H1H20632D, H1H20633D, H1H20634D, H1H20635D, H1H20636D, H1H20637D, H1H20638D, H1H20639D, H1H20640D, H1H20641D, H1H20642D, H1H20643D, H1H20644D, H1H20645D, H1H20646D, H1H20647D) were assessed for bactericidal activity against *S. aureus* Newman in a whole blood survival assay. Briefly, a culture of *S. aureus* Newman was grown in RPMI overnight, washed in PBS, and resuspended to a concentration of 1×10$^8$ colony forming units (CFU)/mL in PBS. In duplicates, 10 uL of the *S. aureus* suspension pre-mixed with 10 ug/mL test and control antibodies for 10 minutes was added to 100 uL of whole human blood (in sodium citrate as anti-coagulant with additional 500 nM dabigatran to prevent clot formation). The samples were incubated in 96 well plates at 37° C. with shaking (100 rpm) for 24 hours. After incubation, 100 ul of agglutination lysis buffer (PBS supplemented with 200U Streptokinase, 2 ug/mL RNase, 10 ug/mL DNase, 0.5% saponin, 100 ug trypsin per ml of PBS) was added to the samples and vigorously vortexed until the pellet disappeared. A total of 50 uL from each sample was serially diluted in PBS and plated onto LB agar plates for enumeration of CFUs.

The control antibodies used in this study (Example 9A and 9B) include the following: Control I is an anti-IsdB hIgG1 antibody described in US2010/0166772 and designated CS-D7 (See also SEQ ID NO:1 and SEQ ID NO:2 in US2010/0166772). Control II is a bivalent antibody specific for IsdB prepared as described herein (Example 2, Table 3): antibody H1H20295P2 and HCVR/LCVR pair having amino acid sequence of SEQ ID NO:138/146. Control III is a bivalent antibody specific for IsdB prepared as described herein (Example 2, Table 3): H1H20318P2 and HCVR/LCVR pair having amino acid sequence of SEQ ID NO:154/162. Control II and Control III antibodies do not have an antigen-binding domain that binds to C1q. REGN1932 is a negative isotype control antibody specific for an antigen other than IsdB or C1q.

Results

Results from two independent experiments are presented as percent survival of *S. aureus* after treatment with the bispecific or control antibodies are described here and summarized in Table 15. The overall growth in whole human blood in the absence of test antibody is normalized to 100%. Survival of *S. aureus* in control and negative isotype control antibodies was unaffected and ranged from 96-100%, while H1H20631D resulted in 29-42% survival and H1H20635D resulted in 35-42% survival. H1H20634D had more modest effects and resulted in 73-76% survival. The remaining bispecific antibodies did not alter survival of *S. aureus*.

TABLE 15

*S. aureus* Newman survival in whole human blood after treatment with anti-IsdB × anti-C1q bispecific antibody

| Antibody | Experiment 1 | Experiment 2 |
|---|---|---|
| | % survival of *S. aureus* compared to whole blood (no treatment, normalized to 100%) | |
| Blood + *S. aureus* (no treatment) | 100 | 100 |
| Isotype Control (REGN1932) | 99 | 100 |
| Control I (REGN3457) | 97 | 101 |
| Control II (H1H20295P2) | 99 | 97 |
| Control III (H1H20318P2) | 96 | 97 |
| H1H20631D | 29 | 42 |
| H1H20632D | 104 | 98 |
| H1H20633D | 101 | 90 |
| H1H20634D | 76 | 73 |
| H1H20635D | 35 | 42 |
| H1H20636D | 108 | 95 |
| H1H20637D | 101 | 101 |
| H1H20638D | 100 | 97 |
| H1H20639D | 97 | 98 |
| H1H20640D | 100 | 97 |
| H1H20641D | 95 | 97 |
| H1H20642D | 100 | 95 |
| H1H20643D | 99 | 96 |
| H1H20644D | 101 | 87 |
| H1H20645D | 102 | 90 |
| H1H20646D | 98 | 100 |
| H1H20647D | 97 | 99 |

Example 9B. *S. aureus* Survival in Whole Human Blood in the Presence of a C5 Blocking Antibody and Cytochalasin D In order to determine the mechanism of action of the anti-IsdB× anti-C1q bispecific antibody, a whole blood *S. aureus* survival assay described above was utilized. The C5 blocking antibody was used to determine if the reduction in survival was a result of opsonization by C4 or C3 breakdown products leading to increased uptake by immune effector cells or the membrane attack complex (downstream of C5). Cytochalasin D blocks actin polymerization and therefore prevents immune effector cells from engulfing the pathogen.
Methods The experiment was performed as described above with the following additions. A portion of the blood was pre-treated with 40 uM cytochalasin D or 5 uM C5 blocking Fab or 5 uM Fab control for 10 minutes at room temperature prior to addition to *S. aureus*. With the exception of the control (no antibody treatment) condition where *S. aureus* was pre-incubated with PBS, *S. aureus* was pre-incubated with 100 ug/mL H1H20631D for 10 minutes prior to the addition of untreated, C5 blocking Fab treated, control Fab treated or cytochalasin D treated whole human blood. As above, the samples were incubated in 96 well plates at 37° C. with shaking (100 rpm) for 24 hours. After incubation, 100 ul of agglutination lysis buffer was added to dissolve the blood clot and the surviving bacteria were plated on LB agar plates to determine CFUs.
Results After 24 hours, only 7% of the bacteria survived after treatment with H1H20631D compared to the no antibody control. The addition of the complement component protein 5; C5 blocking Fab increased survival to 91%; the control Fab did not interfere with the activity of H1H20631D in reducing bacterial survival (5%). However, blocking phagocytic activity of the white blood cells using cytochalasin D by inhibiting actin polymerization, does not appreciably improve *S. aureus* survival (12%). Taken together, these data suggest that the activity of the anti-IsdB× anti-C1q bispecific antibodies are primarily downstream of C5, notably the lytic activity of the membrane attack complex. The survival data is summarized in Table 16.

TABLE 16

*S. aureus* survival in whole human blood with anti-IsdB × anti-C1q bispecific antibody treatment in the presence of a C5 blocking antibody or cytochalasin D

| Antibody treatment | % survival of *S. aureus* |
|---|---|
| No antibody | 100 |
| H1H20631D | 7 |
| H1H20631D + C5 blocking Fab | 91 |
| H1H20631D + control Fab | 5 |
| H1H20631D + cytochalasin D | 12 |

Example 10 Determining Biological Activity of Anti-IsdB× Anti-C1q Antibodies in a Mouse Model of *S. aureus* Bacteremia

*S. aureus* is a major cause of bacteremia in patients, and these infections are often fatal. Mouse models of bacteremia have been developed by many laboratories using a variety of laboratory-adapted and clinical *S. aureus* isolates and in a variety of mouse backgrounds (O'Keeffe K M, et al, Infect Immun. 2015 September; 83(9):3445-57. Manipulation of Autophagy in Phagocytes Facilitates *Staphylococcus aureus* Bloodstream Infection.; Rauch et al, Infect Immun. 2012 October; 80(10):3721-32. Abscess formation and alpha-hemolysin induced toxicity in a mouse model of *Staphylococcus aureus* peritoneal infection.) to study the infection dynamics and effect of potential therapeutics. A bacteremia model was established to evaluate the activity of anti-IsdB× anti-C1q bispecific antibodies against *S. aureus* in both reducing bacterial burden and improving survival.
Methods Humanized C1q (C1q$^{Hu/Hu}$) mice were generated using human sequences for C1q globular head domains of C1QA, C1QB and C1QC along with overlapping mouse sequences that replaced the mouse C1q sequences in a mixed mouse strain background (High-throughput engineering of the mouse genome coupled with high-resolution expression analysis. *Nat. Biotech.* 21(6): 652-659). Resulting mice express chimeric C1q protein with human head, mouse stem and mouse stalk. C1q$^{Hu/Hu}$ mice were infected intraperitoneally with 1.7×10$^8$ colony forming units (CFUs) per mouse in a 200 ul volume of *S. aureus* Newman strain grown to log phase, OD$_{600}$≤1, in TSB at 37° C. and washed 3 times in PBS. Immediately following infection, mice were dosed with 100 ug of each individual antibody, Control II or isotype-matched antibody in a 100 ul volume, intraperitoneally. Mice were weighed daily until Day 3 post infection and change in weight was recorded. Mice were euthanized on Day 3 and kidneys were collected to determine organ burden. Briefly, kidneys were homogenized in 5.0 mL PBS using gentleMACS Octo Dissociator (Miltenyi Biotec) using program-E. Tissue homogenate was diluted in PBS and multiples of 10-fold serial dilutions were plated on LB agar plates and incubated at 37° C. overnight. Next day individual colonies were counted to determine bacterial burden at that time point post-infection and results were reported as CFUs/gram tissue.

To examine the effect of the anti-IsdB× anti-C1q bispecific antibodies on survival, mice were infected with 1.5×10$^8$ CFUs per mouse of *S. aureus* Newman and treated with test antibodies as described above. Controls were the isotype (negative) control and Control II: a bivalent antibody specific for IsdB prepared as described herein (Example 2, Table 3): antibody H1H20295P2 and HCVR/LCVR pair having amino acid sequence of SEQ ID NO:138/146. Instead of sacrificing the mice on Day 3, they were monitored until Day 18. Mice that lost 20% of their starting body weight were sacrificed and recorded as a death. The percentage of surviving animals was reported at the end of the study.

Results and Conclusions:

Bispecific anti-IsdB× anti-C1q antibodies, H1H20631D, H1H20633D, H1H20635D and H1H20636D were tested alongside a control antibody and an isotype control antibody for efficacy in reducing kidney burden in female C1q$^{Hu/Hu}$ mice (n=5). Compared to the infection control or mice treated with the isotype control antibody alone, where 9 logs of *S. aureus* CFUs were recovered from the kidneys on Day 3, a 4 log reduction in overall CFUs after treatment with H1H20631D and a 2 log reduction in CFUs after treatment with H1H20635D was observed. (See Table 17) Two bispecific antibodies H1H20633D and H1H20636D had no measurable effects on kidney bacterial loads.

TABLE 17

*S. aureus* Newman in kidneys on Day 3 treatment with 5 mg/kg anti-IsdB × anti-C1q

| AbPID | CFUs/g kidney | SD | Mice (n) |
|---|---|---|---|
| H1H20631D | 1.61E+05 | 2.61E+05 | 4 |
| H1H20633D | 3.38E+08 | 2.53E+08 | 4 |
| H1H20635D | 4.18E+07 | 6.82E+07 | 4 |
| H1H20636D | 3.41E+08 | 1.61E+08 | 4 |
| Control II | 3.83E+08 | 1.86E+08 | 5 |
| Isotype Control | 1.11E+09 | 1.15E+09 | 2 |
| Sham (PBS) | 1.42E+09 | 5.06E+07 | 3 |

As shown in Table 18, from Day 1 to Day 3, an 8.5% weight gain in mice treated with H1H20631D and 7.9% weight gain in mice treated with H1H20635D was recorded. Mice in all other test groups either maintained their weight loss or had very modest gains (negative isotype control and H1H20633D treated).

TABLE 18

Weight change in mice on Days 1-3 after treatment with 5 mg/kg anti-IsdB × anti-C1q bispecific antibodies

| AbPID | % weight change Day 1 | % weight change Day 2 | % weight change Day 3 |
|---|---|---|---|
| H1H20631D | −17.0 | −13.3 | −8.9 |
| H1H20633D | −16.4 | −14.3 | −13.8 |
| H1H20635D | −15.6 | −13.3 | −7.7 |
| H1H20636D | −15.4 | −17.1 | −16.5 |
| Control II | −16.5 | −18.2 | −16.0 |
| Isotype Control | −17.4 | −16.0 | −16.2 |
| Sham (PBS) | −13 | −12.8 | −13 |

Bispecific anti-IsdB× anti-C1q antibody, H1H20631D, was tested alongside a control antibody and a negative isotype control antibody for efficacy in a survival study in C1q$^{Hu/Hu}$ female mice (n=9). As shown in Table 19, at the end of the study, on Day 18 post infection, 100% of the mice treated with H1H20631D survived, in comparison to 56% of control or sham treated mice and 78% of the negative isotype control treated mice.

Taken together, the anti-IsdB× anti-C1q antibodies of this disclosure are efficacious at reducing kidney bacterial burden and improving survival in a humanized C1q mouse strain in a model of *S. aureus* bacteremia.

TABLE 19

Survival in mice treated with 5 mg/kg anti-IsdB × anti-C1q bispecific antibody

| AbPID | Survival at D18 post-infection (%) | Mice (n) |
|---|---|---|
| H1H20631D | 100 | 9 |
| Control II | 56 | 9 |
| Isotype Control | 78 | 9 |
| Sham (PBS) | 56 | 9 |

Example 11. C1q Cross-Competition on Anti-IsdB× Anti-C1q Bispecific mAbs

The anti-IsdB× anti-C1q bispecific antibodies described herein were tested for cross competition using a real time, label-free bio-layer interferometry (BLI) assay on an Octet HTX biosensor. The cross competition assay provides a determination of the bispecific antibodies that compete with one another for binding to human C1q.

Binding competition between anti-IsdB× anti-C1q bispecific antibodies for hC1q (Quidel) was determined using a real time, label-free bio-layer interferometry (BLI) assay on an Octet HTX biosensor (ForteBio/Pall Life Sciences). The experiments were performed at 25° C. in buffer comprised of 0.01M HEPES pH7.4, 0.15M NaCl, 3 mM EDTA, 0.05% v/v Surfactant P20, 1.0 mg/mL BSA (Octet HBS-ET buffer) with the plate shaking at a speed of 1000 rpm. To assess whether two antibodies were able to compete with one another for binding to their respective epitopes on human C1q, anti-IsdB× anti-C1q bispecific antibodies (denoted mAb-1) were first captured onto anti-hFc antibody coated Octet biosensors (Fortebio Inc, #18-5060) by submerging the biosensors into wells containing a 10 μg/mL solution of anti-IsdB×C1q bispecific antibody for 3 minutes. Extra free anti-hFc sites on the mAb-1 captured sensor tips were saturated with H1H isotype control antibody by immersion into wells containing 200 ug/ml blocking antibody solution (denoted blocking mAb) for 4 minutes. The biosensor tips were subsequently dipped into wells containing a co-complexed solution of Human C1q (10 ug/ml) A and an approximate 10-fold molar excess of a second anti-IsdB× anti-C1q bispecific mAb (denoted mAb-2) for 10 minutes.

All biosensor tips were washed in Octet HBS-ET buffer between each step of the experiment. The real-time binding response was monitored during the course of the experiment, and the binding response at the end of every step was recorded. The responses of C1q pre-complexed with mAb-2 binding to captured mAb-1 were corrected for background binding, compared and competitive/non-competitive behavior was determined for all 17 anti-IsdB× anti-C1q bispecific antibodies.

Results and Conclusion

Table 20 shows the relationships of antibodies competing in both directions, independently of the order of binding. Four anti-IsdB× anti-C1q bispecific antibodies (H1H20633D, H1H20635D, H1H20636D, H1H20641D) did not cross-compete with any of the other antibodies examined in this study. Antibody H1H20631 was an effective bispecific antibody in the in vitro and in vivo assays for reducing bacterial burden and increasing survival. Antibody H1H20631 was cross competitive with antibody H1H20638D.

TABLE 20

|    | First mAb (mAb-1) Captured using AHC Octet Biosensors | mAb-2 Antibodies Shown to Compete with mAb-1 |
|----|---|---|
| 1  | H1H20645D | H1H20643D |
|    |           | H1H20645D |
| 2  | H1H20643D | H1H20645D |
|    |           | H1H20646D |
|    |           | H1H20640D |
| 3  | H1H20646D | H1H20645D |
|    |           | H1H20643D |
|    |           | H1H20640D |
| 4  | H1H20640D | H1H20643D |
|    |           | H1H20646D |
| 5  | H1H20634D | H1H20647D |
|    |           | H1H20644D |
|    |           | H1H20639D |
|    |           | H1H20637D |
|    |           | H1H20632D |
| 6  | H1H20647D | H1H20634D |
|    |           | H1H20644D |
|    |           | H1H20639D |
|    |           | H1H20637D |
|    |           | H1H20642D |
| 7  | H1H20644D | H1H20634D |
|    |           | H1H20647D |
|    |           | H1H20639D |
|    |           | H1H20637D |
|    |           | H1H20642D |
| 8  | H1H20639D | H1H20634D |
|    |           | H1H20647D |
|    |           | H1H20644D |
|    |           | H1H20637D |
|    |           | H1H20642D |
| 9  | H1H20637D | H1H20634D |
|    |           | H1H20647D |
|    |           | H1H20644D |
|    |           | H1H20639D |
| 10 | H1H20642D | H1H20647D |
|    |           | H1H20644D |
|    |           | H1H20639D |
|    |           | H1H20632D |
| 11 | H1H20632D | H1H20634D |
|    |           | H1H20642D |
|    |           | H1H20638D |
| 12 | H1H20638D | H1H20632D |
|    |           | H1H20631D |
| 13 | H1H20631D | H1H20638D |

Example 12. Determining the Biological Activity of Anti-IsdB× Anti-C1q Antibodies in a Mouse Model of S. aureus MRSA Bacteremia In order to study the *S. aureus* infection dynamics and effect of potential therapeutics, a bacteremia model with methicillin resistant *S. aureus* (MRSA) strains was developed. Two different MRSA strains were used in these experiments, a USA400 MRSA strain, MW2 (ATCC, Cat. No. BAA-1707, lot number 58910673) was used, as well as a USA300 MRSA strain, CA127 (NARSA, Cat. No. NRS643). An *S. aureus* Newman strain (a methicillin sensitive clinical isolate, (MSSA)) was also used in these studies. This model was used to evaluate the activity of anti-IsdB× anti-C1q bispecific antibodies against *S. aureus* in reducing bacterial burden.

Experimental Procedure:

Humanized C1q ($C1q^{Hu/Hu}$) mice were infected intraperitoneally with either $1.5 \times 10^8$ colony forming units (CFUs) per mouse of *S. aureus* Newman strain in a volume of 200 ul, $1.4 \times 10^8$ CFUs per mouse of a MRSA strain designated MW2 in a volume of 200 ul, or $1.4 \times 10^8$ CFUs per mouse of another MRSA strain designated CA127 in a volume of 200 ul. All three *S. aureus* strains were grown to log phase, $OD600 \leq 1$, in Tryptic Soy Broth (TSB) at 37° C. and washed 3 times in phosphate buffered saline (PBS) and adjusted to the desired density for infection. Twenty-four (24) hours following infection (Day 1), mice were dosed intraperitoneally with 100 ug of the anti-IsdB× anti-C1q bispecific antibody designated H1H20631D (See Table 6 for amino acid sequence identifiers), or 100 ug of Control II antibody designated H1H20295P2, or PBS in a volume of 100 ul. As noted previously herein, Control II is a bivalent antibody specific for IsdB prepared as described in Example 2, Table 3 and comprises the HCVR/LCVR amino acid sequences of SEQ ID NOs:138/146. Mice were weighed daily until Day 4 post infection and change in weight was recorded. Mice were euthanized on Day 4 and kidneys were collected to determine bacterial organ burden. Briefly, kidneys were homogenized in 5 mL PBS using gentleMACS Octo Dissociator (Miltenyi Biotec) using programme-E and the homogenate was then diluted in PBS and multiple 10-fold serial dilutions were plated on LB agar plates and incubated at 37° C. overnight. The next day, individual colonies were counted to determine bacterial burden and results were reported as CFUs/gram tissue.

Results Summary and Conclusions:

The bispecific anti-IsdB× anti-C1q antibody, designated H1H20631D, was tested alongside a control antibody for efficacy in improving kidney burden in a humanized C1q mouse strain (n=5). Compared to the mice treated with the isotype control antibody (Control II, described above), where 7 logs of *S. aureus* MRSA (MW2 and CA127) CFUs were recovered from the kidneys on Day 4, a 2-4 log reduction was observed in overall CFUs after treatment with the IsdB×C1q bispecific antibody, H1H20631D.

Taken together, the anti-IsdB× anti-C1q bispecific antibody is efficacious at reducing kidney bacterial burden in a humanized C1q mouse strain with *S. aureus* MSSA and MRSA bacteremia.

Tabulated Data Summary:

Table 21 below shows the *S. aureus* burden in kidneys 3 days after treatment with 5 mg/kg anti-IsdB× anti-C1q bispecific and control antibody.

TABLE 21

| AbPID Treatment (100 ug/mouse) | Bacterial strain | CFUs/g kidney | SD | Mice (n) | Mice surviving at time of treatment on Day 1 (n) |
|---|---|---|---|---|---|
| None | Newman | 4.86E+07 | 4.96E+08 | 5 | 5 |
| Control II | Newman | 3.54E+07 | 1.09E+09 | 5 | 5 |
| H1H20631D | Newman | 5.54E+05 | 8.34E+05 | 5 | 5 |
| Control II | MW2 | 2.04E+07 | 1.55E+07 | 5 | 3 |
| H1H20631D | MW2 | 1.09E+05 | 3.92E+04 | 5 | 2 |
| Control II | CA127 | 2.34E+07 | 6.34E+06 | 5 | 3 |
| H1H20631D | CA127 | 1.33E+03 | 2.91E+03 | 3 | 4 |

Example 13. Determining Biological Activity of an Anti-IsdBx Anti-C1q Antibody in Combination with a Standard-of-Care Antibiotic in a Mouse Model of S. aureus MRSA Bacteremia The bacteremia model described above in Example 12 was used to evaluate the activity of an anti-IsdBx anti-C1q bispecific antibody against S. aureus MRSA strains in reducing bacterial burden when used in combination with a standard-of-care antibiotic.

Experimental Procedure:

Humanized C1q ($C1q^{Hu/Hu}$) mice were infected intraperitoneally with $1.3 \times 10^8$ colony forming units (CFUs) per mouse of S. aureus MW2 in a volume of 200 ul. S. aureus MW2 was grown to log phase, $OD_{600} \leq 1$, in TSB at 37° C. and washed 3 times in PBS and adjusted to the desired density for infection. Starting at eighteen (18) hours following infection, 2 groups of mice (n=5) were treated with 80 mg/kg of linezolid by oral gavage (200 ul volume), twice daily on Days 1, 2 and 3. Twenty-four (24) hours post infection, mice were administered with a single 100 ug dose of the anti-IsdBx anti-C1q bispecific antibody designated H1H20631D (See Table 6), or PBS in a volume of 100 ul, intraperitoneally. Mice were weighed daily until Day 4 post infection and change in weight was recorded. Mice were euthanized on Day 4 and kidneys, lungs and hearts were collected to determine organ burden. Briefly, the organs were homogenized in 5 mL PBS using gentleMACS Octo Dissociator (Miltenyi Biotec) using programme-E. The tissue homogenates were then diluted in PBS and multiple 10-fold serial dilutions were plated on LB agar plates and incubated at 37° C. overnight. The next day, individual colonies were counted to determine bacterial burden and results were reported as CFUs/gram tissue.

Results Summary and Conclusions:

Bispecific anti-IsdBx anti-C1q antibody, H1H20631D, was tested alongside a standard-of-care antibiotic, linezolid, for efficacy in reducing the bacterial burden in the kidney, lung, and heart of humanized C1q mice. Compared to the infection control mice (mice given no antibiotic or antibody) where 8.5 logs of S. aureus CFUs were recovered from the kidneys on Day 4, a 2.5 log reduction in overall CFUs after treatment with H1H20631D compared to slightly less than 2 log reduction in CFUs with linezolid treatment was observed. In mice treated with the combination of H1H20631D and linezolid, a 3.5 log reduction of S. aureus CFUs was observed. In the lung, treatment with either single agent, H1H20631D or linezolid, resulted in a 2 log reduction in overall CFUs. In mice treated with the combination of H1H20631D and linezolid, a reduction of 4 logs of S. aureus CFUs in the lungs was observed. Similarly, in the heart, treatment with H1H20631D resulted in a 4 log CFU reduction and linezolid resulted in a 3 log CFU reduction. In mice treated with the combination of H1H20631D and linezolid, we were unable to culture any bacteria from the heart (data in the table is the limit of detection in the assay of $10^3$ CFU).

Taken together, the anti-IsdBx anti-C1q bispecific antibody can have additive efficacy with linezolid in reducing organ bacterial burden in a humanized C1q mouse strain with S. aureus MRSA bacteremia.

Tabulated Data Summary:

Table 22 below shows the S. aureus burden in kidneys 3 days after treatment with linezolid and 5 mg/kg anti-IsdBx anti-C1q bispecific.

TABLE 22

| AbPID Treatment (100 ug/mouse) | Antibiotic | CFUs/g kidney | SD | Mice (n) |
|---|---|---|---|---|
| None | None | 5.80E+08 | 1.22E+08 | 3 |
| H1H20631D | None | 1.56E+06 | 1.56E+05 | 3 |
| H1H20631D | Linezolid | 1.65E+05 | 3.60E+05 | 4 |
| None | Linezolid | 6.99E+06 | 2.14E+07 | 4 |

Table 23 below shows the S. aureus burden in lung 3 days after treatment with linezolid and 5 mg/kg anti-IsdBx anti-C1q bispecific.

TABLE 23

| AbPID Treatment (100 ug/mouse) | Antibiotic | CFUs/g lung | SD | Mice (n) |
|---|---|---|---|---|
| None | None | 5.18E+07 | 7.43E+07 | 3 |
| H1H20631D | None | 4.36E+05 | 1.04E+05 | 3 |
| H1H20631D | Linezolid | 3.13E+03 | 1.47E+04 | 4 |
| None | Linezolid | 6.98E+05 | 3.81E+05 | 4 |

Table 24 below shows the S. aureus burden in heart 3 days after treatment with linezolid and 5 mg/kg anti-IsdBx anti-C1q bispecific.

TABLE 24

| AbPID Treatment (100 ug/mouse) | Antibiotic | CFUs/g heart | SD | Mice (n) |
|---|---|---|---|---|
| None | None | 2.63E+08 | 3.99E+08 | 3 |
| H1H20631D | None | 2.04E+04 | 2.43E+05 | 3 |
| H1H20631D | Linezolid | 1.00E+03 | 2.54E+04 | 4 |
| None | Linezolid | 2.08E+05 | 2.11E+05 | 4 |

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

What is claimed is:

1. An isolated bispecific antigen binding molecule comprising:

a) a first antigen-binding domain that binds *Staphylococcus aureus* IsdB antigen, wherein the first antigen-binding domain comprises three heavy chain complementarity determining regions (HCDRs) contained within a heavy chain variable region (HCVR) comprising the amino acid sequence of SEQ ID NO: 138 and three light chain complementarity determining regions (LCDRs) contained within a light chain variable region (LCVR) comprising the amino acid sequence of SEQ ID NO: 146; and b) a second antigen-binding domain that binds a complement component C1q, wherein the second antigen-binding domain comprises three HCDRs contained within a HCVR comprising the amino acid sequence of SEQ ID NO: 2 and three LCDRs contained within a LCVR comprising the amino acid sequence of SEQ ID NO: 146.

2. The isolated bispecific antigen binding molecule of claim 1, wherein the bispecific antigen binding molecule binds to the *Staphylococcus aureus* IsdB antigen with an $EC_{50}$ of about 10 nM or less.

3. The isolated bispecific antigen binding molecule of claim 1, wherein the bispecific antigen binding molecule promotes human C1q deposition on *Staphylococcus aureus* with an $EC_{50}$ of about 10 nM or less.

4. The isolated bispecific antigen binding molecule of claim 1, wherein the first antigen-binding domain binds to a *Staphylococcus aureus* IsdB protein comprising an amino acid sequence of amino acids 3 to 574 if SEQ ID NO: 169.

5. The isolated bispecific antigen binding molecule of claim 1, wherein the complement component C1q is a human C1q.

6. The isolated bispecific antigen binding molecule of claim 1, wherein the first antigen binding domain binds to *Staphylococcus aureus* IsdB with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

7. The isolated bispecific antigen binding molecule of claim 1, wherein the second antigen binding domain binds to complement component C1q with a $K_D$ of less than about 25 nM, less than about 20 nM, less than about 15 nM, less than about 10 nM, less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

8. The isolated bispecific antigen binding molecule of claim 1, wherein the first antigen-binding domain comprises:
   a) a heavy chain CDR1 (HCDR1) comprising the amino acid sequence of SEQ ID NO:140, a heavy chain CDR2 (HCDR2) comprising the amino acid sequence of SEQ ID NO:142, and a heavy chain CDR3 (HCDR3) comprising the amino acid sequence of SEQ ID NO:144; and a light chain CDR1 (LCDR1) comprising the amino acid sequence of SEQ ID NO:148, a light chain CDR2 (LCDR2) comprising the amino acid sequence of SEQ ID NO:150, and a light chain CDR3 (LCDR3) comprising the amino acid sequence of SEQ ID NO:152.

9. The isolated bispecific antigen binding molecule of claim 1, wherein the first antigen binding domain comprises an HCVR/LCVR pair comprising the amino acid sequences of SEQ ID NOs: 138/146.

10. The isolated bispecific antigen binding molecule of claim 1, wherein the bispecific antigen binding molecule blocks the binding of the human C1q to human IgG1-k with an $IC_{50}$ of about 10 nM or less.

11. The isolated bispecific antigen binding molecule of claim 10, wherein the bispecific antigen binding molecule blocks the binding of the human C1q to human IgM with an $IC_{50}$ of about 50 nM or less.

12. The isolated bispecific antigen binding molecule of claim 1, wherein the second antigen-binding domain comprises:
   b) an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8; and an LCDR1 comprising the amino acid sequence of SEQ ID NO: 148, an LCDR2 comprising the amino acid sequence of SEQ ID NO: 150, and an LCDR3 comprising the amino acid sequence of SEQ ID NO: 152.

13. The isolated bispecific antigen binding molecule of claim 1, wherein the second antigen binding domain comprises an HCVR/LCVR pair comprising the amino acid sequences of SEQ ID NOs: 2/146.

14. The isolated bispecific antigen binding molecule of claim 1, comprising:
   a) a first antigen-binding domain that comprises an HCDR1 comprising the amino acid sequence of SEQ ID NO:140, an HCDR2 comprising the amino acid sequence of SEQ ID NO:142, an HCDR3 comprising the amino acid sequence of SEQ ID NO:144, an LCDR1 comprising the amino acid sequence of SEQ ID NO:148, an LCDR2 comprising the amino acid sequence of SEQ ID NO:150, and an LCDR3 comprising the amino acid sequence of SEQ ID NO:152; and
   b) a second antigen binding domain that comprises an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:148, an LCDR2 comprising the amino acid sequence of SEQ ID NO:150, and an LCDR3 comprising the amino acid sequence of SEQ ID NO:152.

15. The isolated bispecific antigen binding molecule of claim 1, wherein
   a) the first antigen binding domain comprises an HCVR comprising the amino acid sequence of SEQ ID NO:138 and an LCVR comprising the amino acid sequence of SEQ ID NO:146; and
   b) the second antigen binding domain comprises an HCVR comprising the amino acid sequence of SEQ ID NO:2 and an LCVR comprising the amino acid sequence of SEQ ID NO:146.

16. A pharmaceutical composition comprising the bispecific antigen-binding molecule of claim 1, and a pharmaceutically acceptable carrier or diluent.

* * * * *

SEQUENCE LISTING

<160> NUMBER OF SEQ ID NOS: 175

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1

```
gaagtgcagc tggtggagtc tgggggaggc gtggtacagc ctgggggtc cctgagactc      60
tcctgtgcag cctctggatt cagccttgat gattatgcca tgcactgggt ccgtcaaact    120
ccagggaagg gtctggagtg ggtctctctt attagtgggg atggtagtcg cacatcctat    180
gcagactctg tgaagggccg attcaccatc tccagagaca cagcaaaaa ctccctgtat    240
ctgaaaatga acagtctgag aactgaggac accgccttgt attactgtac aaaagatccc    300
cataactcca actggttcga cccctggggc cagggaaccc tggtcaccgt ctcctca       357
```

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Leu Asp Asp Tyr
            20                  25                  30

Ala Met His Trp Val Arg Gln Thr Pro Gly Lys Gly Leu Glu Trp Val
        35                  40                  45

Ser Leu Ile Ser Gly Asp Gly Ser Arg Thr Ser Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Lys Met Asn Ser Leu Arg Thr Glu Asp Thr Ala Leu Tyr Tyr Cys
                85                  90                  95

Thr Lys Asp Pro His Asn Ser Asn Trp Phe Asp Pro Trp Gly Gln Gly
            100                 105                 110

Thr Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcagcc ttgatgatta tgcc                                            24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Ser Leu Asp Asp Tyr Ala
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagtgggg atggtagtcg caca                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Gly Asp Gly Ser Arg Thr
1               5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
acaaaagatc cccataactc caactggttc gacccc                             36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Thr Lys Asp Pro His Asn Ser Asn Trp Phe Asp Pro
1               5                   10

<210> SEQ ID NO 9
<211> LENGTH: 363
<212> TYPE: DNA
<213> ORGANISM: Artificial Sequence
<220> FEATURE:
<223> OTHER INFORMATION: synthetic

<400> SEQUENCE: 9
caggtgcagc tggtggagtc tgggggaggc gtggtccagc ctggggagtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaaaactat   180
gcagactccg tgaagggccg attcaccatc tccagadaca gttccaagaa cacgctgtat   240
ctgcaaatga acagcctgag agccgaggac acggctgtgt attactgtgc gagagagaat   300
agcgagggct attattacgg tatggacgtc tggggccaag ggaccacggt caccgtctcc   360
tca                                                                363

```
<210> SEQ ID NO 10
<211> LENGTH: 121
<212> TYPE: PRT
<213> ORGANISM: Artificial Sequence
<220> FEATURE:
<223> OTHER INFORMATION: synthetic

<400> SEQUENCE: 10
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Ser Glu Gly Tyr Tyr Tyr Gly Met Asp Val Trp Gly
            100                 105                 110

Gln Gly Thr Thr Val Thr Val Ser Ser
        115                 120

```
<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
```
ggattcacct tcagtagcta tggc                                              24

```
<210> SEQ ID NO 12
<211> LENGTH: 8
<212> TYPE: PRT
<213> ORGANISM: Artificial Sequence
<220> FEATURE:
<223> OTHER INFORMATION: synthetic

<400> SEQUENCE: 12
```

Gly Phe Thr Phe Ser Ser Tyr Gly
1               5

```
<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
```
atatggtatg atggaagtaa taaa                                              24

```
<210> SEQ ID NO 14
<211> LENGTH: 8
<212> TYPE: PRT
<213> ORGANISM: Artificial Sequence
<220> FEATURE:
<223> OTHER INFORMATION: synthetic

<400> SEQUENCE: 14
```

Ile Trp Tyr Asp Gly Ser Asn Lys
1               5

<210> SEQ ID NO 15
<211> LENGTH: 42
<212> TYPE: DNA
<213> ORGANISM: Artificial Sequence
<220> FEATURE:
<223> OTHER INFORMATION: synthetic

<400> SEQUENCE: 15
gcgagagaga atagcgaggg ctattattac ggtatggacg tc         42

<210> SEQ ID NO 16
<211> LENGTH: 14
<212> TYPE: PRT
<213> ORGANISM: Artificial Sequence
<220> FEATURE:
<223> OTHER INFORMATION: synthetic

<400> SEQUENCE: 16

Ala Arg Glu Asn Ser Glu Gly Tyr Tyr Tyr Gly Met Asp Val
1               5                   10

<210> SEQ ID NO 17
<211> LENGTH: 354
<212> TYPE: DNA
<213> ORGANISM: Artificial Sequence
<220> FEATURE:
<223> OTHER INFORMATION: synthetic

<400> SEQUENCE: 17
caggtgcagc tggtggagtc tgggggaggc gtggtccagc ctgggaggtc cctgagactc         60
tcctgtgcag cgtctggatt caccttcagt agctacggca tgcactgggt ccgccaggct        120
ccaggcaagg gactggaatg ggtgacgaat atatggtatg atggaaataa taaatactat        180
acagactccg tgaagggccg attcaccatc tccagagaca attccaagaa tacactgtat        240
ttgcaaatga acagcctgac agccgaagac acggctgtgt attactgtgc gagagatgga        300
gactattacg ttatggacgt ctggggccaa gggaccacgg tcaccgtctc ctca              354

<210> SEQ ID NO 18
<211> LENGTH: 118
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Asn Ile Trp Tyr Asp Gly Asn Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Arg Asp Gly Asp Tyr Tyr Val Met Asp Val Trp Gly Gln Gly Thr
            100                 105                 110

Thr Val Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtagcta cggc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atatggtatg atggaaataa taaa                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Trp Tyr Asp Gly Asn Asn Lys
1               5

<210> SEQ ID NO 23
<211> LENGTH: 33
<212> TYPE: DNA
<213> ORGANISM: Artificial Sequence
<220> FEATURE:
<223> OTHER INFORMATION: synthetic

<400> SEQUENCE: 23
gcgagagatg gagactatta cgttatggac gtc                                33

<210> SEQ ID NO 24
<211> LENGTH: 11
<212> TYPE: PRT
<213> ORGANISM: Artificial Sequence
<220> FEATURE:
<223> OTHER INFORMATION: synthetic

<400> SEQUENCE: 24

Ala Arg Asp Gly Asp Tyr Tyr Val Met Asp Val

<210> SEQ ID NO 25
<211> LENGTH: 351
<212> TYPE: DNA
<213> ORGANISM: Artificial Sequence
<220> FEATURE:
<223> OTHER INFORMATION: synthetic

<400> SEQUENCE: 25

```
gaggtgcagc tggtgcagtc tggaccagag gtgaaaaagc ccggggagtc tctgaagatc      60
tcctgtaagg gttctggata caactttctc ggttactgga tcggctgggt gcgccagatg     120
cccgagaaag gcctggaatg gatggcgttc atctatcccg gtgactctga tttcagatac     180
agtccgtcct tccaaggcca ggtcaccatc tcagtcgaca ggtccgtcac cactgcctac     240
ctccattgga gcagcctgaa ggcctcggac accggcatat ttttgtgt gagacagact       300
ggcaacggta tggacgtctg gggccaaggg accacggtca ccgtctcctc a              351
```

<210> SEQ ID NO 26
<211> LENGTH: 117
<212> TYPE: PRT
<213> ORGANISM: Artificial Sequence
<220> FEATURE:
<223> OTHER INFORMATION: synthetic

<400> SEQUENCE: 26

Glu Val Gln Leu Val Gln Ser Gly Pro Glu Val Lys Lys Pro Gly Glu
1               5                   10                  15

Ser Leu Lys Ile Ser Cys Lys Gly Ser Gly Tyr Asn Phe Leu Gly Tyr
            20                  25                  30

Trp Ile Gly Trp Val Arg Gln Met Pro Glu Lys Gly Leu Glu Trp Met
        35                  40                  45

Ala Phe Ile Tyr Pro Gly Asp Ser Asp Phe Arg Tyr Ser Pro Ser Phe
    50                  55                  60

Gln Gly Gln Val Thr Ile Ser Val Asp Arg Ser Val Thr Thr Ala Tyr
65                  70                  75                  80

Leu His Trp Ser Ser Leu Lys Ala Ser Asp Thr Gly Ile Tyr Phe Cys
                85                  90                  95

Val Arg Gln Thr Gly Asn Gly Met Asp Val Trp Gly Gln Gly Thr Thr
            100                 105                 110

Val Thr Val Ser Ser
        115

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27

```
ggatacaact ttctcggtta ctgg                                              24
```

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

```
Gly Tyr Asn Phe Leu Gly Tyr Trp
1               5
```

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
atctatcccg gtgactctga tttc                                              24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

```
Ile Tyr Pro Gly Asp Ser Asp Phe
1               5
```

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31
gtgagacaga ctggcaacgg tatggacgtc                                        30

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

```
Val Arg Gln Thr Gly Asn Gly Met Asp Val
1               5                   10
```

<210> SEQ ID NO 33
<211> LENGTH: 375
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctggagggtc cctgagactc        60
tcctgtgcag cgtctggatt caccttcagt aactatggca tgcattgggt ccgccaggct       120
ccaggcaagg ggctggagtg gttggcagtt atatactatg atggaattaa gagatactat       180
ggggactccg tgcagggccg attcattatc tccagagaca attccaagaa cacgctttat       240
ctgcaaatga acagcctatg agacgaagac acggctgtgt attactgtgc gcgggcattt       300
tcagcggctg gcccgtacaa ctactactac gctatggacg tctggggcca agggaccacg       360
gtcaccgtct cctca                                                        375

```
<210> SEQ ID NO 34
<211> LENGTH: 125
<212> TYPE: PRT
<213> ORGANISM: Artificial Sequence
<220> FEATURE:
<223> OTHER INFORMATION: synthetic

<400> SEQUENCE: 34
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Leu
        35                  40                  45

Ala Val Ile Tyr Tyr Asp Gly Ile Lys Arg Tyr Tyr Gly Asp Ser Val
    50                  55                  60

Gln Gly Arg Phe Ile Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Ala Phe Ser Ala Ala Gly Pro Tyr Asn Tyr Tyr Ala Met
            100                 105                 110

Asp Val Trp Gly Gln Gly Thr Thr Val Thr Val Ser Ser
        115                 120                 125

```
<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct tcagtaacta tggc                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36
```

Gly Phe Thr Phe Ser Asn Tyr Gly
1               5

```
<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatactatg atggaattaa gaga                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38
```

Ile Tyr Tyr Asp Gly Ile Lys Arg
1               5

<210> SEQ ID NO 39
<211> LENGTH: 54
<212> TYPE: DNA
<213> ORGANISM: Artificial Sequence
<220> FEATURE:
<223> OTHER INFORMATION: synthetic

<400> SEQUENCE: 39
gcgcgggcat tttcagcggc tggcccgtac aactactact acgctatgga cgtc        54

<210> SEQ ID NO 40
<211> LENGTH: 18
<212> TYPE: PRT
<213> ORGANISM: Artificial Sequence
<220> FEATURE:
<223> OTHER INFORMATION: synthetic

<400> SEQUENCE: 40

Ala Arg Ala Phe Ser Ala Ala Gly Pro Tyr Asn Tyr Tyr Tyr Ala Met
1               5                   10                  15

Asp Val

<210> SEQ ID NO 41
<211> LENGTH: 375
<212> TYPE: DNA
<213> ORGANISM: Artificial Sequence
<220> FEATURE:
<223> OTHER INFORMATION: synthetic

<400> SEQUENCE: 41
gaggtgcagc tggtggagtc tgggggaggc ttggtacagc ctggagggtc cctgagactc     60
tcctgtgcag cctctggatt caccttcagt aattatgaga tgaactgggt ccgccaggct    120
ccagggaagg ggctggattg ggtttcatac attagtacta gtggtagtgt catatactac    180
gcagactctg tgaagggccg attcaccatc tccagagaca cgccaagaa ctcactgtat     240 ctggaaatga acagcctgag agccgaggac acggctgttt attactgtgc gagggttac     300 gattttttgga gtggttccga ctactactac ggtatggacg tctggggcca agggaccacg    360
gtcaccgtct cctca                                                     375

<210> SEQ ID NO 42
<211> LENGTH: 125
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Glu Met Asn Trp Val Arg Gln Ala Pro Gly Lys Gly Leu Asp Trp Val
            35                  40                  45

Ser Tyr Ile Ser Thr Ser Gly Ser Val Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Val Tyr Tyr Cys
            85                  90                  95

Ala Arg Gly Tyr Asp Phe Trp Ser Gly Ser Asp Tyr Tyr Tyr Gly Met
            100                 105                 110

Asp Val Trp Gly Gln Gly Thr Thr Val Thr Val Ser Ser
        115                 120                 125

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
ggattcacct tcagtaatta tgag                                    24

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Ser Asn Tyr Glu
1               5

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
attagtacta gtggtagtgt cata                                    24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Thr Ser Gly Ser Val Ile
1               5

<210> SEQ ID NO 47
<211> LENGTH: 54
<212> TYPE: DNA
<213> ORGANISM: Artificial Sequence
<220> FEATURE:
<223> OTHER INFORMATION: synthetic

<400> SEQUENCE: 47 gcgagggtt acgattttg gagtggttcc gactactact acggtatgga cgtc      54

<210> SEQ ID NO 48
<211> LENGTH: 18
<212> TYPE: PRT
<213> ORGANISM: Artificial Sequence
<220> FEATURE:
<223> OTHER INFORMATION: synthetic

<400> SEQUENCE: 48

Ala Arg Gly Tyr Asp Phe Trp Ser Gly Ser Asp Tyr Tyr Gly Met
1               5                   10                  15

Asp Val

<210> SEQ ID NO 49
<211> LENGTH: 351
<212> TYPE: DNA
<213> ORGANISM: Artificial Sequence
<220> FEATURE:
<223> OTHER INFORMATION: synthetic

<400> SEQUENCE: 49
gaggtgcagc tggtgcagtc tggagcagag gtgaaaaagc ccggggactc tctgaagatc      60
tcctgtaagg gttctggata cagctttacc acctactgga tcggctgggt gcgccagatg     120
cccgggaaag gcctggagtg gatggggatc atctttcctg gtgactctga taccagatac     180
agcccgtcct ccaaggcca ggtcaccatc tcagccgaca gtccatcaa caccgcctac       240 ctacagtgga gcagcctgaa ggcctcggac accgccatat attactgtgc gagacataac     300
cgatgggtgg ccgactactg gggccaggga accctggtca ccgtctcctc a              351

<210> SEQ ID NO 50
<211> LENGTH: 117
<212> TYPE: PRT
<213> ORGANISM: Artificial Sequence
<220> FEATURE:
<223> OTHER INFORMATION: synthetic

<400> SEQUENCE: 50

Glu Val Gln Leu Val Gln Ser Gly Ala Glu Val Lys Lys Pro Gly Asp
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Phe Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Arg His Asn Arg Trp Val Ala Asp Tyr Trp Gly Gln Gly Thr Leu
            100                 105                 110

Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggatacagct ttaccaccta ctgg                                             24

<210> SEQ ID NO 52
<211> LENGTH: 8

```
<212> TYPE: PRT
<213> ORGANISM: Artificial Sequence
<220> FEATURE:
<223> OTHER INFORMATION: synthetic

<400> SEQUENCE: 52

Gly Tyr Ser Phe Thr Thr Tyr Trp
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atctttcctg gtgactctga tacc                                         24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Phe Pro Gly Asp Ser Asp Thr
1               5

<210> SEQ ID NO 55
<211> LENGTH: 30
<212> TYPE: DNA
<213> ORGANISM: Artificial Sequence
<220> FEATURE:
<223> OTHER INFORMATION: synthetic

<400> SEQUENCE: 55
gcgagacata accgatgggt ggccgactac                                   30

<210> SEQ ID NO 56
<211> LENGTH: 10
<212> TYPE: PRT
<213> ORGANISM: Artificial Sequence
<220> FEATURE:
<223> OTHER INFORMATION: synthetic

<400> SEQUENCE: 56

Ala Arg His Asn Arg Trp Val Ala Asp Tyr
1               5                   10

<210> SEQ ID NO 57
<211> LENGTH: 348
<212> TYPE: DNA
<213> ORGANISM: Artificial Sequence
<220> FEATURE:
<223> OTHER INFORMATION: synthetic

<400> SEQUENCE: 57
caggtgcagc tggtggagtc tgggggaggc gtggtccagc ctgggaggtc cctgagactc   60
tcctgtgcaa cgtctggatt caccttcagt agctatggca tgcactgggt ccgccaggct  120
ccaggcaagg gactggagtg gtggcactg atatggtatg atagaaataa tgaatattat   180
gcagactccg tgaagggccg attcaccatc tccagagaca attccaagaa cacgctgtat  240
ctgcaaatga acagcctgag agccgaggac acggctgtgt attactgtgc gagaggggag  300
```
tgggagatgg actactgggg ccagggaacc ctggtcaccg tctcctca       348

<210> SEQ ID NO 58
<211> LENGTH: 116
<212> TYPE: PRT
<213> ORGANISM: Artificial Sequence
<220> FEATURE:
<223> OTHER INFORMATION: synthetic

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Arg Asn Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Trp Glu Met Asp Tyr Trp Gly Gln Gly Thr Leu Val
            100                 105                 110

Thr Val Ser Ser
        115

<210> SEQ ID NO 59
<211> LENGTH: 24
<212> TYPE: DNA
<213> ORGANISM: Artificial Sequence
<220> FEATURE:
<223> OTHER INFORMATION: synthetic

<400> SEQUENCE: 59
ggattcacct tcagtagcta tggc                                  24

<210> SEQ ID NO 60
<211> LENGTH: 8
<212> TYPE: PRT
<213> ORGANISM: Artificial Sequence
<220> FEATURE:
<223> OTHER INFORMATION: synthetic

<400> SEQUENCE: 60

Gly Phe Thr Phe Ser Ser Tyr Gly
1               5

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
atatggtatg atagaaataa tgaa                                  24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

Ile Trp Tyr Asp Arg Asn Asn Glu
1               5

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
gcgagagggg agtgggagat ggactac                                         27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Ala Arg Gly Glu Trp Glu Met Asp Tyr
1               5

<210> SEQ ID NO 65
<211> LENGTH: 327
<212> TYPE: DNA
<213> ORGANISM: Artificial Sequence
<220> FEATURE:
<223> OTHER INFORMATION: synthetic

<400> SEQUENCE: 65
gaaattgtgt tgacacagtc tccaggcacc ctgtctttgt ctccagggga aagagccacc     60
ctctcctgca gggccagtca gaatgttcgc agcggctatt tagcctggta ccagcagaaa    120
cctggccagg ctcccaggct cctcatctat ggtacatcca ccagggtcac tggcatccca    180
gacaggttca gtggctttgg gtctgggaca gacttcactc tcaccatcag cagactggag    240
cctgaagatt ttgcagtgta ttactgtcag cagtatggta attcacctct tttcactttc    300
ggcggaggga ccaaggtgga gatcaaa                                        327

<210> SEQ ID NO 66
<211> LENGTH: 109
<212> TYPE: PRT
<213> ORGANISM: Artificial Sequence
<220> FEATURE:
<223> OTHER INFORMATION: synthetic

<400> SEQUENCE: 66

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Arg Ser Gly
                20                  25                  30

Tyr Leu Ala Trp Tyr Gln Gln Lys Pro Gly Gln Ala Pro Arg Leu Leu
            35                  40                  45

Ile Tyr Gly Thr Ser Thr Arg Val Thr Gly Ile Pro Asp Arg Phe Ser
        50                  55                  60

Gly Phe Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Asn Ser Pro
                85                  90                  95

Leu Phe Thr Phe Gly Gly Gly Thr Lys Val Glu Ile Lys
            100                 105
```

<210> SEQ ID NO 67
<211> LENGTH: 21
<212> TYPE: DNA
<213> ORGANISM: Artificial Sequence
<220> FEATURE:
<223> OTHER INFORMATION: synthetic

<400> SEQUENCE: 67
cagaatgttc gcagcggcta t                                           21

<210> SEQ ID NO 68
<211> LENGTH: 7
<212> TYPE: PRT
<213> ORGANISM: Artificial Sequence
<220> FEATURE:
<223> OTHER INFORMATION: synthetic

<400> SEQUENCE: 68

```
Gln Asn Val Arg Ser Gly Tyr
1               5
```

<210> SEQ ID NO 69
<211> LENGTH: 9
<212> TYPE: DNA
<213> ORGANISM: Artificial Sequence
<220> FEATURE:
<223> OTHER INFORMATION: synthetic

<400> SEQUENCE: 69 ggtacatcc                                                          9

<210> SEQ ID NO 70
<211> LENGTH: 3
<212> TYPE: PRT
<213> ORGANISM: Artificial Sequence
<220> FEATURE:
<223> OTHER INFORMATION: synthetic

<400> SEQUENCE: 70

```
Gly Thr Ser
1
```

<210> SEQ ID NO 71
<211> LENGTH: 30
<212> TYPE: DNA
<213> ORGANISM: Artificial Sequence
<220> FEATURE:
<223> OTHER INFORMATION: synthetic

<400> SEQUENCE: 71
cagcagtatg gtaattcacc tcttttcact                                  30

<210> SEQ ID NO 72
<211> LENGTH: 10
<212> TYPE: PRT
<213> ORGANISM: Artificial Sequence
<220> FEATURE:
<223> OTHER INFORMATION: synthetic

<400> SEQUENCE: 72

```
Gln Gln Tyr Gly Asn Ser Pro Leu Phe Thr
1               5                  10
```

<210> SEQ ID NO 73
<211> LENGTH: 333
<212> TYPE: DNA
<213> ORGANISM: Artificial Sequence
<220> FEATURE:
<223> OTHER INFORMATION: synthetic

<400> SEQUENCE: 73

```
gaaatagtga tgacacagtc tccagccacc ctgtctgtgt ctccagggga aagagccacc    60
ctctcctgca cggccagtca gactattaac agcaatttag cctggtacca acagagacct   120
ggccaggctc ccaggctcct catctatggt gcatccacca gggccactgg taccccagcc   180
aggttcagag gcagtgggtc tgggaccgaa ttcactctca ccatcagcag cctgctgtct   240
gaagattttg cagtttatta ctgtcagaat tataataact ggccgccggg gggccccgc   300
actttcggcc ctgggaccaa agtggatatc aaa                                333
```

<210> SEQ ID NO 74
<211> LENGTH: 111
<212> TYPE: PRT
<213> ORGANISM: Artificial Sequence
<220> FEATURE:
<223> OTHER INFORMATION: synthetic

<400> SEQUENCE: 74

```
Glu Ile Val Met Thr Gln Ser Pro Ala Thr Leu Ser Val Ser Pro Gly
1               5                  10                  15

Glu Arg Ala Thr Leu Ser Cys Thr Ala Ser Gln Thr Ile Asn Ser Asn
            20                  25                  30

Leu Ala Trp Tyr Gln Gln Arg Pro Gly Gln Ala Pro Arg Leu Leu Ile
        35                  40                  45

Tyr Gly Ala Ser Thr Arg Ala Thr Gly Thr Pro Ala Arg Phe Arg Gly
    50                  55                  60

Ser Gly Ser Gly Thr Glu Phe Thr Leu Thr Ile Ser Ser Leu Leu Ser
65                  70                  75                  80

Glu Asp Phe Ala Val Tyr Tyr Cys Gln Asn Tyr Asn Asn Trp Pro Pro
                85                  90                  95

Gly Gly Pro Arg Thr Phe Gly Pro Gly Thr Lys Val Asp Ile Lys
            100                 105                 110
```

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75

```
cagactatta acagcaat                                                   18
```

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Thr Ile Asn Ser Asn

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 ggtgcatcc                                                                      9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Gly Ala Ser
1

<210> SEQ ID NO 79
<211> LENGTH: 39
<212> TYPE: DNA
<213> ORGANISM: Artificial Sequence
<220> FEATURE:
<223> OTHER INFORMATION: synthetic

<400> SEQUENCE: 79
cagaattata ataactggcc gccgggggc ccccgcact                                     39

<210> SEQ ID NO 80
<211> LENGTH: 13
<212> TYPE: PRT
<213> ORGANISM: Artificial Sequence
<220> FEATURE:
<223> OTHER INFORMATION: synthetic

<400> SEQUENCE: 80

Gln Asn Tyr Asn Asn Trp Pro Pro Gly Gly Pro Arg Thr
1               5                   10

<210> SEQ ID NO 81
<211> LENGTH: 324
<212> TYPE: DNA
<213> ORGANISM: Artificial Sequence
<220> FEATURE:
<223> OTHER INFORMATION: synthetic

<400> SEQUENCE: 81
gacatccaga tgacccagtc tccatcctcc ctgtctgcat ctataggaga cagagtcacc            60
atcacttgcc ggacgagtca ggacattaac aattatttag cctggtatca gcagaaacca           120
gggaaagttc ctaaactcct gatctttttct gcatccactt tgcaatcagg ggtcccatct          180
cggttcagcg gcagtggatt tgggacagat ttcactttca taatcagcag cctgcagcct           240
gaggatgttg caacttattt ctgtcaaaag tatgacagtg ccgcggcct cagtttcggc            300 ggagggacca aggtggagat caaa                                                  324

<210> SEQ ID NO 82
<211> LENGTH: 108
<212> TYPE: PRT
<213> ORGANISM: Artificial Sequence
<220> FEATURE:
<223> OTHER INFORMATION: synthetic

<400> SEQUENCE: 82

Asp Ile Gln Met Thr Gln Ser Pro Ser Ser Leu Ser Ala Ser Ile Gly
1               5                   10                  15

Asp Arg Val Thr Ile Thr Cys Arg Thr Ser Gln Asp Ile Asn Asn Tyr
            20                  25                  30

Leu Ala Trp Tyr Gln Gln Lys Pro Gly Lys Val Pro Lys Leu Leu Ile
        35                  40                  45

Phe Ser Ala Ser Thr Leu Gln Ser Gly Val Pro Ser Arg Phe Ser Gly
    50                  55                  60

Ser Gly Phe Gly Thr Asp Phe Thr Phe Ile Ile Ser Ser Leu Gln Pro
65                  70                  75                  80

Glu Asp Val Ala Thr Tyr Phe Cys Gln Lys Tyr Asp Ser Gly Arg Gly
                85                  90                  95

Leu Ser Phe Gly Gly Gly Thr Lys Val Glu Ile Lys
            100                 105

<210> SEQ ID NO 83
<211> LENGTH: 18
<212> TYPE: DNA
<213> ORGANISM: Artificial Sequence
<220> FEATURE:
<223> OTHER INFORMATION: synthetic

<400> SEQUENCE: 83
caggacatta acaattat                                              18

<210> SEQ ID NO 84
<211> LENGTH: 6
<212> TYPE: PRT
<213> ORGANISM: Artificial Sequence
<220> FEATURE:
<223> OTHER INFORMATION: synthetic

<400> SEQUENCE: 84

Gln Asp Ile Asn Asn Tyr
1               5

<210> SEQ ID NO 85
<211> LENGTH: 9
<212> TYPE: DNA
<213> ORGANISM: Artificial Sequence
<220> FEATURE:
<223> OTHER INFORMATION: synthetic

<400> SEQUENCE: 85 tctgcatcc                                                         9

<210> SEQ ID NO 86
<211> LENGTH: 3
<212> TYPE: PRT
<213> ORGANISM: Artificial Sequence
<220> FEATURE:
<223> OTHER INFORMATION: synthetic

<400> SEQUENCE: 86

Ser Ala Ser
1

<210> SEQ ID NO 87
<211> LENGTH: 30

```
<212> TYPE: DNA
<213> ORGANISM: Artificial Sequence
<220> FEATURE:
<223> OTHER INFORMATION: synthetic

<400> SEQUENCE: 87
caaaagtatg acagtggccg cggcctcagt                                    30

<210> SEQ ID NO 88
<211> LENGTH: 10
<212> TYPE: PRT
<213> ORGANISM: Artificial Sequence
<220> FEATURE:
<223> OTHER INFORMATION: synthetic

<400> SEQUENCE: 88

Gln Lys Tyr Asp Ser Gly Arg Gly Leu Ser
1               5                   10

<210> SEQ ID NO 89
<211> LENGTH: 351
<212> TYPE: DNA
<213> ORGANISM: Artificial Sequence
<220> FEATURE:
<223> OTHER INFORMATION: synthetic

<400> SEQUENCE: 89
gaggtgcagc tggtgcagtc tggagcagag gtgaaaaagc ccggggagtc tctgaagatc    60
tcctgtaagg cttctggata caattttaat agctattgga tcggctgggt gcgccagatg   120
cccgggaagg gcctggagtg gatgggaatc gtctttcctg gtgactctga taccagatac   180
agtccgtcct tccaaggcca ggtcaccatc tcagccgacg agtccatcaa caccgcctac   240
ctgcagtgga gcagcctgaa ggcctcggac accgccgtgt attactgtgc gaggcacaca   300
aggtggtacc ttgactactg gggccaggga accctggtca ccgtctcctc a            351

<210> SEQ ID NO 90
<211> LENGTH: 117
<212> TYPE: PRT
<213> ORGANISM: Artificial Sequence
<220> FEATURE:
<223> OTHER INFORMATION: synthetic

<400> SEQUENCE: 90

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Asn Phe Asn Ser Tyr
                20                  25                  30

Trp Ile Gly Trp Val Arg Gln Met Pro Gly Lys Gly Leu Glu Trp Met
            35                  40                  45

Gly Ile Val Phe Pro Gly Asp Ser Asp Thr Arg Tyr Ser Pro Ser Phe
        50                  55                  60

Gln Gly Gln Val Thr Ile Ser Ala Asp Glu Ser Ile Asn Thr Ala Tyr
65                  70                  75                  80

Leu Gln Trp Ser Ser Leu Lys Ala Ser Asp Thr Ala Val Tyr Tyr Cys
                85                  90                  95

Ala Arg His Thr Arg Trp Tyr Leu Asp Tyr Trp Gly Gln Gly Thr Leu
            100                 105                 110

Val Thr Val Ser Ser
        115
```

```
<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
ggatacaatt ttaatagcta ttgg                                              24

<210> SEQ ID NO 92
<211> LENGTH: 8
<212> TYPE: PRT
<213> ORGANISM: Artificial Sequence
<220> FEATURE:
<223> OTHER INFORMATION: synthetic

<400> SEQUENCE: 92

Gly Tyr Asn Phe Asn Ser Tyr Trp
1               5

<210> SEQ ID NO 93
<211> LENGTH: 24
<212> TYPE: DNA
<213> ORGANISM: Artificial Sequence
<220> FEATURE:
<223> OTHER INFORMATION: synthetic

<400> SEQUENCE: 93
gtctttcctg gtgactctga tacc                                              24

<210> SEQ ID NO 94
<211> LENGTH: 8
<212> TYPE: PRT
<213> ORGANISM: Artificial Sequence
<220> FEATURE:
<223> OTHER INFORMATION: synthetic

<400> SEQUENCE: 94

Val Phe Pro Gly Asp Ser Asp Thr
1               5

<210> SEQ ID NO 95
<211> LENGTH: 30
<212> TYPE: DNA
<213> ORGANISM: Artificial Sequence
<220> FEATURE:
<223> OTHER INFORMATION: synthetic

<400> SEQUENCE: 95
gcgaggcaca caaggtggta ccttgactac                                        30

<210> SEQ ID NO 96
<211> LENGTH: 10
<212> TYPE: PRT
<213> ORGANISM: Artificial Sequence
<220> FEATURE:
<223> OTHER INFORMATION: synthetic

<400> SEQUENCE: 96

Ala Arg His Thr Arg Trp Tyr Leu Asp Tyr
1               5                   10

<210> SEQ ID NO 97
<211> LENGTH: 354
<212> TYPE: DNA
<213> ORGANISM: Artificial Sequence
```

<220> FEATURE:
<223> OTHER INFORMATION: synthetic

<400> SEQUENCE: 97

```
caggtgcagc tggtggagtc tgggggaggc gtggtccagc ctgggaggtc cctgagactc    60
tcctgtgtag cgtctggatt caccttcagt agttatggct ttcactgggt ccgccaggct   120
ccaggcaagg ggctggagtg ggtggcagtt atttggtatg atggaagtaa tgaaggctat   180
gtagactccg tgaggggccg attcaccatc tccagagact tttccaagaa cacgttgtat   240
ctgcaaatga acagcctgag aatcgaggac acggctgtgt attactgtgc gagacggggg   300
gactattaca ttatggacgt ctggggccaa gggaccacgg tcaccgtctc ctca         354
```

<210> SEQ ID NO 98
<211> LENGTH: 118
<212> TYPE: PRT
<213> ORGANISM: Artificial Sequence
<220> FEATURE:
<223> OTHER INFORMATION: synthetic

<400> SEQUENCE: 98

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Asn Glu Gly Tyr Val Asp Ser Val
    50                  55                  60

Arg Gly Arg Phe Thr Ile Ser Arg Asp Phe Ser Lys Asn Thr Leu Tyr
65                  70                  75                  80

Leu Gln Met Asn Ser Leu Arg Ile Glu Asp Thr Ala Val Tyr Tyr Cys
                85                  90                  95

Ala Arg Arg Gly Asp Tyr Tyr Ile Met Asp Val Trp Gly Gln Gly Thr
            100                 105                 110

Thr Val Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcacct tcagtagtta tggc                                            24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Phe Thr Phe Ser Ser Tyr Gly
1               5
```

<210> SEQ ID NO 101
<211> LENGTH: 24

```
<212> TYPE: DNA
<213> ORGANISM: Artificial Sequence
<220> FEATURE:
<223> OTHER INFORMATION: synthetic

<400> SEQUENCE: 101
atttggtatg atggaagtaa tgaa                                         24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Trp Tyr Asp Gly Ser Asn Glu
1               5

<210> SEQ ID NO 103
<211> LENGTH: 33
<212> TYPE: DNA
<213> ORGANISM: Artificial Sequence
<220> FEATURE:
<223> OTHER INFORMATION: synthetic

<400> SEQUENCE: 103
gcgagacggg gggactatta cattatggac gtc                               33

<210> SEQ ID NO 104
<211> LENGTH: 11
<212> TYPE: PRT
<213> ORGANISM: Artificial Sequence
<220> FEATURE:
<223> OTHER INFORMATION: synthetic

<400> SEQUENCE: 104

Ala Arg Arg Gly Asp Tyr Tyr Ile Met Asp Val
1               5                   10

<210> SEQ ID NO 105
<211> LENGTH: 351
<212> TYPE: DNA
<213> ORGANISM: Artificial Sequence
<220> FEATURE:
<223> OTHER INFORMATION: synthetic

<400> SEQUENCE: 105
gaggtgcagc tggtgcagtc tggagcagag gtgaaaaagc ccggggagtc tctgaagatc     60
ttctgtaagg gttctggata cagctttatc aacgactgga tcggctgggt gcgccagatg    120
cccgggaaag gcctggaatg gatgggtctg atctttcctg gtgactctga taccagatat    180
agtccggttt tccaaggcca cgtcaccatc tcagccgacc agtccatcga caccgcctat    240
ctgcagtgga acagcctgaa ggcctcggac accgccatat attactgtgc ggtgttacga    300
tactggcact cgctatctg ggccgtggc accctggtca ccgtctcctc a                351

<210> SEQ ID NO 106
<211> LENGTH: 117
<212> TYPE: PRT
<213> ORGANISM: Artificial Sequence
<220> FEATURE:
<223> OTHER INFORMATION: synthetic

<400> SEQUENCE: 106
```

```
Glu Val Gln Leu Val Gln Ser Gly Ala Glu Val Lys Lys Pro Gly Glu
1               5                   10                  15

Ser Leu Lys Ile Phe Cys Lys Gly Ser Gly Tyr Ser Phe Ile Asn Asp
            20                  25                  30

Trp Ile Gly Trp Val Arg Gln Met Pro Gly Lys Gly Leu Glu Trp Met
        35                  40                  45

Gly Leu Ile Phe Pro Gly Asp Ser Asp Thr Arg Tyr Ser Pro Val Phe
50                  55                  60

Gln Gly His Val Thr Ile Ser Ala Asp Gln Ser Ile Asp Thr Ala Tyr
65                  70                  75                  80

Leu Gln Trp Asn Ser Leu Lys Ala Ser Asp Thr Ala Ile Tyr Tyr Cys
                85                  90                  95

Ala Val Leu Arg Tyr Trp His Phe Ala Ile Trp Gly Arg Gly Thr Leu
            100                 105                 110

Val Thr Val Ser Ser
        115
```

<210> SEQ ID NO 107
<211> LENGTH: 24
<212> TYPE: DNA
<213> ORGANISM: Artificial Sequence
<220> FEATURE:
<223> OTHER INFORMATION: synthetic

<400> SEQUENCE: 107
ggatacagct ttatcaacga ctgg         24

<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108

```
Gly Tyr Ser Phe Ile Asn Asp Trp
1               5
```

<210> SEQ ID NO 109
<211> LENGTH: 24
<212> TYPE: DNA
<213> ORGANISM: Artificial Sequence
<220> FEATURE:
<223> OTHER INFORMATION: synthetic

<400> SEQUENCE: 109
atctttcctg gtgactctga tacc         24

<210> SEQ ID NO 110
<211> LENGTH: 8
<212> TYPE: PRT
<213> ORGANISM: Artificial Sequence
<220> FEATURE:
<223> OTHER INFORMATION: synthetic

<400> SEQUENCE: 110

```
Ile Phe Pro Gly Asp Ser Asp Thr
1               5
```

<210> SEQ ID NO 111
<211> LENGTH: 30
<212> TYPE: DNA
<213> ORGANISM: Artificial Sequence
<220> FEATURE:
<223> OTHER INFORMATION: synthetic

<400> SEQUENCE: 111
gcggtgttac gatactggca cttcgctatc    30

<210> SEQ ID NO 112
<211> LENGTH: 10
<212> TYPE: PRT
<213> ORGANISM: Artificial Sequence
<220> FEATURE:
<223> OTHER INFORMATION: synthetic

<400> SEQUENCE: 112

Ala Val Leu Arg Tyr Trp His Phe Ala Ile
1               5                   10

<210> SEQ ID NO 113
<211> LENGTH: 351
<212> TYPE: DNA
<213> ORGANISM: Artificial Sequence
<220> FEATURE:
<223> OTHER INFORMATION: synthetic

<400> SEQUENCE: 113
gaggtgcagc tggtgcagtc tggaccagag gtgaaaaagc ccggggagtc tttgaagatc    60
gcctgtaagg cttctggata cagttttacc agctactgga tcggttgggt gcgccagatg   120
cccgggaaag gcctggagtg gatggggatc atctttcctg ctgactctga taccagatac   180
agcccgtcct tccaaggcca ggtcaccatc tcagccgaca gtccatcac caccgcctac   240 ctgcagtgga ggagtctgca ggcctcggac accgccaaat attactgtgt gcgacatgta   300
cgatggtccg gggagaactg gggccaggga accctggtca ccgtctcctc a            351

<210> SEQ ID NO 114
<211> LENGTH: 117
<212> TYPE: PRT
<213> ORGANISM: Artificial Sequence
<220> FEATURE:
<223> OTHER INFORMATION: synthetic

<400> SEQUENCE: 114

Glu Val Gln Leu Val Gln Ser Gly Pro Glu Val Lys Lys Pro Gly Glu
1               5                   10                  15

Ser Leu Lys Ile Ala Cys Lys Ala Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Phe Pro Ala Asp Ser Asp Thr Arg Tyr Ser Pro Ser Phe
        50                  55                  60

Gln Gly Gln Val Thr Ile Ser Ala Asp Lys Ser Ile Thr Thr Ala Tyr
65                  70                  75                  80

Leu Gln Trp Arg Ser Leu Gln Ala Ser Asp Thr Ala Lys Tyr Tyr Cys
                85                  90                  95

Val Arg His Val Arg Trp Ser Gly Glu Asn Trp Gly Gln Gly Thr Leu
            100                 105                 110

Val Thr Val Ser Ser
        115

<210> SEQ ID NO 115
<211> LENGTH: 24

<212> TYPE: DNA
<213> ORGANISM: Artificial Sequence
<220> FEATURE:
<223> OTHER INFORMATION: synthetic

<400> SEQUENCE: 115
ggatacagtt ttaccagcta ctgg                                         24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Tyr Ser Phe Thr Ser Tyr Trp
1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atctttcctg ctgactctga tacc                                         24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Phe Pro Ala Asp Ser Asp Thr
1               5

<210> SEQ ID NO 119
<211> LENGTH: 30
<212> TYPE: DNA
<213> ORGANISM: Artificial Sequence
<220> FEATURE:
<223> OTHER INFORMATION: synthetic

<400> SEQUENCE: 119
gtgcgacatg tacgatggtc cggggagaac                                   30

<210> SEQ ID NO 120
<211> LENGTH: 10
<212> TYPE: PRT
<213> ORGANISM: Artificial Sequence
<220> FEATURE:
<223> OTHER INFORMATION: synthetic

<400> SEQUENCE: 120

Val Arg His Val Arg Trp Ser Gly Glu Asn
1               5                   10

<210> SEQ ID NO 121
<211> LENGTH: 351
<212> TYPE: DNA
<213> ORGANISM: Artificial Sequence
<220> FEATURE:
<223> OTHER INFORMATION: synthetic

<400> SEQUENCE: 121

```
gaggtgcagc tggtgcagtc tggagcagaa gtaagaaagc ccggggagtc tctgaagatc    60
tcctgtaagg gttctggatt cagttttacc agctactgga tcggctgggt gcgccagatg   120
cccgggaaag gcctggagtg gatggggatc atctttcctg ctgactctga taccagatac   180
agcccgtcct tccaaggcca agtcaccatc tcggccgaca gtccatcaa caccgcctac    240
ctgcagtgga aagcctgaa ggtctcggac accgccatgt attactgtac gaaactacag    300
tactggtact cgatctctg gggccgtggc accctggtca ccgtctcctc a             351
```

<210> SEQ ID NO 122
<211> LENGTH: 117
<212> TYPE: PRT
<213> ORGANISM: Artificial Sequence
<220> FEATURE:
<223> OTHER INFORMATION: synthetic

<400> SEQUENCE: 122

```
Glu Val Gln Leu Val Gln Ser Gly Ala Glu Val Arg Lys Pro Gly Glu
1               5                   10                  15
Ser Leu Lys Ile Ser Cys Lys Gly Ser Gly Phe Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Phe Pro Ala Asp Ser Asp Thr Arg Tyr Ser Pro Ser Phe
    50                  55                  60
Gln Gly Gln Val Thr Ile Ser Ala Asp Lys Ser Ile Asn Thr Ala Tyr
65                  70                  75                  80
Leu Gln Trp Arg Ser Leu Lys Val Ser Asp Thr Ala Met Tyr Tyr Cys
                85                  90                  95
Thr Lys Leu Gln Tyr Trp Tyr Phe Asp Leu Trp Gly Arg Gly Thr Leu
            100                 105                 110
Val Thr Val Ser Ser
        115
```

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123

```
ggattcagtt ttaccagcta ctgg                                          24
```

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

```
Gly Phe Ser Phe Thr Ser Tyr Trp
1               5
```

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atctttcctg ctgactctga tacc                                          24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Ile Phe Pro Ala Asp Ser Asp Thr
1               5

<210> SEQ ID NO 127
<211> LENGTH: 30
<212> TYPE: DNA
<213> ORGANISM: Artificial Sequence
<220> FEATURE:
<223> OTHER INFORMATION: synthetic

<400> SEQUENCE: 127
acgaaactac agtactggta cttcgatctc                                    30

<210> SEQ ID NO 128
<211> LENGTH: 10
<212> TYPE: PRT
<213> ORGANISM: Artificial Sequence
<220> FEATURE:
<223> OTHER INFORMATION: synthetic

<400> SEQUENCE: 128

Thr Lys Leu Gln Tyr Trp Tyr Phe Asp Leu
1               5                   10

<210> SEQ ID NO 129
<211> LENGTH: 354
<212> TYPE: DNA
<213> ORGANISM: Artificial Sequence
<220> FEATURE:
<223> OTHER INFORMATION: synthetic

<400> SEQUENCE: 129
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcactt atatggtatg atggaagtaa taaatacttt   180
gcagactccg tgaagggccg attcaccatc tccagagaca tttccaagaa cacgctgtat   240
ctgcaaatga acagcctgag agccgaggac acggctgtgt attactgtgc gagagatggg   300
gactactacg gtatggacgt ctggggccag gggaccacgg tcaccgtctc ctca         354

<210> SEQ ID NO 130
<211> LENGTH: 118
<212> TYPE: PRT
<213> ORGANISM: Artificial Sequence
<220> FEATURE:
<223> OTHER INFORMATION: synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Phe Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Tyr Gly Met Asp Val Trp Gly Gln Gly Thr
            100                 105                 110

Thr Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcacct tcagtagcta tggc                                          24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Phe Ser Ser Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatggtatg atggaagtaa taaa                                          24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Trp Tyr Asp Gly Ser Asn Lys
1               5

<210> SEQ ID NO 135
<211> LENGTH: 33
<212> TYPE: DNA
<213> ORGANISM: Artificial Sequence
<220> FEATURE:
<223> OTHER INFORMATION: synthetic

<400> SEQUENCE: 135
gcgagagatg gggactacta cggtatggac gtc                                    33

<210> SEQ ID NO 136
<211> LENGTH: 11
<212> TYPE: PRT
<213> ORGANISM: Artificial Sequence
<220> FEATURE:
<223> OTHER INFORMATION: synthetic

<400> SEQUENCE: 136

Ala Arg Asp Gly Asp Tyr Tyr Gly Met Asp Val
1               5                   10

<210> SEQ ID NO 137
<211> LENGTH: 375
<212> TYPE: DNA
<213> ORGANISM: Artificial Sequence
<220> FEATURE:
<223> OTHER INFORMATION: synthetic

<400> SEQUENCE: 137
gaagtgcagc tggtggagtc tgggggaggt ctggtacagc ctggcaggtc cctgagactc     60
tcctgtacaa cctctggatt cacctttgat gattatgcca tgcactgggt ccggcaagtt    120
ccagggcagg gcctggagtg gtcgcaggt cttagctgga acagtgatac cataggctat    180
gcggactctg tgaagggccg attcaccatc tccagagaca acgccaagaa ttccctgtat    240
ctgcaaatga aaagtctgaa agctgaggac acggccttat attactgtac aaaagatttc    300
taccatagtt tgaataattg gaactactac tactttgact actggggcca gggaaccctg    360
gtcaccgtct cctca                                                     375

<210> SEQ ID NO 138
<211> LENGTH: 125
<212> TYPE: PRT
<213> ORGANISM: Artificial Sequence
<220> FEATURE:
<223> OTHER INFORMATION: synthetic

<400> SEQUENCE: 138

Glu Val Gln Leu Val Glu Ser Gly Gly Leu Val Gln Pro Gly Arg
1               5                   10                  15

Ser Leu Arg Leu Ser Cys Thr Thr Ser Gly Phe Thr Phe Asp Asp Tyr
            20                  25                  30

Ala Met His Trp Val Arg Gln Val Pro Gly Gln Gly Leu Glu Trp Val
        35                  40                  45

Ala Gly Leu Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Lys Ala Glu Asp Thr Ala Leu Tyr Tyr Cys
                85                  90                  95

Thr Lys Asp Phe Tyr His Ser Leu Asn Asn Trp Asn Tyr Tyr Tyr Phe
            100                 105                 110

Asp Tyr Trp Gly Gln Gly Thr Leu Val Thr Val Ser Ser
        115                 120                 125

<210> SEQ ID NO 139
<211> LENGTH: 24

```
<212> TYPE: DNA
<213> ORGANISM: Artificial Sequence
<220> FEATURE:
<223> OTHER INFORMATION: synthetic

<400> SEQUENCE: 139
ggattcacct ttgatgatta tgcc                                              24

<210> SEQ ID NO 140
<211> LENGTH: 8
<212> TYPE: PRT
<213> ORGANISM: Artificial Sequence
<220> FEATURE:
<223> OTHER INFORMATION: synthetic

<400> SEQUENCE: 140

Gly Phe Thr Phe Asp Asp Tyr Ala
1               5

<210> SEQ ID NO 141
<211> LENGTH: 24
<212> TYPE: DNA
<213> ORGANISM: Artificial Sequence
<220> FEATURE:
<223> OTHER INFORMATION: synthetic

<400> SEQUENCE: 141
cttagctgga acagtgatac cata                                              24

<210> SEQ ID NO 142
<211> LENGTH: 8
<212> TYPE: PRT
<213> ORGANISM: Artificial Sequence
<220> FEATURE:
<223> OTHER INFORMATION: synthetic

<400> SEQUENCE: 142

Leu Ser Trp Asn Ser Asp Thr Ile
1               5

<210> SEQ ID NO 143
<211> LENGTH: 54
<212> TYPE: DNA
<213> ORGANISM: Artificial Sequence
<220> FEATURE:
<223> OTHER INFORMATION: synthetic

<400> SEQUENCE: 143
acaaaagatt tctaccatag tttgaataat tggaactact actactttga ctac             54

<210> SEQ ID NO 144
<211> LENGTH: 18
<212> TYPE: PRT
<213> ORGANISM: Artificial Sequence
<220> FEATURE:
<223> OTHER INFORMATION: synthetic

<400> SEQUENCE: 144

Thr Lys Asp Phe Tyr His Ser Leu Asn Asn Trp Asn Tyr Tyr Tyr Phe
1               5                   10                  15

Asp Tyr

<210> SEQ ID NO 145
<211> LENGTH: 324
<212> TYPE: DNA
<213> ORGANISM: Artificial Sequence
```

<220> FEATURE:
<223> OTHER INFORMATION: synthetic

<400> SEQUENCE: 145

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 146
<211> LENGTH: 108
<212> TYPE: PRT
<213> ORGANISM: Artificial Sequence
<220> FEATURE:
<223> OTHER INFORMATION: synthetic

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 147
<211> LENGTH: 18
<212> TYPE: DNA
<213> ORGANISM: Artificial Sequence
<220> FEATURE:
<223> OTHER INFORMATION: synthetic

<400> SEQUENCE: 147

```
cagagcatta gcagctat                                                  18
```

<210> SEQ ID NO 148
<211> LENGTH: 6
<212> TYPE: PRT
<213> ORGANISM: Artificial Sequence
<220> FEATURE:
<223> OTHER INFORMATION: synthetic

<400> SEQUENCE: 148

```
Gln Ser Ile Ser Ser Tyr
1               5
```

<210> SEQ ID NO 149
<211> LENGTH: 9
<212> TYPE: DNA
<213> ORGANISM: Artificial Sequence
<220> FEATURE:

<223> OTHER INFORMATION: synthetic

<400> SEQUENCE: 149 gctgcatcc                                                                9

<210> SEQ ID NO 150
<211> LENGTH: 3
<212> TYPE: PRT
<213> ORGANISM: Artificial Sequence
<220> FEATURE:
<223> OTHER INFORMATION: synthetic

<400> SEQUENCE: 150

Ala Ala Ser
1

<210> SEQ ID NO 151
<211> LENGTH: 30
<212> TYPE: DNA
<213> ORGANISM: Artificial Sequence
<220> FEATURE:
<223> OTHER INFORMATION: synthetic

<400> SEQUENCE: 151
caacagagtt acagtacccc tccgatcacc                                         30

<210> SEQ ID NO 152
<211> LENGTH: 10
<212> TYPE: PRT
<213> ORGANISM: Artificial Sequence
<220> FEATURE:
<223> OTHER INFORMATION: synthetic

<400> SEQUENCE: 152

Gln Gln Ser Tyr Ser Thr Pro Pro Ile Thr
1               5                   10

<210> SEQ ID NO 153
<211> LENGTH: 375
<212> TYPE: DNA
<213> ORGANISM: Artificial Sequence
<220> FEATURE:
<223> OTHER INFORMATION: synthetic

<400> SEQUENCE: 153
cagctgcagc tgcaggagtc gggcccagga ctggtgaagc cttcggagac cctgtccctc        60
acctgcactg tctctggtgg ctccatcagc agcagtagtt actactgggt ctggatccgc       120
cagcccccag ggaaggggct ggaatggatt ggtaatatct attttagtgg gagcacatac       180
tacaacccgt ccctcaagag tcgagtcacc ataaccgttg acacgtccaa gaaccagttc       240
tccctgaaaa tgacctctgt gaccgccgca gacacggctg tatattactg tgcgagaccc       300
ttctatggtt cgagggggga ctactactac ggtatggacg tctggggcca agggaccacg       360
gtcaccgtct cctca                                                        375

<210> SEQ ID NO 154
<211> LENGTH: 125
<212> TYPE: PRT
<213> ORGANISM: Artificial Sequence
<220> FEATURE:
<223> OTHER INFORMATION: synthetic

<400> SEQUENCE: 154

Gln Leu Gln Leu Gln Glu Ser Gly Pro Gly Leu Val Lys Pro Ser Glu

```
  1               5                   10                  15
Thr Leu Ser Leu Thr Cys Thr Val Ser Gly Gly Ser Ile Ser Ser Ser
                 20                  25                  30

Ser Tyr Tyr Trp Val Trp Ile Arg Gln Pro Pro Gly Lys Gly Leu Glu
             35                  40                  45

Trp Ile Gly Asn Ile Tyr Phe Ser Gly Ser Thr Tyr Tyr Asn Pro Ser
         50                  55                  60

Leu Lys Ser Arg Val Thr Ile Thr Val Asp Thr Ser Lys Asn Gln Phe
65                  70                  75                  80

Ser Leu Lys Met Thr Ser Val Thr Ala Ala Asp Thr Ala Val Tyr Tyr
                 85                  90                  95

Cys Ala Arg Pro Phe Tyr Gly Ser Arg Gly Asp Tyr Tyr Tyr Gly Met
                100                 105                 110

Asp Val Trp Gly Gln Gly Thr Thr Val Thr Val Ser Ser
            115                 120                 125

<210> SEQ ID NO 155
<211> LENGTH: 30
<212> TYPE: DNA
<213> ORGANISM: Artificial Sequence
<220> FEATURE:
<223> OTHER INFORMATION: synthetic

<400> SEQUENCE: 155
ggtggctcca tcagcagcag tagttactac                                     30

<210> SEQ ID NO 156
<211> LENGTH: 10
<212> TYPE: PRT
<213> ORGANISM: Artificial Sequence
<220> FEATURE:
<223> OTHER INFORMATION: synthetic

<400> SEQUENCE: 156

Gly Gly Ser Ile Ser Ser Ser Tyr Tyr
1               5                   10

<210> SEQ ID NO 157
<211> LENGTH: 21
<212> TYPE: DNA
<213> ORGANISM: Artificial Sequence
<220> FEATURE:
<223> OTHER INFORMATION: synthetic

<400> SEQUENCE: 157
atctatttta gtgggagcac a                                              21

<210> SEQ ID NO 158
<211> LENGTH: 7
<212> TYPE: PRT
<213> ORGANISM: Artificial Sequence
<220> FEATURE:
<223> OTHER INFORMATION: synthetic

<400> SEQUENCE: 158

Ile Tyr Phe Ser Gly Ser Thr
1               5

<210> SEQ ID NO 159
<211> LENGTH: 51
<212> TYPE: DNA
<213> ORGANISM: Artificial Sequence
<220> FEATURE:
```

<223> OTHER INFORMATION: synthetic

<400> SEQUENCE: 159
gcgagaccct tctatggttc gagggggggac tactactacg gtatggacgt c        51

<210> SEQ ID NO 160
<211> LENGTH: 17
<212> TYPE: PRT
<213> ORGANISM: Artificial Sequence
<220> FEATURE:
<223> OTHER INFORMATION: synthetic

<400> SEQUENCE: 160

Ala Arg Pro Phe Tyr Gly Ser Arg Gly Asp Tyr Tyr Gly Met Asp
1               5                   10                  15
Val

<210> SEQ ID NO 161
<211> LENGTH: 324
<212> TYPE: DNA
<213> ORGANISM: Artificial Sequence
<220> FEATURE:
<223> OTHER INFORMATION: synthetic

<400> SEQUENCE: 161
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                           324

<210> SEQ ID NO 162
<211> LENGTH: 108
<212> TYPE: PRT
<213> ORGANISM: Artificial Sequence
<220> FEATURE:
<223> OTHER INFORMATION: synthetic

<400> SEQUENCE: 162

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105

<210> SEQ ID NO 163
<211> LENGTH: 21
<212> TYPE: DNA
<213> ORGANISM: Artificial Sequence
<220> FEATURE:
<223> OTHER INFORMATION: synthetic

<400> SEQUENCE: 163
cagagtgtta gcagcagcta c                                              21

<210> SEQ ID NO 164
<211> LENGTH: 7
<212> TYPE: PRT
<213> ORGANISM: Artificial Sequence
<220> FEATURE:
<223> OTHER INFORMATION: synthetic

<400> SEQUENCE: 164

Gln Ser Val Ser Ser Ser Tyr
1               5

<210> SEQ ID NO 165
<211> LENGTH: 9
<212> TYPE: DNA
<213> ORGANISM: Artificial Sequence
<220> FEATURE:
<223> OTHER INFORMATION: synthetic

<400> SEQUENCE: 165 ggtgcatcc                                                             9

<210> SEQ ID NO 166
<211> LENGTH: 3
<212> TYPE: PRT
<213> ORGANISM: Artificial Sequence
<220> FEATURE:
<223> OTHER INFORMATION: synthetic

<400> SEQUENCE: 166

Gly Ala Ser
1

<210> SEQ ID NO 167
<211> LENGTH: 27
<212> TYPE: DNA
<213> ORGANISM: Artificial Sequence
<220> FEATURE:
<223> OTHER INFORMATION: synthetic

<400> SEQUENCE: 167
cagcagtatg gtagctcacc ttggacg                                        27

<210> SEQ ID NO 168
<211> LENGTH: 9
<212> TYPE: PRT
<213> ORGANISM: Artificial Sequence
<220> FEATURE:
<223> OTHER INFORMATION: synthetic

<400> SEQUENCE: 168

Gln Gln Tyr Gly Ser Ser Pro Trp Thr
1               5

<210> SEQ ID NO 169
<211> LENGTH: 582
<212> TYPE: PRT
<213> ORGANISM: Artificial Sequence
<220> FEATURE:
<223> OTHER INFORMATION: IsdB-6xHis
      aa 1-2 and 575-576: linker
      aa 3-574: aa 41-613 of WP_063557416.1

<400> SEQUENCE: 169

Ala Ser Ala Glu Glu Thr Gly Gly Thr Asn Thr Glu Ala Gln Pro Lys
1               5                   10                  15

Thr Glu Ala Val Ala Ser Pro Thr Thr Thr Ser Glu Lys Ala Pro Glu
            20                  25                  30

Thr Lys Pro Val Ala Asn Ala Val Ser Val Ser Asn Lys Glu Val Glu
            35                  40                  45

Ala Pro Thr Ser Glu Thr Lys Glu Ala Lys Glu Val Lys Glu Val Lys
50                  55                  60

Ala Pro Lys Glu Thr Lys Glu Val Lys Pro Ala Ala Lys Ala Thr Asn
65                  70                  75                  80

Asn Thr Tyr Pro Ile Leu Asn Gln Glu Leu Arg Glu Ala Ile Lys Asn
                85                  90                  95

Pro Ala Ile Lys Asp Lys Asp His Ser Ala Pro Asn Ser Arg Pro Ile
            100                 105                 110

Asp Phe Glu Met Lys Lys Asp Gly Thr Gln Gln Phe Tyr His Tyr
            115                 120                 125

Ala Ser Ser Val Lys Pro Ala Arg Val Ile Phe Thr Asp Ser Lys Pro
130                 135                 140

Glu Ile Glu Leu Gly Leu Gln Ser Gly Gln Phe Trp Arg Lys Phe Glu
145                 150                 155                 160

Val Tyr Glu Gly Asp Lys Lys Leu Pro Ile Lys Leu Val Ser Tyr Asp
                165                 170                 175

Thr Val Lys Asp Tyr Ala Tyr Ile Arg Phe Ser Val Ser Asn Gly Thr
            180                 185                 190

Lys Ala Val Lys Ile Val Ser Ser Thr His Phe Asn Asn Lys Glu Glu
            195                 200                 205

Lys Tyr Asp Tyr Thr Leu Met Glu Phe Ala Gln Pro Ile Tyr Asn Ser
            210                 215                 220

Ala Asp Lys Phe Lys Thr Glu Glu Asp Tyr Lys Ala Glu Lys Leu Leu
225                 230                 235                 240

Ala Pro Tyr Lys Lys Ala Lys Thr Leu Glu Arg Gln Val Tyr Glu Leu
            245                 250                 255

Asn Lys Ile Gln Asp Lys Leu Pro Glu Lys Leu Lys Ala Glu Tyr Lys
            260                 265                 270

Lys Lys Leu Glu Asp Thr Lys Lys Ala Leu Asp Glu Gln Val Lys Ser
            275                 280                 285

Ala Ile Thr Glu Phe Gln Asn Val Gln Pro Thr Asn Glu Lys Met Thr
290                 295                 300

Asp Leu Gln Asp Thr Lys Tyr Val Val Tyr Glu Ser Val Glu Asn Asn
305                 310                 315                 320

Glu Ser Met Met Asp Thr Phe Val Lys His Pro Ile Lys Thr Gly Met
            325                 330                 335

Leu Asn Gly Lys Lys Tyr Met Val Met Glu Thr Thr Asn Asp Asp Tyr
            340                 345                 350

Trp Lys Asp Phe Met Val Glu Gly Gln Arg Val Arg Thr Ile Ser Lys
            355                 360                 365

Asp Ala Lys Asn Asn Thr Arg Thr Ile Ile Phe Pro Tyr Val Glu Gly
            370                 375                 380

Lys Thr Leu Tyr Asp Ala Ile Val Lys Val His Val Lys Thr Ile Asp
385                 390                 395                 400

Tyr Asp Gly Gln Tyr His Val Arg Ile Val Asp Lys Glu Ala Phe Thr

```
                405                 410                 415
Lys Ala Asn Thr Asp Lys Ser Asn Lys Lys Glu Gln Gln Asp Asn Ser
            420                 425                 430

Ala Lys Lys Glu Ala Thr Pro Ala Thr Pro Ser Lys Pro Thr Pro Ser
            435                 440                 445

Pro Val Glu Lys Glu Ser Gln Lys Gln Asp Ser Gln Lys Asp Asp Asn
    450                 455                 460

Lys Gln Leu Pro Ser Val Glu Lys Glu Asn Asp Ala Ser Ser Glu Ser
465                 470                 475                 480

Gly Lys Asp Lys Thr Pro Ala Thr Lys Pro Thr Lys Gly Glu Val Glu
                485                 490                 495

Ser Ser Ser Thr Thr Pro Thr Lys Val Val Ser Thr Thr Gln Asn Val
            500                 505                 510

Ala Lys Pro Thr Thr Ala Ser Ser Lys Thr Thr Lys Asp Val Val Gln
            515                 520                 525

Thr Ser Ala Gly Ser Ser Glu Ala Lys Asp Ser Ala Pro Leu Gln Lys
    530                 535                 540

Ala Asn Ile Lys Asn Thr Asn Asp Gly His Thr Gln Ser Gln Asn Asn
545                 550                 555                 560

Lys Asn Thr Gln Glu Asn Lys Ala Lys Ser Leu Pro Gln Thr Leu Glu
                565                 570                 575

His His His His His His
            580

<210> SEQ ID NO 170
<211> LENGTH: 245
<212> TYPE: PRT
<213> ORGANISM: Artificial Sequence
<220> FEATURE:
<223> OTHER INFORMATION: C1q subcomponent a chain
      amino acids 1-245 of accession number NP_057075.1

<400> SEQUENCE: 170

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
            115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175
```

```
Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 171
<211> LENGTH: 253
<212> TYPE: PRT
<213> ORGANISM: Artificial Sequence
<220> FEATURE:
<223> OTHER INFORMATION: C1q subcomponent b chain
      amino acids 1-253 of accession number NP_000482.3

<400> SEQUENCE: 171

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
            20                  25                  30

Gly Pro Pro Ala Ile Pro Gly Ile Pro Gly Ile Pro Gly Thr Pro Gly
        35                  40                  45

Pro Asp Gly Gln Pro Gly Thr Pro Gly Ile Lys Gly Glu Lys Gly Leu
50                  55                  60

Pro Gly Leu Ala Gly Asp His Gly Glu Phe Gly Glu Lys Gly Asp Pro
65                  70                  75                  80

Gly Ile Pro Gly Asn Pro Gly Lys Val Gly Pro Lys Gly Pro Met Gly
                85                  90                  95

Pro Lys Gly Gly Pro Gly Ala Pro Gly Ala Pro Gly Pro Lys Gly Glu
            100                 105                 110

Ser Gly Asp Tyr Lys Ala Thr Gln Lys Ile Ala Phe Ser Ala Thr Arg
        115                 120                 125

Thr Ile Asn Val Pro Leu Arg Arg Asp Gln Thr Ile Arg Phe Asp His
130                 135                 140

Val Ile Thr Asn Met Asn Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
            180                 185                 190

Lys Val Val Thr Phe Cys Asp Tyr Ala Tyr Asn Thr Phe Gln Val Thr
        195                 200                 205

Thr Gly Gly Met Val Leu Lys Leu Glu Gln Gly Glu Asn Val Phe Leu
210                 215                 220

Gln Ala Thr Asp Lys Asn Ser Leu Leu Gly Met Glu Gly Ala Asn Ser
225                 230                 235                 240

Ile Phe Ser Gly Phe Leu Leu Phe Pro Asp Met Glu Ala
                245                 250

<210> SEQ ID NO 172
<211> LENGTH: 245
<212> TYPE: PRT
<213> ORGANISM: Artificial Sequence
```

-continued

```
<220> FEATURE:
<223> OTHER INFORMATION: C1q subcomponent c chain
      amino acids 1-245 of accession number NP_758957.2

<400> SEQUENCE: 172
```

| | | | | | | | | | | | | | | |
|---|---|---|---|---|---|---|---|---|---|---|---|---|---|---|
| Met | Asp | Val | Gly | Pro | Ser | Ser | Leu | Pro | His | Leu | Gly | Leu | Lys | Leu | Leu |
| 1 | | | | 5 | | | | | 10 | | | | | 15 | |
| Leu | Leu | Leu | Leu | Leu | Leu | Pro | Leu | Arg | Gly | Gln | Ala | Asn | Thr | Gly | Cys |
| | | | 20 | | | | | 25 | | | | | 30 | | |
| Tyr | Gly | Ile | Pro | Gly | Met | Pro | Gly | Leu | Pro | Gly | Ala | Pro | Gly | Lys | Asp |
| | | 35 | | | | | 40 | | | | | 45 | | | |
| Gly | Tyr | Asp | Gly | Leu | Pro | Gly | Pro | Lys | Gly | Glu | Pro | Gly | Ile | Pro | Ala |
| 50 | | | | | 55 | | | | | 60 | | | | | |
| Ile | Pro | Gly | Ile | Arg | Gly | Pro | Lys | Gly | Gln | Lys | Gly | Glu | Pro | Gly | Leu |
| 65 | | | | 70 | | | | | 75 | | | | | 80 | |
| Pro | Gly | His | Pro | Gly | Lys | Asn | Gly | Pro | Met | Gly | Pro | Pro | Gly | Met | Pro |
| | | | 85 | | | | | 90 | | | | | 95 | | |
| Gly | Val | Pro | Gly | Pro | Met | Gly | Ile | Pro | Gly | Glu | Pro | Gly | Glu | Glu | Gly |
| | | | | 100 | | | | | 105 | | | | | 110 | |
| Arg | Tyr | Lys | Gln | Lys | Phe | Gln | Ser | Val | Phe | Thr | Val | Thr | Arg | Gln | Thr |
| | | | 115 | | | | | 120 | | | | | 125 | | |
| His | Gln | Pro | Pro | Ala | Pro | Asn | Ser | Leu | Ile | Arg | Phe | Asn | Ala | Val | Leu |
| | | 130 | | | | | 135 | | | | | 140 | | | |
| Thr | Asn | Pro | Gln | Gly | Asp | Tyr | Asp | Thr | Ser | Thr | Gly | Lys | Phe | Thr | Cys |
| 145 | | | | | 150 | | | | | 155 | | | | | 160 |
| Lys | Val | Pro | Gly | Leu | Tyr | Tyr | Phe | Val | Tyr | His | Ala | Ser | His | Thr | Ala |
| | | | | 165 | | | | | 170 | | | | | 175 | |
| Asn | Leu | Cys | Val | Leu | Leu | Tyr | Arg | Ser | Gly | Val | Lys | Val | Val | Thr | Phe |
| | | | 180 | | | | | 185 | | | | | 190 | | |
| Cys | Gly | His | Thr | Ser | Lys | Thr | Asn | Gln | Val | Asn | Ser | Gly | Gly | Val | Leu |
| | | | 195 | | | | | 200 | | | | | 205 | | |
| Leu | Arg | Leu | Gln | Val | Gly | Glu | Glu | Val | Trp | Leu | Ala | Val | Asn | Asp | Tyr |
| | | 210 | | | | | 215 | | | | | 220 | | | |
| Tyr | Asp | Met | Val | Gly | Ile | Gln | Gly | Ser | Asp | Ser | Val | Phe | Ser | Gly | Phe |
| 225 | | | | | 230 | | | | | 235 | | | | | 240 |
| Leu | Leu | Phe | Pro | Asp | | | | | | | | | | | |
| | | | | 245 | | | | | | | | | | | |

```
<210> SEQ ID NO 173
<211> LENGTH: 449
<212> TYPE: PRT
<213> ORGANISM: Artificial Sequence
<220> FEATURE:
<223> OTHER INFORMATION: H1H20631D- Full length Heavy Chain-C1Q arm
      (H1X17736)

<400> SEQUENCE: 173
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Val | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Ser | Leu | Asp | Asp | Tyr |
| | | | 20 | | | | | 25 | | | | | 30 | | |
| Ala | Met | His | Trp | Val | Arg | Gln | Thr | Pro | Gly | Lys | Gly | Leu | Glu | Trp | Val |
| | | | | 35 | | | | | 40 | | | | | 45 | |
| Ser | Leu | Ile | Ser | Gly | Asp | Gly | Ser | Arg | Thr | Ser | Tyr | Ala | Asp | Ser | Val |
| | | | 50 | | | | | 55 | | | | | 60 | | |
| Lys | Gly | Arg | Phe | Thr | Ile | Ser | Arg | Asp | Asn | Ser | Lys | Asn | Ser | Leu | Tyr |
| 65 | | | | | 70 | | | | | 75 | | | | | 80 |

Leu Lys Met Asn Ser Leu Arg Thr Glu Asp Thr Ala Leu Tyr Tyr Cys
                85                  90                  95

Thr Lys Asp Pro His Asn Ser Asn Trp Phe Asp Pro Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
            435                 440                 445

Lys

<210> SEQ ID NO 174
<211> LENGTH: 455
<212> TYPE: PRT
<213> ORGANISM: Artificial Sequence
<220> FEATURE:
<223> OTHER INFORMATION: H1H20631D-- Full length Heavy Chain IsdB arm (H1H20295)

<400> SEQUENCE: 174

| | | | | | | | | | | | | | | |
|---|---|---|---|---|---|---|---|---|---|---|---|---|---|---|
| Glu | Val | Gln | Leu | Val | Glu | Ser | Gly | Gly | Leu | Val | Gln | Pro | Gly | Arg |
| 1 | | | | 5 | | | | | 10 | | | | | 15 |
| Ser | Leu | Arg | Leu | Ser | Cys | Thr | Thr | Ser | Gly | Phe | Thr | Phe | Asp | Asp |
| | | | 20 | | | | | 25 | | | | | 30 | |
| Tyr | Ala | Met | His | Trp | Val | Arg | Gln | Val | Pro | Gly | Gln | Gly | Leu | Glu |
| | | 35 | | | | | 40 | | | | | 45 | | |
| Trp | Val | Ala | Gly | Leu | Ser | Trp | Asn | Ser | Asp | Thr | Ile | Gly | Tyr | Ala |
| | 50 | | | | | 55 | | | | | 60 | | | |

(H1H20295)

<400> SEQUENCE: 174

Glu Val Gln Leu Val Glu Ser Gly Gly Leu Val Gln Pro Gly Arg
1               5                   10                  15

Ser Leu Arg Leu Ser Cys Thr Thr Ser Gly Phe Thr Phe Asp Asp
            20                  25                  30

Tyr Ala Met His Trp Val Arg Gln Val Pro Gly Gln Gly Leu Glu Trp Val
        35                  40                  45

Ala Gly Leu Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Lys Ala Glu Asp Thr Ala Leu Tyr Tyr Cys
                85                  90                  95

Thr Lys Asp Phe Tyr His Ser Leu Asn Asn Trp Asn Tyr Tyr Tyr Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

```
Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 175
<211> LENGTH: 215
<212> TYPE: PRT
<213> ORGANISM: Artificial Sequence
<220> FEATURE:
<223> OTHER INFORMATION: H1H20631D Full length Light Chain (ULC1-39)

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215
```